US012692291B2

(12) United States Patent
Yang et al.

(10) Patent No.: US 12,692,291 B2
(45) Date of Patent: Jul. 28, 2026

(54) DIAMINE-LINKED MELANOCORTIN RECEPTOR-SPECIFIC CYCLIC PEPTIDES FOR OCULAR INDICATIONS

(71) Applicant: Boehringer Ingelheim International GmbH, Ingelheim am Rhein (DE)

(72) Inventors: Wei Yang, Edison, NJ (US); John H. Dodd, Spring Mills, PA (US); Axel Metzger, Jackson, NJ (US)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 107 days.

(21) Appl. No.: 17/811,625

(22) Filed: Jul. 11, 2022

(65) Prior Publication Data

US 2023/0040236 A1 Feb. 9, 2023

Related U.S. Application Data

(63) Continuation of application No. PCT/US2021/016007, filed on Feb. 1, 2021.

(60) Provisional application No. 62/969,311, filed on Feb. 3, 2020, provisional application No. 63/124,927, filed on Dec. 14, 2020.

(51) Int. Cl.

| | |
|---|---|
| ***C07K 7/56*** | (2006.01) |
| ***A61K 9/08*** | (2006.01) |
| ***A61K 38/00*** | (2006.01) |
| ***A61P 27/02*** | (2006.01) |

(52) U.S. Cl.

CPC .................. *C07K 7/56* (2013.01); *A61K 9/08* (2013.01); *A61P 27/02* (2018.01); *A61K 38/00* (2013.01)

(58) Field of Classification Search

None

See application file for complete search history.

(56) References Cited

U.S. PATENT DOCUMENTS

| | | | |
|---|---|---|---|
| 4,200,750 | A | 4/1980 | Warner, Jr. et al. |
| 4,938,763 | A | 7/1990 | Dunn et al. |
| 5,443,816 | A | 8/1995 | Zamora et al. |
| 5,558,085 | A | 9/1996 | Rubsamen et al. |
| 5,693,608 | A | 12/1997 | Bechgaard et al. |
| 5,908,825 | A | 6/1999 | Fasano et al. |
| 5,934,272 | A | 8/1999 | Lloyd et al. |
| 5,977,070 | A | 11/1999 | Piazza et al. |
| 6,116,237 | A | 9/2000 | Schultz et al. |
| 6,184,231 | B1 | 2/2001 | Hewawasam et al. |
| 6,187,344 | B1 | 2/2001 | Eljamal et al. |
| 6,257,232 | B1 | 7/2001 | Andersson et al. |
| 6,325,061 | B1 | 12/2001 | Dagsland |
| 6,358,530 | B1 | 3/2002 | Eljamal et al. |
| 6,432,438 | B1 | 8/2002 | Shukla |
| 6,503,481 | B1 | 1/2003 | Thurston et al. |
| 6,518,239 | B1 | 2/2003 | Kuo et al. |
| 6,520,179 | B1 | 2/2003 | Schuckmann et al. |
| 6,551,578 | B2 | 4/2003 | Adjei et al. |
| 6,572,893 | B2 | 6/2003 | Gordon et al. |
| 6,579,968 | B1 | 6/2003 | Blood et al. |
| 6,582,729 | B1 | 6/2003 | Eljamal et al. |
| 6,585,957 | B1 | 7/2003 | Adjei et al. |
| 6,596,261 | B1 | 7/2003 | Adjei et al. |
| 6,610,272 | B1 | 8/2003 | Cutie et al. |
| 6,632,456 | B1 | 10/2003 | Bäckström et al. |
| 6,645,466 | B1 | 11/2003 | Keller et al. |
| 6,655,380 | B1 | 12/2003 | Andersson et al. |
| 6,673,767 | B1 | 1/2004 | Brodbeck et al. |
| 6,698,425 | B1 | 3/2004 | Widerström |

(Continued)

FOREIGN PATENT DOCUMENTS

| | | | |
|---|---|---|---|
| CN | 101302246 | A | 11/2008 |
| JP | 2003503357 | A | 1/2003 |

(Continued)

OTHER PUBLICATIONS

International Search Report and Written Opinion Received for PCT Application No. PCT/US2021/016007, mailed on May 27, 2021, 15 Pages.

(Continued)

*Primary Examiner* — Christina Bradley

(74) *Attorney, Agent, or Firm* — Troutman Pepper Locke LLP

(57) ABSTRACT

Receptor-specific cyclic peptides of the formula (I)

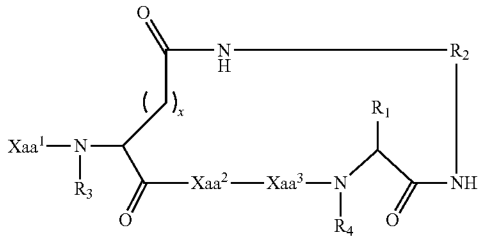

where $Xaa^1$, $Xaa^2$, $Xaa^3$, x, $R_1$, $R_2$, $R_3$ and $R_4$ are as defined in the specification, compositions and formulations including the peptides of the foregoing formula, and methods of preventing, ameliorating, or treating melanocortin receptor-mediated diseases, indications, conditions, and syndromes utilizing melanocortin receptor-specific cyclic peptides of formula I.

25 Claims, 2 Drawing Sheets

Specification includes a Sequence Listing.

(56) References Cited

U.S. PATENT DOCUMENTS

| | | | | |
|---|---|---|---|---|
| 6,881,398 | B2 | 4/2005 | Myrman et al. | |
| 6,907,880 | B1 | 6/2005 | Heckenmüller et al. | |
| 6,962,151 | B1 | 11/2005 | Knoch et al. | |
| 7,022,311 | B1 | 4/2006 | Ohkuma et al. | |
| 7,143,764 | B1 | 12/2006 | Dagsland et al. | |
| 7,169,603 | B2 | 1/2007 | Hedley et al. | |
| 7,186,401 | B2 | 3/2007 | Keller et al. | |
| 7,235,625 | B2 | 6/2007 | Diamond et al. | |
| 7,258,873 | B2 | 8/2007 | Truong-Le et al. | |
| 7,387,794 | B2 | 6/2008 | Yang | |
| 7,481,212 | B2 | 1/2009 | Schuler et al. | |
| 7,582,284 | B2 | 9/2009 | Kordikowski et al. | |
| 7,820,164 | B2 | 10/2010 | Hansen et al. | |
| 8,492,517 | B2 | 7/2013 | Yang et al. | |
| 8,877,890 | B2 | 11/2014 | Yang et al. | |
| 9,447,148 | B2 | 9/2016 | Yang et al. | |
| 10,017,539 | B2 | 7/2018 | Yang et al. | |
| 10,711,039 | B2 | 7/2020 | Yang et al. | |
| 11,286,280 | B2 | 3/2022 | Yang et al. | |
| 2004/0241232 | A1 | 12/2004 | Brown et al. | |
| 2005/0037951 | A1 | 2/2005 | Blood et al. | |
| 2005/0123509 | A1 | 6/2005 | Lehrman et al. | |
| 2005/0211244 | A1 | 9/2005 | Nilsson et al. | |
| 2006/0054166 | A1 | 3/2006 | Knoch et al. | |
| 2007/0140976 | A1 | 6/2007 | Chen et al. | |
| 2007/0298116 | A1 | 12/2007 | Bechtold-Peters et al. | |
| 2008/0066741 | A1 | 3/2008 | LeMahieu et al. | |
| 2009/0241949 | A1 | 10/2009 | Smutney et al. | |
| 2009/0297444 | A1 | 12/2009 | Perricone et al. | |
| 2012/0077957 | A1 * | 3/2012 | Chen ........................ | C07K 7/56 530/323 |
| 2014/0357575 | A1 | 12/2014 | Shi et al. | |
| 2019/0054150 | A1 | 2/2019 | Berenson et al. | |

FOREIGN PATENT DOCUMENTS

| | | | |
|---|---|---|---|
| JP | 2008542358 | A | 11/2008 |
| JP | 2012529433 | A | 11/2012 |
| WO | 2008142319 | A2 | 11/2008 |
| WO | 2009120656 | A1 | 10/2009 |
| WO | 2016/168388 | A2 | 10/2016 |
| WO | 2019/183472 | A1 | 9/2019 |
| WO | 2021/158463 | A1 | 8/2021 |

OTHER PUBLICATIONS

Invitation to Pay Additional Fees and, Where Applicable, Protest Fee Received for PCT Application No. PCT/US2021/016007, mailed on Apr. 6, 2021, 3 Pages.
International Preliminary Report on Patentability received for PCT Application No. PCT/US2021/016007, mailed on Aug. 18, 2022, 10 Pages.
Yang et al., "A novel TRPM8 agonist relieves dry eye discomfort", BMC Ophthalmology, vol. 17, No. 101, Jun. 26, 2017, 15 Pages.
Hruby et al., "Cyclic lactam alpha.-melanotropin analogs of Ac—Nle4-cyclo [Asp5 D-Phe7, Lys10]-.alpha.-melanocyte-stimulating hormone-(4-10)-NH2 with bulky aromatic amino acids at position 7 show high antagonist potency and selectivity at specific melanocortin receptors." J. Med. Chem 1195, vol. 38, 1995, 3454-3461.
Gilon et al., "Backbone Cyclization: A New Method for Conferring Conformational Constraint on Peptides." Biopolymers: Original Research on Biomolecules vol. 31, No. 6, pp. 745-750.
Catania et al., "Autocrine inhibitory influences of-melanocyte-stimulating hormone in malignant pleural mesothelioma." Journal of Leukocyte Biology, vol. 75, No. 2, Feb. 2004, pp. 253-259.
Chen et al., "A colorimetric assay for measuring activation of Gs-and Gq-coupled signaling pathways." Analytical Biochemistry, vol. 226, No. 2, 1995, pp. 349-354.
Cryan et al., "Carrier-based strategies for targeting protein and peptide drugs to the lungs." The AAPS journal, vol. 7, No. 1, Mar. 24, 2005, pp. E20-E41.
Kent et al., "Development of a generic dual-reporter gene assay for screening G-protein-coupled receptors." Journal of Biomolecular Screening, vol. 10, No. 5, 2005, pp. 437-446.
Kotarsky et al., "Progress in methodology. Improved reporter gene assays used to identify ligands acting on orphan seven-transmembrane receptors." Pharmacology & toxicology, vol. 93, No. 6, Sep. 27, 2003, pp. 249-258.
Liu et al., "Comparison on functional assays for Gq-coupled GPCRs by measuring inositol monophospate-1 and intracellular calcium in 1536-well plate format." Current Chemical Genomics, vol. 1, 2008, pp. 70-78.
Manning, "Measures of efficacy using G proteins as endpoints: differential engagement of G proteins through single receptors2." Molecular Pharmacology, vol. 62, No. 3, 2002, pp. 451-452.
Mountjoy et al., "Melanocortin receptor-mediated mobilization of intracellular free calcium in HEK293 cells." Physiological Genomics, vol. 5, No. 1, 2001, pp. 11-19.
Newman et al., "Activation of the melanocortin-4 receptor mobilizes intracellular free calcium in immortalized hypothalamic neurons." Journal of Surgical Research, vol. 132, No. 2, May 15, 2006, pp. 201-207.
Nickolls et al., "Functional selectivity of melanocortin 4 receptor peptide and nonpeptide agonists: evidence for ligand-specific conformational states." Journal of Pharmacology and Experimental Therapeutics, vol. 313, No. 3, 2005, pp. 1281-1288.
Nøhr et al., "The orphan G protein-coupled receptor GPR139 is activated by the peptides: adrenocorticotropic hormone (ACTH), α-, and β-melanocyte stimulating hormone (α-MSH, and β-MSH), and the conserved core motif HFRW." Neurochemistry International, vol. 102, 2017, pp. 105-113.
Van Der Westhuizen et al., "Quantification of ligand bias for clinically relevant β2-adrenergic receptor ligands: implications for drug taxonomy." Molecular Pharmacology, vol. 85, No. 3, Mar. 2014, pp. 492-509.
Cheng et al., "Relationship between the inhibition constant (K1) and the concentration of inhibitor which causes 50 per cent inhibition (I50) of an enzymatic reaction." Biochemical Pharmacology, vol. 22, No. 23, Dec. 1, 1973, pp. 3099-3108.
Zhao et al., "Biased signaling of protease-activated receptors." Frontiers in Endocrinology, vol. 5, No. 67, May 13, 2014,17 pages.
Extended European Search Report mailed May 7, 2024 in corresponding European Patent Application No. 21750583.3.
Zaretsky, S., & Yudin, A. K. (2017). Recent advances in the synthesis of cyclic pseudopeptides. In Drug Discovery Today: Technologies (2017, vol. 26, pp. 3-10). Elsevier Ltd. https://doi.org/10.1016/j.ddtec.2017.11.004.

* cited by examiner

DIAMINE-LINKED MELANOCORTIN RECEPTOR-SPECIFIC CYCLIC PEPTIDES FOR OCULAR INDICATIONS

CROSS-REFERENCE TO RELATED APPLICATIONS

This application is a continuation of International Application No. PCT/US2021/016007, entitled “Diamine-Linked Receptor-Specific Cyclic Peptides”, and filed on Feb. 1, 2021, which in turn claimed priority to and the benefit of the filing of U.S. provisional patent application No. 62/969,311, entitled “Diamine-Linked Receptor-Specific Cyclic Peptides”, and filed on Feb. 3, 2020, and to U.S. provisional patent application No. 63/124,927, entitled “Diamine-Linked Receptor-Specific Cyclic Peptides”, and filed on Dec. 14, 2020, and the specification and claims of each of the foregoing patent applications are incorporated herein by reference.

REFERENCE TO THE SEQUENCE LISTING

The Sequence Listing submitted Jan. 7, 2026 as an XML file named “01-3664-US-4_SL.xml”, created on Dec. 19, 2025 and having a size of 159,062 bytes is hereby incorporated by reference pursuant to 37 C.F.R. § 1.52(e)(5).

BACKGROUND OF THE INVENTION

Field of the Invention (Technical Field)

The present invention relates to side chain-to-tail diamine-linked cyclic peptides, including receptor-specific peptides that are agonists, partial agonists, antagonists, or mixed agonist-antagonists at melanocortin receptors, and the use of melanocortin receptor-specific diamine-linked cyclic peptides in the treatment of melanocortin receptor-mediated diseases, indications, conditions and syndromes.

DESCRIPTION OF RELATED ART

Peptides have been cyclized through the side chains of two amino acid residues, one proximal the N-terminus and the other proximal the C-terminus of the peptide sequence, typically through disulfide bonds (e.g., through the side chains of two Cys residues) or amide bonds (e.g., through the side chains of two residues, one with a side chain including a carboxyl group and one with a side chain including an amine). Head-to-tail cyclized peptides are also known, such as peptides wherein an amide is formed by coupling the N-terminus group (e.g., an amine) and the C-terminus group (e.g., a carboxylic acid), thereby forming an amide-linked cyclic peptide.

A family of melanocortin receptor types and subtypes have been identified, including melanocortin receptor-1 (MC1r) expressed on normal human melanocytes, melanoma cells, macrophages and other cells; melanocortin receptor-2 (MC2r) for ACTH (adrenocorticotropin), expressed in cells of the adrenal gland; melanocortin receptor-3 and melanocortin receptor-4 (MC3r and MC4r), expressed in cells in the hypothalamus, mid-brain, brainstem and in peripheral tissues; and melanocortin receptor-5 (MC5r), expressed in a wide distribution of peripheral tissues. MC1r is believed to be associated with mediation of inflammation, hair and skin pigmentation, and other functions; MC2r is believed to mediate steroidogenesis; MC3r is believed to be associated with energy homeostasis, feeding behavior, mediation of inflammation, and other functions; MC4r is believed to be associated with feeding behavior, energy homeostasis, sexual functioning, and other functions; and MC5r is believed to be associated with exocrine gland system regulation and other functions.

Both agonist and antagonist melanocortin receptor-specific compounds are known, including agonist and antagonist peptides. For example, MC4r agonist peptides are believed to have utility for treatment of obesity or inducing weight loss, and for treatment of various forms of sexual dysfunction, including male erectile dysfunction and female sexual dysfunction. MC4r antagonist peptides are believed to result in weight gain, with potential utility for conditions such as cachexia and other wasting syndromes and conditions.

Peptide analogs of the endogenous agonist alpha-melanocortin stimulating hormone (α-MSH) are known. These include both linear and cyclic peptides. Cyclic melanocortin receptor-specific peptides are typically cyclized through side chains, such as amide or cysteine linkages, and acylated at the N-terminus and amidated at the C-terminus (endogenous α-MSH is acylated at the N-terminus and amidated at the C-terminus), but it is known that α-MSH analogs may have a C-terminus carboxyl group, as disclosed in U.S. Pat. No. 6,579,968.

Notwithstanding the intense scientific and pharmaceutical interest in melanocortin receptor-specific peptides, evidenced by numerous articles in the scientific literature and numerous patent applications and issued patents, the only melanocortin receptor-specific peptide drugs approved in the United States are bremelanotide, sold under the tradename VYLEESI®, indicated for hypoactive sexual desire disorder in premenopausal women, afamelanotide, sold under the tradename SCENESSE®, indicated for the prevention of phototoxicity in adult patients with erythropoietic protoporphyria, and setmelanotide, sold under the tradename IMCIVREE®, indicated for treatment of obesity due to proopiomelanocortin (POMC), proprotein convertase subtilisin/kexin type 1 (PCSK1), or leptin receptor (LEPR) deficiency. There remains a significant and substantial need for melanocortin receptor-specific peptides for use in pharmaceutical applications, particularly in treatment of inflammation-related diseases, indications, conditions and syndromes. It is against this background that the present invention was made.

BRIEF SUMMARY OF THE INVENTION

In one aspect, the present invention relates to a side chain-to-tail diamine-linked cyclized peptide of formula I:

(I)

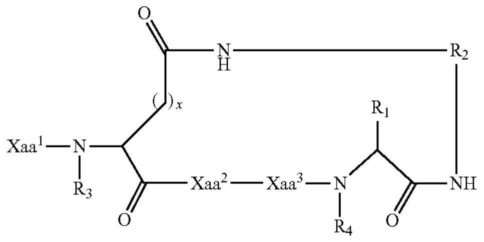

including all enantiomers, stereoisomers or diastereomers thereof, or a pharmaceutically acceptable salt of any of the foregoing, wherein:

$Xaa^1$ is $—R_5$-$R_6$;

$Xaa^2$ and $Xaa^3$ are each independently from one to three L- or D-isomer amino acids, or a combination thereof, linked by backbone amide bonds, wherein any backbone nitrogen atom is optionally alkylated with a $C_1$ to $C_3$ linear or branched alkyl, and if optionally alkylated, the alkyl optionally forms a ring with the side chain of the same amino acid if said side chain is aliphatic, wherein the ring is optionally substituted;

$R_1$ is H or an L- or D-isomer amino acid side chain;

$R_2$ is $—(CH_2)_u—$ or $—(CH_2)_v—O—(CH_2)_w—$;

$R_3$ is H or a $C_1$ to $C_9$ linear or branched aliphatic chain, optionally comprising one or more C═C double bonds;

$R_4$ is —H or a $C_1$ to $C_3$ linear or branched alkyl;

$R_5$ is optionally present, and if present, is from one to three L- or D-isomer amino acids, or a combination thereof, linked by backbone amide bonds, wherein any backbone nitrogen atom is optionally methylated;

$R_6$ is H or a $C_1$ to $C_{17}$ acyl group comprising optionally substituted linear or branched alkyl, cycloalkyl, alkylcycloalkyl, aryl, aralkyl or heteroaryl;

x is from 1 to 5;

u is from 2 to 8;

v is from 2 to 5; and w is from 2 to 5.

In the peptide of formula I $Xaa^2$-$Xaa^3$ may comprise the amino acid sequence -D-Phe-Arg- or -Phe-Arg- wherein the phenyl ring of D-Phe or Phe is optionally substituted. Alternatively, $Xaa^2$-$Xaa^3$ may comprise, or may consist of, the amino acid sequence -His-D-Phe-Arg- or -His-Phe-Arg- wherein the phenyl ring of D-Phe or Phe is optionally substituted and $R_1$ is a side chain of the L- or D-isomer amino acid Trp.

In another aspect, $R_1$ may be a side chain of the L- or D-isomer amino acid Trp.

In yet another aspect, $Xaa^2$-$Xaa^3$ may comprise the amino acid sequence -His-D-Phe- or -His-Phe- wherein the phenyl ring of D-Phe or Phe is optionally substituted and $R_1$ is a side chain of the L- or D-isomer amino acid Arg.

In yet another aspect of the peptide of formula I, wherein $R_5$ may be an L- or D-isomer of Ne or Arg. In this aspect, $Xaa^2$-$Xaa^3$ may comprise the amino acid sequence -D-Phe-Arg- or -Phe-Arg- wherein the phenyl ring of D-Phe or Phe is optionally substituted. Alternatively, in this aspect, $Xaa^2$-$Xaa^3$ may comprise the amino acid sequence -D-Phe-Arg- or -Phe-Arg- wherein the phenyl ring of D-Phe or Phe is optionally substituted and $R_1$ is a side chain of the L- or D-isomer amino acid Trp.

In another aspect of the peptide of formula I, $R_3$ is not present and $R_4$ is a $C_1$ to $C_{17}$ acyl group. In this aspect, $Xaa^2$-$Xaa^3$ may comprises the amino acid sequence -D-Phe-Arg- or -Phe-Arg- wherein the phenyl ring of D-Phe or Phe is optionally substituted. Alternatively, $Xaa^2$-$Xaa^3$ may comprise the amino acid sequence -D-Phe-Arg- or -Phe-Arg- wherein the phenyl ring of D-Phe or Phe is optionally substituted and $R_1$ is a side chain of the L- or D-isomer amino acid Trp.

In another aspect of the peptide of formula I, $R_5$ is an L- or D-isomer of Ne or Arg and $R_6$ is a $C_1$ to $C_{17}$ acyl group. In this aspect, $Xaa^2$ and $Xaa^3$ comprise the amino acid sequence -D-Phe-Arg- or -Phe-Arg- wherein the phenyl ring of D-Phe or Phe is optionally substituted. Alternatively, $Xaa^2$ and $Xaa^3$ may comprise the amino acid sequence -D-Phe-Arg- or -Phe-Arg- wherein the phenyl ring of D-Phe or Phe is optimally substituted and $R_1$ is a side chain of the L- or D-isomer amino acid Trp.

In another aspect, wherein the phenyl ring of D-Phe or Phe is optionally substituted, it is optionally substituted with between one and three ring substituents wherein the substituents are the same or different, and each independently comprise halo, ($C_1$-$C_{10}$)alkyl-halo, ($C_1$-$C_{10}$)alkyl, ($C_1$-$C_{10}$) alkoxy, ($C_1$-$C_{10}$)alkylthio, aryl, ($C_1$-$C_{10}$)alkylaryl, aryloxy, nitro, nitrile, sulfonamide, amino, monosubstituted amino, disubstituted amino, hydroxy, carbamoyl, carboxy, carbamoyl, alkoxy-carbonyl, or aryloxy-carbonyl.

In the peptide of formula I, the L- or D-isomer amino acids may consist of alpha amino acids, beta amino acids, gamma amino acids or delta amino acids, or a combination thereof.

There is further provided the peptide of formula I which is a peptide of formula II:

(II)

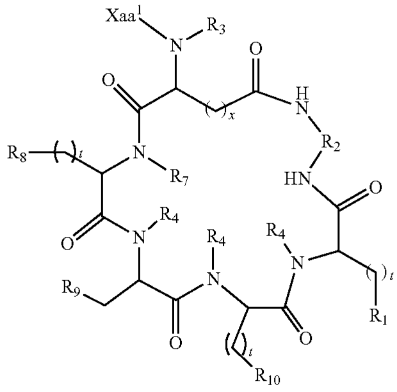

including all enantiomers, stereoisomers or diastereomers thereof, or a pharmaceutically acceptable salt of any of the foregoing, wherein:

$Xaa^1$ is $—R_5$-$R_6$;

$R_1$ is substituted or unsubstituted indole, phenyl or naphthyl;

$R_2$ is $—(CH_2)_u—$ or $—(CH_2)_v—O—(CH_2)_w—$;

$R_3$ is H or a $C_1$ to $C_9$ linear or branched aliphatic chain, optionally comprising one or more C═C double bonds;

$R_4$ is —H or $—CH_3$, $R_5$ is optionally present, and if present, is from one to three L- or D-isomer amino acids, or a combination thereof, wherein any backbone nitrogen atom is optionally methylated;

$R_6$ is H or a $C_1$ to $C_{17}$ acyl group comprising optionally substituted linear or branched alkyl, cycloalkyl, alkylcycloalkyl, aryl, aralkyl or heteroaryl;

$R_7$ is —H, $—CH_3$ or $—CH_2—$, and if it is $—CH_2—$ forms with $R_8$ a ring of the general structure

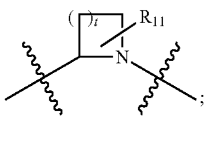

;

$R_8$ is —H if $R_8$ forms the ring with $R_7$, or $R_8$ is
—$(CH_2)_3$,
—$N(R_{12a})(R_{12b})$,
—NH—$(CH_2)_z$—$N(R_{12a})(R_{12b})$,
—C(=O)—$N(R_{12a})(R_{12b})$,
—O—$(R_{12a})$,
—S—$(=O)_2$—$CH_3$,
—S—(=O)—$CH_3$,
substituted or unsubstituted phenyl,
—O—$CH_2$-phenyl, where phenyl is substituted or unsubstituted,

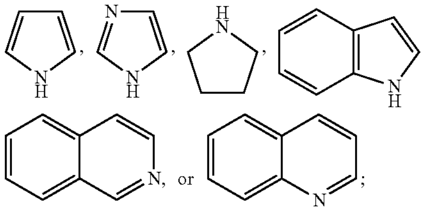

$R_9$ is substituted or unsubstituted phenyl or naphthyl;
$R_{10}$ is
—$N(R_{12a})(R_{12b})$,
—NH—$(CH_2)_z$—$N(R_{12a})(R_{12b})$,
—NH—C(=NH)—$N(R_{12a})(R_{12b})$,
—NH—C(=O)—$N(R_{12a})(R_{12b})$,
—$O(R_{12a})$,
—$C_1$ to $C_{17}$ linear, branched or cyclic alkyl chain,
—$S(=O)_2$—$CH_3$,
—S(=O)—$CH_3$,
—C(=O)—$O(R_{12a})$,

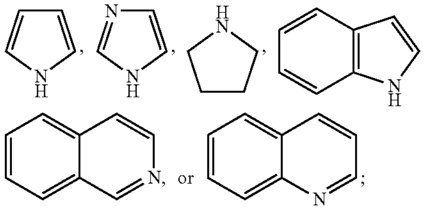

$R_{11}$ is —O—$CH_2$-phenyl, where phenyl is substituted or unsubstituted;
$R_{12a}$ and $R_{12b}$ are each independently and independently in each instance H or a $C_1$ to $C_4$ linear, branched or cyclic alkyl chain;
t is in each instance independently from 1 to 4;
x is from 1 to 5;
u is from 2 to 8;
v and w are each independently from 2 to 5; and
z is from 1 to 3.

In the peptide of formula II, $R_9$ may be unsubstituted naphthyl.

In another aspect, in the peptide of formula II, any substituted phenyl or naphthyl may be in each instance independently substituted with between one and three ring substituents wherein the substituents are the same or different, and are each independently halo, $(C_1\text{-}C_{10})$alkyl-halo, $(C_1\text{-}C_{10})$alkyl, $(C_1\text{-}C_{10})$alkoxy, $(C_1\text{-}C_{10})$alkylthio, aryl, $(C_1\text{-}C_{10})$alkylaryl, aryloxy, nitro, nitrile, sulfonamide, amino, monosubstituted amino, disubstituted amino, hydroxy, carbamoyl, carboxy, carbamoyl, alkoxy-carbonyl, or aryloxy-carbonyl.

In another aspect of the peptide of formula II, $R_5$ comprises at least one L- or D-isomer amino acid, which may be a single L- or D-isomer amino acid with an aliphatic side chain, including wherein the aliphatic side chain is —$(CH_2)_3$—$CH_3$. Alternatively, in the peptide of formula II $R_5$ may be a single L- or D-isomer amino acid with a side chain comprising at least one nitrogen atom, including but not limited to where $R_5$ is an L- or D-isomer of Arg, Lys, Orn, Dab, Dap or Cit.

In another aspect of the peptide of formula II, the peptide may be of the formula:

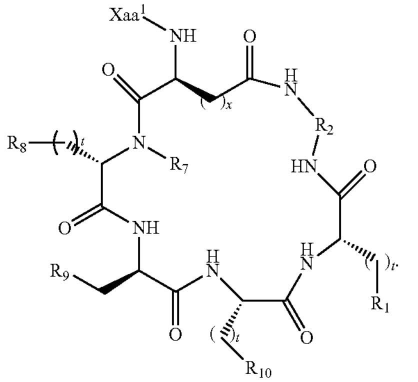

In any of the embodiments of the peptide of formula II, Xaa[1] may be Ac-Arg, Ac-D-Arg, Ac-Nle, Ac-D-Nle, Ac-Trp, cyclopentyl acetyl, hexanoyl, 3-phenylpropanoyl, cyclopentylacetyl, acetyl, 2-naphthylacetyl, or 3-(1-naphthyl)propanoyl; $R_1$ may be indole or naphthalene; $R_7$ and $R_8$ may together comprise pyrrolidine, including wherein pyrrolidine is substituted, including but not limited to wherein the substituent is —O—$CH_2$-phenyl, where phenyl is substituted or unsubstituted; $R_9$ may be substituted phenyl.

In an alternative aspect, the peptide of formula I may be a peptide of formula III:

(III)

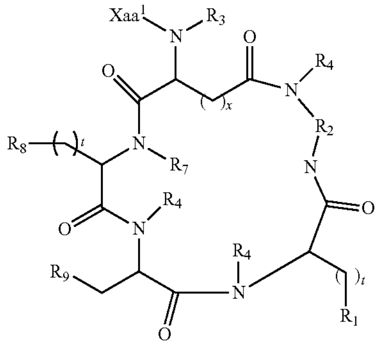

including all enantiomers, stereoisomers or diastereomers thereof, or a pharmaceutically acceptable salt of any of the foregoing,
wherein:
Xaa[1] is —$R_5$-$R_6$;
$R_1$ is
—$N(R_{12a})(R_{12b})$,
—NH—$(CH_2)_z$—$N(R_{12a})(R_{12b})$,
—NH—C(=NH)—$N(R_{12a})(R_{12b})$,
—NH—C(=O)—$N(R_{12a})(R_{12b})$, —O($R_{12a}$),
—$C_1$ to $C_{17}$ linear, branched or cyclic alkyl chain,
—S(=O)$_2$—$CH_3$,
—S(=O)—$CH_3$,
—C(=O)—O($R_{12a}$),

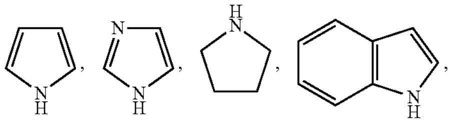

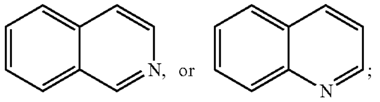

$R_2$ is —$(CH_2)_u$— or —$(CH_2)_v$—O—$(CH_2)_w$—;

$R_3$ is H or a $C_1$ to $C_9$ linear or branched aliphatic chain, optionally comprising one or more C=C double bonds;

$R_4$ is —H or —$CH_3$, $R_5$ is optionally present, and if present, is from one to three L- or D-isomer amino acids, or a combination thereof, wherein any backbone nitrogen atom is optionally methylated;

$R_6$ is H or a $C_1$ to $C_{17}$ acyl group comprising optionally substituted linear or branched alkyl, cycloalkyl, alkylcycloalkyl, aryl, aralkyl or heteroaryl;

$R_7$ is —H, —$CH_3$ or —$CH_2$—, and if it is —$CH_2$— forms with $R_8$ a ring of the general structure

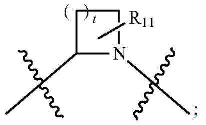

$R_8$ is —H if $R_3$ forms the ring with $R_7$, or $R_8$ is
—H,
—$(CH_2)_3$,
—N($R_{12a}$)($R_{12b}$),
—NH—$(CH_2)_z$—N($R_{12a}$)($R_{12b}$),
—C(=O)—N($R_{12a}$)($R_{12b}$),
—O—($R_{12a}$),
—S—(=O)$_2$—$R_{12a}$,
substituted or unsubstituted phenyl,
—O—$CH_2$-phenyl, where phenyl is substituted or unsubstituted,

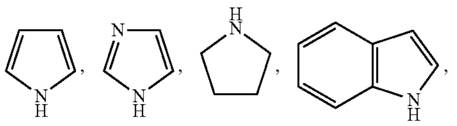

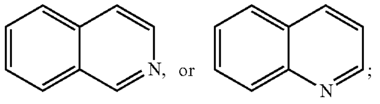

$R_9$ is substituted or unsubstituted phenyl or naphthyl;

$R_{11}$ is —O—$CH_2$-phenyl, where phenyl is substituted or unsubstituted;

$R_{12a}$ and $R_{12b}$ are each independently and independently in each instance H or a $C_1$ to $C_4$ linear, branched or cyclic alkyl chain;

t is in each instance independently from 1 to 4;
x is from 1 to 5;
u is from 2 to 8;
v and 2 are each independently 2 to 5; and
z is from 1 to 3.

In one aspect of the cyclic peptide of formula III, $R_9$ is unsubstituted naphthyl. In another aspect of the peptide of formula III, any substituted phenyl or naphthyl may in each instance independently be substituted with between one and three ring substituents wherein the substituents are the same or different, and are each independently halo, ($C_1$-$C_{10}$)alkylhalo, ($C_1$-$C_{10}$)alkyl, ($C_1$-$C_{10}$)alkoxy, ($C_1$-$C_{10}$)alkylthio, aryl, ($C_1$-$C_{10}$)alkylaryl, aryloxy, nitro, nitrile, sulfonamide, amino, monosubstituted amino, disubstituted amino, hydroxy, carbamoyl, carboxy, carbamoyl, alkoxy-carbonyl, or aryloxy-carbonyl.

In another aspect of the peptide of formula III, $R_5$ may comprise at least one L- or D-isomer amino acid, which may be a single L- or D-isomer amino acid with an aliphatic side chain.

In another aspect of the peptide of formula III, $R_6$ may be acetyl, cyclopentyl acetyl, hexanoyl, 3-phenylpropanoyl, cyclopentylacetyl, 2-naphthylacetyl, or 3-(1-naphthyl)propanoyl.

In another aspect of the peptide of formula III, the peptide is a cyclic peptide of the formula:

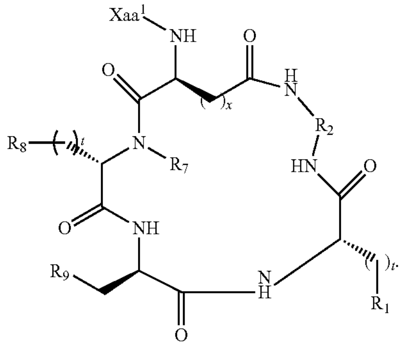

In another embodiment, the invention provides a cyclic peptide of formula IV or V:

(IV)

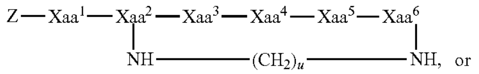

or (V)

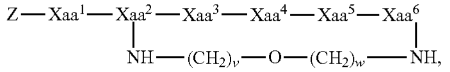

or a pharmaceutically acceptable salt thereof, wherein

Z is H or an N-terminal group;

$Xaa^1$ is optionally present, and if present is from one to three amino acids, wherein any backbone nitrogen atom is optionally methylated;

$Xaa^2$ is an L- or D-isomer of an amino acid with a side chain comprising a carboxyl group forming an amide bond with a first —NH— of the group —NH—$(CH_2)_u$—NH— or —NH—$(CH_2)_v$—O—$(CH_2)_w$—NH—;

$Xaa^3$ is an L- or D-isomer amino acid of Pro, optionally substituted with hydroxyl, halogen, sulfonamide, alkyl, —O-alkyl, aryl, alkyl-aryl, alkyl-O-aryl, alkyl-O-alkyl-aryl, —O-alkyl-aryl, or —O-aryl, or $Xaa^3$ is an L- or D-isomer amino acid with a side chain comprising at least one primary amine, secondary amine, alkyl, cycloalkyl, cycloheteroalkyl, aryl, heteroaryl, ether, sulfide, or carboxyl;

$Xaa^4$ is an L- or D-isomer amino acid with a side chain comprising substituted or unsubstituted aryl;

$Xaa^5$ is an L- or D-isomer amino acid with a side chain comprising at least one primary amine, secondary amine, guanidine, urea, alkyl, cycloalkyl, cycloheteroalkyl, aryl, heteroaryl, or ether, and if $Xaa^6$ is not present, with a C-terminal carboxyl group forming an amide bond with a second —NH— of the group $—NH—(CH_2)_u—NH—$ or $—NH—(CH_2)_v—O—(CH_2)_w—NH—$;

$Xaa^6$ is optionally present, and if present is an L- or D-isomer amino acid with a side chain comprising at least one aryl or heteroaryl, optionally substituted with one or more ring substituents, and when one or more are present, are the same or different and independently hydroxyl, halogen, sulfonamide, alkyl, —O-alkyl, aryl, or —O-aryl, and with a C-terminal carboxyl group forming an amide bond with a second —NH— of the group $—NH—(CH_2)_u—NH—$ or $—NH—(CH_2)_v—O—(CH_2)_w—NH—$;

u is from 2 to 8; and v and w are each independently from 2 to 5;

wherein the groups $—NH—(CH_2)_u—NH—$ and $—NH—(CH_2)_v—O—(CH_2)_w—NH—$ each comprise a first —NH— and a second —NH—.

In the cyclic peptide of formula IV or V, Z may be an N-terminal group selected from the group consisting of a $C_1$ to $C_{17}$ acyl group comprising a linear or branched alkyl, cycloalkyl, alkyl cycloalkyl, aryl or aralkyl.

In the cyclic peptide of formula IV or V, $Xaa^1$ may be a single amino acid residue selected from the group consisting of Gly or an L- or D-isomer of Ala, Nle, Leu, Ile or Val. Alternatively, $Xaa^1$ may be a single amino acid with a side chain including at least one primary amine, guanidine or urea group, including but not limited to an L- or D-isomer of Arg, Lys, Orn, Dab, Dap or Cit.

In the cyclic peptide of formula IV or V, $Xaa^4$ may be D-Phe or Phe, optionally substituted with from one to three ring substituents. The ring substituents may be the same or different, and are each independently halo, $(C_1\text{-}C_{10})$alkyl-halo, $(C_1\text{-}C_{10})$alkyl, $(C_1\text{-}C_{10})$alkoxy, $(C_1\text{-}C_{10})$alkylthio, aryl, $(C_1\text{-}C_{10})$alkylaryl, aryloxy, nitro, nitrile, sulfonamide, amino, monosubstituted amino, disubstituted amino, hydroxy, carboxy, or alkoxy-carbonyl. Alternatively, $Xaa^4$ may be D-Nal 1 or D-Nal 2.

In the cyclic peptide of formula IV or V, $Xaa^5$ may be an L- or D-isomer of of Arg, Lys, Orn, Dab or Dap, and $Xaa^6$ may be an L- or D-isomer of Trp, Nal 1 or Nal 2.

The cyclic peptide of formula IV or V thus includes, but is not limited to, the following substitutions where:

Z is a $C_1$ to $C_7$ linear alkyl acyl group;

$Xaa^1$ is an L- or D-isomer of Ne or Arg;

$Xaa^2$ is an L- or D-isomer of Asp or Glu wherein the side chain carboxyl group forms an amide bond with a first —NH— of the group $—NH—(CH_2)_u—NH—$ or $—NH—(CH_2)_v—O—(CH_2)_w—NH—$;

$Xaa^3$ is an L- or D-isomer of His, Hyp(Bzl), $Met(O_2)$, or Asn;

$Xaa^4$ is an L- or D-isomer of substituted or unsubstituted Phe, Nal 1 or Nal 2;

$Xaa^5$ is an L- or D-isomer of Arg; and $Xaa^6$ is an L- or D-isomer of Trp, Nal 1 or Nal 2, wherein the C-terminal carboxyl group thereof forms an amide bond with a second —NH— of the group $—NH—(CH_2)_u—NH—$ or $—NH—(CH_2)_v—O—(CH_2)_w—NH—$.

There is further provided an embodiment of the cyclic peptide of formula IV, wherein the side chain carboxyl group of $Xaa^2$ forms an amide bond with a first —NH— of the group $—NH—(CH_2)_u—NH$ and the C-terminal carboxyl group of $Xaa^6$ forms an amide bond with a second —NH— of the group $—NH—(CH_2)_u—NH—$.

In another aspect of the cyclic peptide of formula IV or V at least one backbone nitrogen atom thereof may comprise a methyl group. In an alternative aspect, no backbone nitrogen atom thereof comprises a methyl group.

In another embodiment, there is provided a cyclic peptide having the structure (SEQ ID NO: 51):

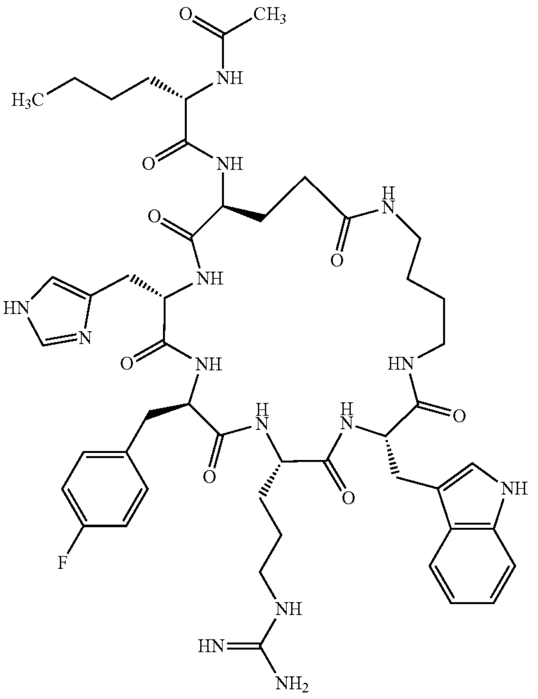 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O]

or a pharmaceutically acceptable salt thereof.

In the foregoing cyclic peptide, the pharmaceutically acceptable salt may be an acetate salt or alternatively may be a trifluoroacetate salt.

In another embodiment, there is provided a cyclic peptide which is:

(SEQ ID NO: 1)

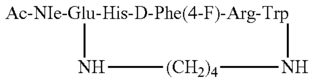

or a pharmaceutically acceptable salt thereof.

There is further provided a pharmaceutical composition comprising the cyclic peptides as set forth above, or a pharmaceutically acceptable salt thereof, and a pharmaceutically acceptable carrier.

The invention further includes a method for treatment of a melanocortin receptor-mediated disease, indication, condition or syndrome in a human or non-human mammal, comprising the step of administering pharmaceutical composition comprising one or more of the cyclic peptides as set forth above. The invention further includes a method for treating a condition responsive to changes in melanocortin receptor function in a human or non-human mammal, comprising the step of administering a pharmaceutical composition comprising the one or more of the cyclic peptides as set forth above. In the method for treating, the melanocortin receptor-mediated disease, indication, condition or syndrome in a human may be ocular inflammation, and the pharmaceutical composition may be an aqueous pharmaceutical composition for administration to the surface of the eye.

The ocular inflammation responses to changes in melanocortin receptor function may be caused by an ocular condition, wherein the ocular condition is dry eye disease, corneal ulcer, corneal erosion, corneal abrasion, corneal degeneration, corneal perforation, corneal scarring, epithelial defect, keratoconjunctivitis, idiopathic uveitis, corneal transplantation, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, pterygium, a wound sustained to ocular surface, post-photorefractive keratotomy eye pain and inflammation, thermal or chemical burn to the cornea, scleral wound, keratoconus or conjunctival wound. In one aspect, the inflammation is caused by dry eye disease or keratoconjunctivitis sicca.

In one embodiment, there is provided a pharmaceutical composition for ocular administration wherein the pharmaceutically acceptable carrier is an aqueous solution comprising about 2.79 mg/mL of trisodium citrate dihydrate, about 9 mg/mL of sodium chloride and about 1 mg/mL of polysorbate 80. In the pharmaceutical composition the cyclic peptide may be in a trifluoroacetic acid salt form at a concentration of about 1.0 μg/mL. The pharmaceutical composition may further comprise about 0.10 mg/mL anhydrous citric acid. The pharmaceutical composition aqueous solution is at about pH 6.5, and the composition further comprises sodium hydroxide or hydrochloric acid as needed to adjust pH. In a further aspect, the invention provides a method of treating dry eye disease or keratoconjunctivitis sicca comprising administering no more than about 50 μL of the pharmaceutical composition no more often than about three times per day. Preferably no more than about 150 ng of cyclic peptide or pharmaceutically acceptable salt thereof is administered per eye per day.

In a related aspect, the invention provides a method of treating dry eye disease or keratoconjunctivitis sicca comprising administering to the surface of the eye no more than about 150 ng per day of a melanocortin receptor-specific peptide with an $EC_{50}$ value of less than 1 nM at each of MC1r and MC5r per eye in divided doses administered no more than three times per day. The dose administered may be less than 150 ng/eye/day of a peptide of the invention, and may be about 100 ng/eye/day or about 50 ng/eye/day of a peptide of the invention. The peptide is an agonist or partial agonist at each of MC1r and MC5r, with $EC_{50}$ values determined by cAMP production using the HTRF detection method as performed by CEREP. In one aspect, the melanocortin receptor-specific peptide is a cyclic peptide of the structure (SEQ ID NO: 51):

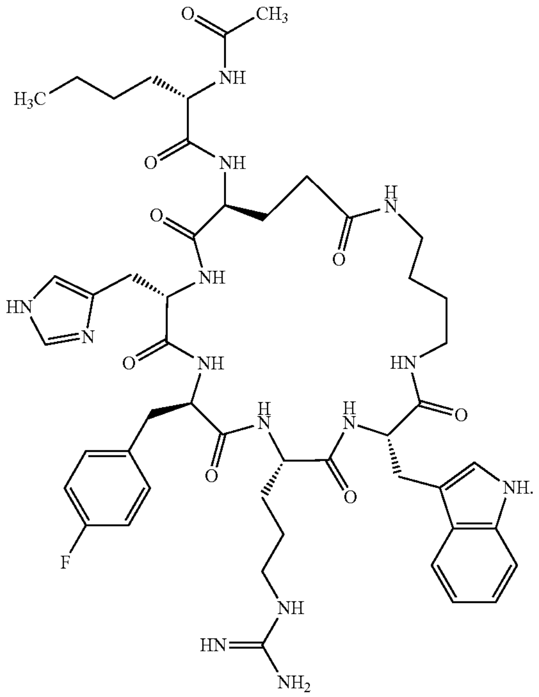 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O]

In one aspect, there is provided a cyclic peptide template which may be utilized in making receptor-specific peptides for biological receptors.

In another aspect, there is provided a melanocortin receptor-specific peptide-based pharmaceutical composition for use in treatment of melanocortin receptor-mediated diseases, indications, conditions and syndromes.

In another aspect, there is provided a peptide-based melanocortin receptor-specific pharmaceutical, wherein the peptide is selective and an agonist for MC1r and is an antagonist at MC4r.

In another aspect, there is provided a peptide-based melanocortin receptor-specific pharmaceutical, wherein the peptide is selective and an agonist for MC1r and is a partial agonist at MC4r.

In another aspect, there is provided a receptor-specific peptide which functionally active at one or more melanocortin receptors at subnanomolar $EC_{50}$ values.

In another aspect, there is provided a melanocortin receptor-specific peptide which is an agonist or partial agonist at MC1 r and MC5r at $EC_{50}$ values of less than 1 nM.

Other aspects and novel features, and the further scope of applicability of the present invention will be set forth in part in the detailed description to follow, and in part will become apparent to those skilled in the art upon examination of the following, or may be learned by practice of the invention. The aspects of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serves to explain the principles of the invention. The drawings are only for the purpose of illustrating one or more preferred embodiments of the invention and are not to be construed as limiting the invention.

DETAILED DESCRIPTION OF THE INVENTION

1.0 Definitions

Figure 1A:
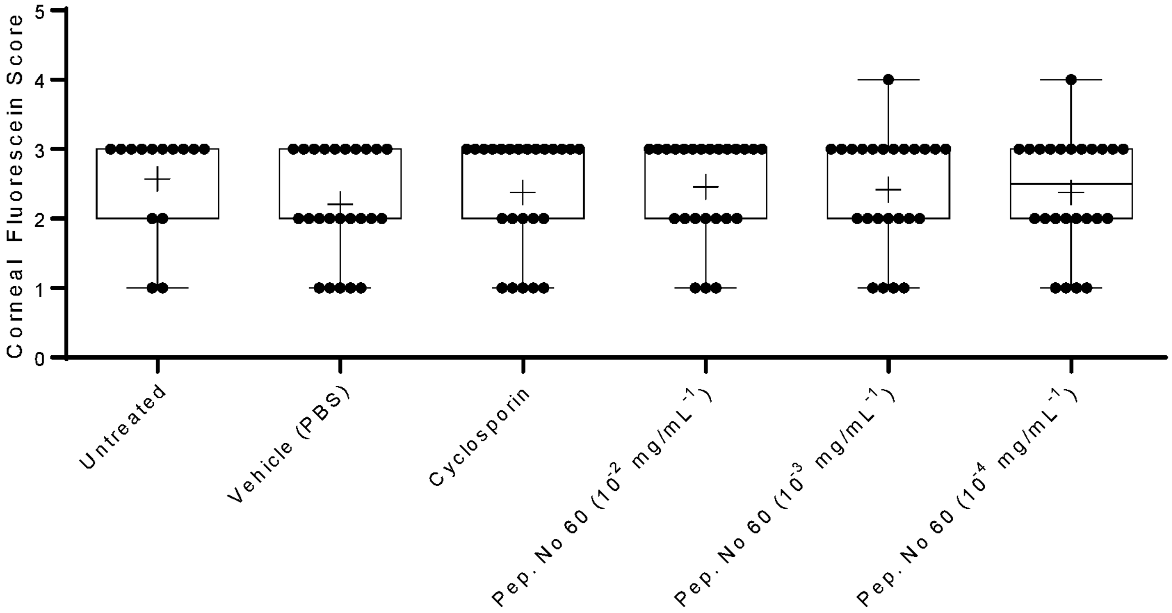
FIG. 1A is a box/whisker plot, indicating the median (line), 25th/75th percentile (box), mean (+) and the (whiskers) of the corneal fluorescein score on day 12, following exposure on day 1 to a controlled desiccating environment with transdermal administration of scopolamine to establish disease prior to any treatment. Individual data points are depicted as filled circles. The number of eyes (n) was 24 per group, except for the untreated group (n=14).

Before proceeding with the description of the invention, certain terms are defined as set forth herein.

In the sequences given for the peptides disclosed herein, the amino acid residues have their conventional meaning as given in Chapter 2400 of the Manual of Patent Examining Procedure, $9^{th}$ Ed. Thus, "Ala" is alanine, "Asn" is asparagine, "Asp" is aspartic acid, "Arg" is arginine, "Cys" is cysteine, "Gly" is glycine, "Gln" is glutamine, "Glu" is glutamic acid, "His" is histidine, "Ile" is isoleucine, "Leu" is leucine, "Lys" is lysine, "Met" is methionine, "Phe" is phenylalanine, "Pro" is proline, "Ser" is serine, "Thr" is Threonine, "Trp" is tryptophan, "Tyr" is tyrosine, "Val" is valine, and so on. It is to be understood that D-isomers are designated by a "D-" before the three-letter code or amino acid name, such that for example D-Phe is D-phenylalanine. Amino acid residues not encompassed by the foregoing include, but are not limited to, those with the following side chains, it being understood that such amino acid residues may be L-isomers or D-isomers:

| Abbreviation | Common Name | Side Chain |
|---|---|---|
| Cit | citrulline | 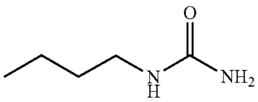 |
| Dab | diaminobutyric acid | 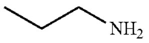 |
| Dap | diaminoproprionic acid | 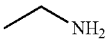 |
| Met($O_2$) | methionine sulfone | 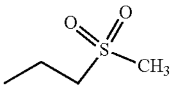 |
| Nal 1 | 3-(1-naphthyl)alanine | 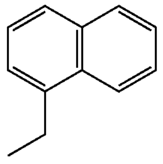 |
| Nal 2 | 3-(2-naphthyl)alanine | 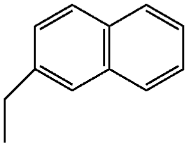 |
| Nle | norleucine | 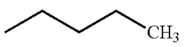 |
| Orn | ornithine | 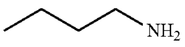 |

-continued
| Abbreviation | Common Name | Side Chain |
|---|---|---|
| Phe(2-$CF_3$) | 2-trifluoromethyl phenylalanine | 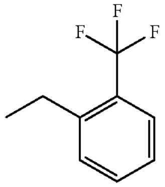 |
| Phe(2-C(=O)—$NH_2$) | 2-carbamoyl-phenylalanine | 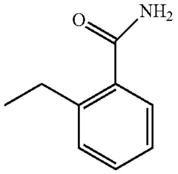 |
| Phe(2-Me) | 2-methyl phenylalanine | 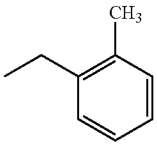 |
| Phe(2-CN) | 2-cyano phenylalanine | 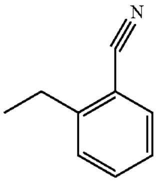 |
| Phe(2-Cl) | 2-chloro phenylalanine | 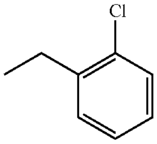 |
| Phe(2,3-diF) | 2,3-difluoro phenylalanine | 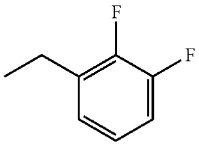 |
| Phe(2,3-diCl) | 2,3-dichloro phenylalanine | 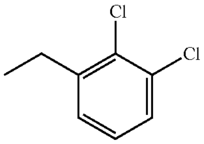 |
| Phe(2,3-diMe) | 2,3-dimethyl phenylalanine | 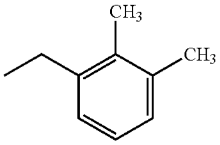 |
| Phe(2,3-diOMe) | 2,3-dimethoxy phenylalanine | 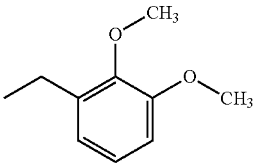 |

-continued

| Abbreviation | Common Name | Side Chain |
|---|---|---|
| Phe(2,4-diCl) | 2,4-dichloro phenylalanine | 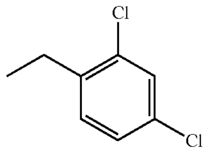 |
| Phe(2-Cl,4-F) | 2-chloro,4-fluoro phenylalanine | 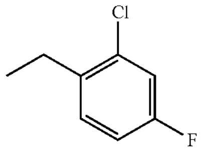 |
| Phe(2,4-diMe) | 2,4-dimethyl phenylalanine | 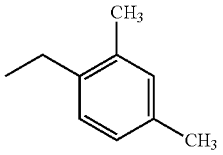 |
| Phe(2-F) | 2-fluoro phenylalanine | 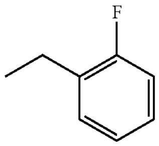 |
| Phe(2,4-diF) | 2,4-difluoro phenylalanine | 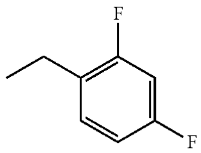 |
| Phe(2-$NO_2$) | 2-nitro phenylalanine | 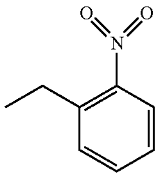 |
| Phe(3-$CF_3$) | 3-trifluoromethyl phenylalanine | 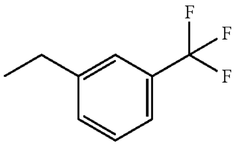 |
| Phe(3-C(═O)—$NH_2$) | 3-carbamoyl-phenylalanine | 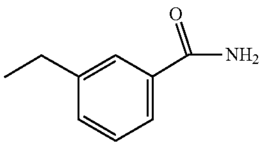 |
| Phe(3-CN) | 3-cyano phenylalanine | 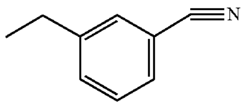 |
| Phe(3-Cl) | 3-chloro phenylalanine | 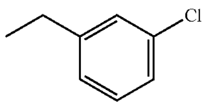 |

-continued

| Abbreviation | Common Name | Side Chain |
|---|---|---|
| Phe(3,4-diCl) | 3,4-dichloro phenylalanine | 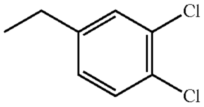 |
| Phe(3-F) | 3-fluoro phenylalanine | 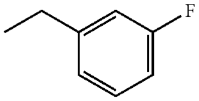 |
| Phe(3,4,5-triF) | 3,4,5-trifluoro phenylalanine | 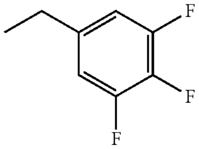 |
| Phe(3,4-diF) | 3,4-difluoro phenylalanine | 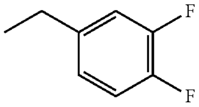 |
| Phe(3,5-diF) | 3,5-difluoro phenylalanine | 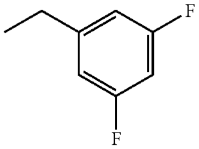 |
| Phe(3-Me) | 3-methyl phenylalanine | 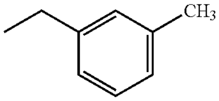 |
| Phe(3-$NO_2$) | 3-nitro phenylalanine | 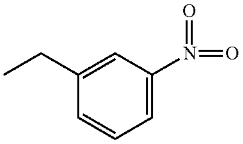 |
| Phe(3-OMe) | 3-methoxy phenylalanine | 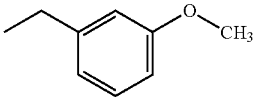 |
| Phe(3,4-diOMe) | 3,4-dimethoxy phenylalanine | 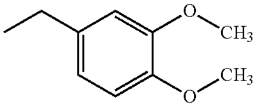 |
| Phe(3-Ph) | 3-phenyl phenylalanine | 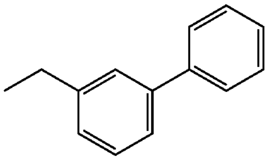 |
| Phe(4-C(=O)—$NH_2$) | 4-carbamoyl-phenylalanine | 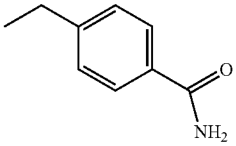 |

-continued

| Abbreviation | Common Name | Side Chain |
|---|---|---|
| Phe(4-Me) | 4-methyl phenylalanine | 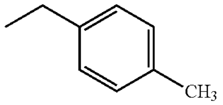 |
| Phe(4-$CF_3$) | 4-trifluoromethyl phenylalanine | 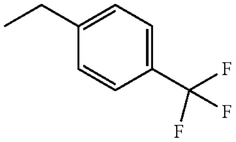 |
| Phe(4-CN) | 4-cyano phenylalanine | 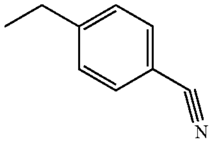 |
| Phe(4-Cl) | 4-chloro phenylalanine | 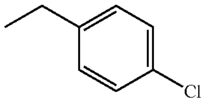 |
| Phe(4-F) | 4-fluoro phenylalanine | 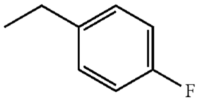 |
| Phe(4-$NH_2$) | 4-amino phenylalanine | 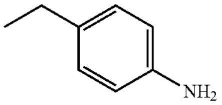 |
| Phe(4-$NO_2$) | 4-nitro phenylalanine | 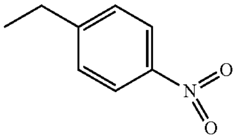 |
| Phe(4-Ph) | 4-phenyl phenylalanine | 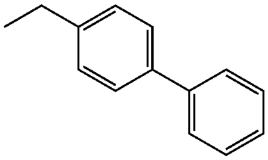 |
| Phe(4-OMe) | 4-methoxy phenylalanine | 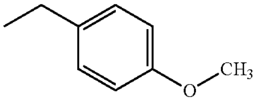 |
| Phe(4-tBu) | 4-tert butyl phenylalanine | 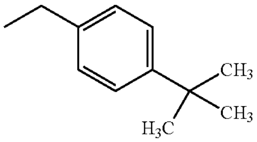 |
| Ser(Bzl) | O-benzyl-serine | 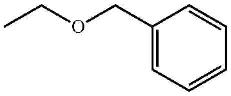 |

Amino acid residues further include, without limitation, the following, it being understood that such amino acid residue may be an L-isomer or D-isomer:

| Abbreviation | Common Name | Amino Acid Structure |
|---|---|---|
| Hyp(Bzl) | O-benzyl-hydroxyproline | 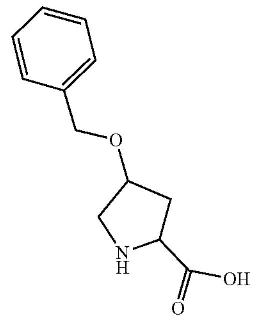 [SMILES: O=C(O)C1CC(OCc2ccccc2)CN1] |

The term "alpha amino acid" includes any amino acid of the general structure

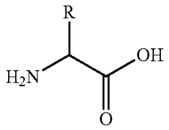

(depicted in its un-ionized form), where R is any side chain group or hydrogen, including without limitation the amino acid residues or side chain groups described in the preceding tables and paragraphs.

The term "L- or D-isomer amino acid" or "L- or D-isomer amino acids" includes any isomeric form of any amino acid residue as defined herein, including specifically any alpha amino acid, beta amino acid, gamma amino acid or delta amino acid, including without limitation an amino acid that is directly coded by DNA, a post-translationally modified amino acid, an amino acid expressed by biological means other than directly by DNA, a proteinogenic or non-proteinogenic amino acid, or any synthetic or manmade amino acid.

Amino acids, including L- or D-isomer amino acids, are joined together by "amide bond" or amide linkages to form a covalent peptide bond linking a backbone carboxylic acid group of one amino acid with a backbone amino group of another amino acid, thereby forming a peptide bond (—C(═O)—NH—) or backbone amide bond.

The term "acyl" includes a group R(C═O)—, where R is an organic group, such as an alkyl, aryl, heteroaryl, carbocyclyl or heterocyclyl. When reference is made herein to a substituted acyl group, it means that said organic group (R) is substituted. Non-limiting examples of acyl groups include $CH_3$—C(═O)—, referred to herein as an acetyl group or "Ac"; $CH_3$—$(CH_2)_4$—C(═O)—, sometimes referred to herein as hexanoyl or "Hex"; $CH_3$—$(CH_2)_5$—C(═O)—, sometimes referred to herein as heptanoyl or "Hept"; and various cyclyl groups, such as phenylpropanoyl and cyclopentylacetyl.

A peptide or aliphatic moiety is "acylated" when an aliphatic or substituted aliphatic group, or an aromatic substituted aromatic group, is bonded through a carbonyl {—(C═O)—}group to form an acyl group. A peptide is most usually acylated at the N terminus.

The term "alkane" includes linear or branched saturated hydrocarbons. Examples of linear alkane groups include methane, ethane, propane, and the like. Examples of branched or substituted alkane groups include methylbutane or dimethylbutane, methylpentane, dimethylpentane or trimethylpentane, and the like. In general, any alkyl group may be a substituent of an alkane.

The term "alkene" includes unsaturated hydrocarbons that contain one or more double carbon-carbon bonds. Examples of such alkene groups include ethylene, propene, and the like.

The term "alkenyl" includes a linear univalent hydrocarbon radical of two to six carbon atoms or a branched univalent hydrocarbon radical of three to six carbon atoms containing at least one double bond; examples thereof include ethenyl, 2-propenyl, and the like.

The "alkyl" groups specified herein include those alkyl radicals of the designated length which are either straight or branched chain saturated aliphatic hydrocarbon groups. $C_{1-10}$ alkyl means an alkyl having from 1 to 10 carbon atoms. Non-limiting examples of such alkyl radicals include methyl, ethyl, propyl, isopropyl, butyl, sec-butyl, tertiary butyl, pentyl, isopentyl, hexyl, isohexyl, and the like.

The term "alkyne" includes a linear monovalent hydrocarbon radical of two to six carbon atoms or a branched monovalent hydrocarbon radical of three to six carbon atoms containing at least one triple bond, examples thereof include ethyne, propyne, butyne, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxycarbonyl. Examples of an aryl group include phenyl, biphenyl, naphthalene, naphthyl, 1-naphthyl, and 2-naphthyl, derivatives thereof, and the like. Similarly, the term "naphthyl" comprises 1-naphthyl and 2-naphthyl, and "naphthalene" comprises 1-naphthaline and 2-naththaline.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkyls, aryls, heteroaryls, alkanes, alkenes, alkynes, and derivatives thereof.

As used herein, the term "amide" includes compounds that have a trivalent nitrogen attached to a carbonyl group, i.e. —C(═O)—$NH_2$ (i.e. primary amide), —C(═O)—$NHR_c$ and —C(═O)—$NR_cR_d$, wherein each of $R_c$ and $R_d$ independently represents hydrogen or an organic group. When reference is made herein to a substituted amide group, it means that at least one of said organic groups ($R_c$ and $R_d$) is substituted. Examples of amides include methylamide, ethylamide, propylamide, and the like.

An "amine" includes an amino group (—$NH_2$), —$NHR_a$ and —$NR_aR_b$, wherein each of $R_a$ and $R_b$ independently represents hydrogen or an organic group. When reference is made herein to a substituted amine group, it means that at least one of the organic groups ($R_a$ and $R_b$) is substituted.

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —$CF_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions encompass any composition made by admixing an active ingredient and one or more pharmaceutically acceptable carriers.

By a melanocortin receptor "agonist" is meant an endogenous substance, drug substance or compound, including certain of the peptide compounds disclosed herein, which can interact with a melanocortin receptor and initiate a pharmacological response, including but not limited to activation of the receptor, including initiating signal transduction, such as adenyl cyclase activation, characteristic of the melanocortin receptor. A melanocortin receptor agonist may be an agonist at one or more of MC1r, MC2r, MC3r, MC4r and MC5r.

By a melanocortin receptor "antagonist" is meant an endogenous substance, drug substance or compound, including certain of the peptide compounds disclosed herein, which blocks or dampens the action of an agonist at a melanocortin receptor. A melanocortin receptor antagonist may be an antagonist at one or more of MC1r, MC2r, MC3r, MC4r and MC5r. Certain compounds, including certain of the peptide compounds disclosed herein, may be an agonist at one or more melanocortin receptors and an antagonist at one or more other melanocortin receptors.

By "α-MSH" is meant the peptide Ac-Ser-Tyr-Ser-Met-Glu-His-Phe-Arg-Trp-Gly-Lys-Pro-Val-$NH_2$ (SEQ ID NO:2) and analogs and homologs thereof, including without limitation NDP-α-MSH.

By "NDP-α-MSH" is meant the peptide Ac-Ser-Tyr-Ser-Nle-Glu-His-D-Phe-Arg-Trp-Gly-Lys-Pro-Val-$NH_2$ (SEQ ID NO:3) and analogs and homologs thereof.

By "$EC_{50}$" is meant the molar concentration of an agonist, including a partial agonist, which produced 50% of the maximum possible response for that agonist. By way of example, a test compound which, at a concentration of 72 nM, produces 50% of the maximum possible response for that compound as determined in a cAMP assay in an MC4r cell expression system has an $EC_{50}$ of 72 nM. Unless otherwise specified, the molar concentration associated with an $EC_{50}$ determination is in nanomoles per liter (nM).

By "Ki (nM)" is meant the equilibrium inhibitor dissociation constant representing the molar concentration of a competing compound that binds to half the binding sites of a receptor at equilibrium in the absence of competitors. In general, the numeric value of the Ki is inversely correlated to the affinity of the compound for the receptor, such that if the Ki is low, the affinity is high. Ki may be determined using the equation of Cheng and Prusoff (Cheng Y., Prusoff W. H., Biochem. Pharmacol. 22: 3099-3108, 1973):

$$Ki = \frac{EC_{50}}{1 + \frac{[\text{ligand}]}{K_D}}.$$

Unless otherwise specified, the molar concentration associated with a Ki determination is in nM. Ki may be expressed in terms of specific receptors (e.g., MC1 r, MC3r, MC4r or MC5r).

By "inhibition" is meant the percent attenuation, or decrease in receptor binding, in a competitive inhibition assay compared to a known standard. Thus, by "inhibition at 1 μM (NDP-α-MSH)" is meant the percent decrease in binding of NDP-α-MSH by addition of a determined amount of the compound to be tested, such as 1 μM of a test compound, such as under the assay conditions hereafter described. By way of example, a test compound that does not inhibit binding of NDP-α-MSH has a 0% inhibition, and a test compound that completely inhibits binding of NDP-α-MSH has a 100% inhibition. Typically, as described hereafter, a detectably labeled assay is used for competitive inhibition testing, such as with $I^{125}$-labeled NDP-α-MSH, or a lanthanide chelate fluorescent assay, such as with Eu-NDP-α-MSH. However, other methods of testing competitive inhibition are known, including use of different label or tag systems, and in general any method known in the art for testing competitive inhibition may be employed in this invention. It may thus be seen that "inhibition" is one measure to determine whether a test compound attenuates binding of α-MSH to melanocortin receptors.

By "binding affinity" is meant the ability of a compound or drug to bind to its biological target, expressed herein as Ki (nM).

By "$E_{max}$" is meant the maximal functional activity achievable by a compound in a specified melanocortin receptor expressing cell system, such as the maximal stimulation of adenylyl cyclase. The maximal stimulation achieved by NDP-α-MSH is designated as an $E_{max}$ of 100% and a compound capable of stimulating half the maximal activity of NDP-α-MSH is designated as having an $E_{max}$ of 50%. A compound of this invention that under assay conditions described herein has an $E_{max}$ of 70% or higher may be classified as an agonist, a compound with an $E_{max}$ between 10% and 70% may be classified as a partial agonist, and a compound with an $E_{max}$ below 10% may be classified as inactive.

In general, "functional activity" is a measure of the signaling of a receptor, or measure of a change in receptor-associated signaling, such as with a melanocortin receptor, upon activation of the receptor by a compound. Melanocortin receptors initiate signal transduction through activation of heterotrimeric G proteins. In one aspect, melanocortin receptors signal through Gas, which catalyzes production of cAMP by adenylyl cyclase. Thus, determination of stimulation of adenylyl cyclase, such as determination of maximal stimulation of adenylyl cyclase, is one measure of functional activity, and is a primary measure exemplified herein. However, it is to be understood that alternative measures of functional activity may be employed in the practice of this invention and are specifically contemplated and included within the scope of this invention. Thus, in one example intracellular free calcium may be measured using specific fluorescent molecules binding to calcium, such as Fura2, reported by and using the methods disclosed in Mountjoy K. G. et al., Melanocortin receptor-medicated mobilization of intracellular free calcium in HEK293 cells. *Physiol Genomics* 5:11-19, 2001, or Newman et al., Activation of the melanocortin-4 receptor mobilizes intracellular free calcium in immortalized hypothalamic neurons. *J Surg Res:* 132: 201-207, 2006. Fluo-4 is an alternative calcium binding dye that is also commonly used (Nohr et al., The orphan G protein-coupled receptor GPR139 is activated by the peptides: Adrenocorticotropic hormone (ACTH), α-, and β-melanocyte stimulating hormone (α-MSH, and β-MSH), and the conserved core motif HFRW (SEQ ID NO: 82). *Neurochem Int* 102:105-113, 2017). Further upstream to the $Ca2^+$ release event and in the same pathway, it is also possible to measure activation by measurement of the production of inositol triphosphate or diacylglycerol from phosphatidylinositol 4,5-biphosphate, such as the commercially-available HTRF assays (Liu et al., Comparison on functional assays for Gq-coupled GPCRs by measuring inositol monophospate-1 and intracellular calcium in 1536-well plate format. *Curr Chem Genomics* 1:70-77, 2008). Yet another measure of functional activity is receptor internalization, resulting from activation of regulatory pathways, such as using the methods disclosed in Nickolls S. A. et al., Functional selectivity of melanocortin 4 receptor peptide and nonpeptide agonists: evidence for ligand specific conformational states. *J Pharm Exper Therapeutics* 313:1281-1288, 2005. Yet another measure of functional activity is the exchange, and exchange rate, of nucleotides associated with activation of a G protein receptor, such as the exchange of GDP (guanosine diphosphate) for GTP (guanosine triphosphase) on the G protein a subunit, which may be measured by any number of means, including a radioassay using guanosine 5'-(γ-[$^{35}$S]thio)-triphosphate, as disclosed in Manning D. R., Measures of efficacy using G proteins as endpoints: differential engagement of G proteins through single receptors. *Mol Pharmacol* 62:451-452, 2002. A relatively new assay platform has been devised to measure the activity/engagement of the 14 different Ga species belonging to the Gi, Gq, Gs, Gi2/i3 subfamilies as it relates to the receptor using BRET (bioluminescence resonance energy transfer)-based biosensors to measure the disengagement of the Ga and Gy subunits upon ligand binding (Zhao et al., Biased signaling of protease-activated receptors. *Front Endocrinol* 5:67, 2014; and van der Westhuizen et al., Quantification of ligand bias for clinically relevant β2-adrenergic receptor ligands: Implications for drug taxonomy. *Molecular Pharm* 85:492-509, 2014). Various gene-based assays have been developed for measuring activation of G-coupled proteins, such as those disclosed in Chen W. et al., A colorimetric assay from measuring activation of Gs- and Gq-coupled signaling pathways. *Anal Biochem* 226: 349-354, 1995; Kent T. C. et al., Development of a generic dual-reporter gene assay for screening G-protein-coupled receptors. *Biomol Screening,* 5:437-446, 2005; or Kotarsky K. et al., Improved receptor gene assays used to identify ligands acting on orphan seven-transmembrane receptors. *Pharmacology & Toxicology* 93:249-258, 2003. The colorimetric assay of Chen et al. has been adapted for use in measuring melanocortin receptor activation, as disclosed in Hruby V. J. et al., Cyclic lactam α-melanocortin analogues of Ac-$Nle^4$-cyclo[$Asp^5$,D-$Phe^7$,$Lys^{10}$]α-melanocyte-stimulating hormone-(4-10)—$NH_2$ with bulky aromatic amino acids at position 7 shows high antagonist potency and selectivity at specific melanocortin receptors. *J Med Chem* 38:3454-3461, 1995. In general, functional activity may be measured by any method, including methods of determining activation and/or signaling of a G-coupled receptor, and further including methods which may be hereafter developed or reported. Each of the foregoing articles, and the methods disclosed therein, is incorporated here by reference as if set forth in full.

The terms "treat," "treating" and "treatment," as used herein, contemplate an action that occurs while a patient is suffering from the specified disease or disorder, which reduces the severity of the disease or disorder.

As used herein, the term "pharmacologically effective amount" (including "therapeutically effective amount") means an amount of a peptide according to the invention that is sufficient to induce a desired therapeutic or biological effect.

As used herein, the term "therapeutically effective amount" means the amount of a compound including a peptide of the invention that will elicit a biological or medical response in the mammal that is being treated by a medical doctor or other clinician.

As used herein, the term "prophylactically effective" or "preventive" means the amount of a compound including a peptide of the invention that will prevent or inhibit affliction or mitigate affliction of a mammal with a medical condition that a medical doctor or other clinician is trying to prevent, inhibit, or mitigate before a patient begins to suffer from the specified disease or disorder.

2.0 Clinical Indications and Utility

The compositions and methods disclosed herein can be used for both medical applications and animal husbandry or veterinary applications. The term "patient" is intended to denote a human and is so used throughout the specification and in the claims. The primary applications of the peptides disclosed herein, or of a formula disclosed herein, involve human patients, but the peptides disclosed herein, or of a formula disclosed herein, may be applied to laboratory, farm, zoo, wildlife, pet, sport or other animals. Clinical indications and specific utilities include the following:

2.1 Inflammatory and Fibrotic Diseases and Conditions

Peptides and compositions of the present invention, including without limitation peptides that are MC1r, MC3r, MC4r and/or MC5r agonists, partial agonists, antagonists, or any combination thereof, may be utilized in the treatment of inflammatory diseases and inflammatory conditions in a patient. There are a number of inflammatory diseases and inflammatory conditions which may be so treated. In one aspect, the inflammatory condition results from a disease including a form of arthritis, including but not limited to osteoarthritis, rheumatoid arthritis, septic arthritis, gout and pseudogout, juvenile idiopathic arthritis, Still's disease and ankylosing spondylitis, as well as arthritis secondary to other diseases, such as arthritis secondary to lupus erythematosus, Henoch-Schönlein purpura, psoriatic arthritis, reactive arthritis, haemochromatosis, hepatitis, Wegener's granulomatosis, vasculitis syndromes, Lyme disease, familial Mediterranean fever, hyperimmunoglobulinemia D with recurrent fever, TNF receptor-associated periodic syndrome and inflammatory bowel disease, including Crohn's disease and ulcerative colitis. In another aspect, the inflammatory condition results from a disease including a form of inflammatory bowel disease, such as Crohn's disease, ulcerative colitis, collagenous colitis, lymphocytic colitis, ischemic colitis, diversion colitis, Behcet's syndrome, infective colitis and indeterminate colitis. In another aspect, the inflammatory condition results from an autoimmune disease, including but not limited to systemic syndromes such as systemic lupus erythematosus, Sjögren's syndrome, scleroderma, rheumatoid arthritis and polymyositis, or a syndrome affecting only a local body system, such as the endocrine system (diabetes mellitus type 1, Hashimoto's thyroiditis, Addison's disease, etc.), dermatologic system (pemphigus vulgaris), hematologic system (autoimmune hemolytic anemia), or neural system (multiple sclerosis). Thus autoimmune diseases include, in addition to the general syndromes discussed above, such diseases and conditions as acute disseminated encephalomyelitis, Addison's disease, ankylosing spondylitis, antiphospholipid antibody syndrome, aplastic anemia, autoimmune hepatitis, autoimmune oophoritis, celiac disease, Crohn's disease, gestational pemphigoid, Goodpasture's syndrome, Graves' disease, Guillain-Barre syndrome, Hashimoto's disease, idiopathic thrombocytopenic purpura, Kawasaki disease, lupus erythematosus, mixed connective tissue disease, multiple sclerosis, myasthenia gravis, opsoclonus myoclonus syndrome, optic neuritis, Ord's thyroiditis, pemphigus, pernicious anaemia, primary biliary cirrhosis, Reiter's syndrome, Sjögren's syndrome, Takayasu's arteritis, temporal arteritis, autoimmune hemolytic anemia and Wegener's granulomatosis.

In another aspect, the inflammatory condition results from or is related to chronic obstructive pulmonary disease (COPD), also known as chronic obstructive airway diseases, including but not limited to diseases characterized by the pathological limitation of airflow in the airway that is not fully reversible, such as for example chronic bronchitis, emphysema, pneumoconiosis, pulmonary neoplasms and other lung disorders. Other inflammatory conditions include upper or lower airway diseases and disorders, such as allergic asthma, non-allergic asthma, allergic rhinitis, vasomotor rhinitis, allergic conjunctivitis, non-allergic conjunctivitis, and the like, as well as airway diseases related to external toxins or substances, such as various forms of pneumoconiosis (coalworker's pneumoconiosis, asbestosis, silicosis, bauxite fibrosis, berylliosis, or siderosis), byssinosis or hypersensitivity pneumonitis (farmer's lung or bird fancier's lung). Other lung diseases involving an inflammatory condition include acute respiratory distress syndrome. The peptides and compositions of the present invention are of particular utility tor treatment of conditions wherein glucocorticoids are either ineffectual or inadequate to bring about the desired pharmacological response, such as COPD, asthma in individuals who smoke, and other conditions characterized, in whole or in part, by eosinophil accumulation in the lung, neutrophil infiltration and activation, alveolar macrophage recruitment and activation, epithelial cell expression of IL-8 or increased expression of TNF-α. For airway or lung disorders, in one aspect the peptides of the present invention are delivered systemically, in another aspect the peptides of the present invention are delivered locally, such as by inhalation administration.

In yet another aspect, the inflammatory condition results from or is related to some form of transplant-related condition or syndrome, such as graft-versus-host disease, hyperacute rejection, acute rejection, or chronic rejection. Graft-versus-host disease is a common complication of allogeneic bone marrow transplantation, but can occur with other transplantations, and particularly those with T cells present in the graft, either as contaminants or intentionally introduced. Hyperacute, acute or chronic rejection can occur with bodily organs such as kidneys, liver, pancreas, spleen, uterus, heart or lungs, as well as transplantation of bone, cornea, face, hand, penis or skin. In one embodiment, a pharmaceutical composition including one or more of the peptides of the present invention is given prophylactically to limit or prevent a transplant-related condition or syndrome, such as immediately before, during or after transplantation of a bodily fluid, organ or part. In another embodiment, the bodily fluid, organ or part being transplanted is perfused with a solution of a pharmaceutical composition including one or more of the peptides of the present invention. In yet another embodiment, one or more of the peptides of the present invention are administered in conjunction with, combination with or series with one or more other agents for transplant rejection, such as calcineurin inhibitors including cyclosporin or tacrolimus, mTOR inhibitors including sirolimus or everolimus, anti-proliferatives including azathioprine or mycophenolic acid, corticosteroids including prednisolone or hydrocortisone, antibodies such as monoclonal anti-IL-2Rα receptor antibodies, basiliximab or daclizumab, or polyclonal anti-T-cell antibodies such as anti-thymocyte globulin or anti-lymphocyte globulin.

In yet another aspect, peptides and compositions of the present invention, including without limitation peptides that are MC1r, MC3r, MC4r and/or MC5r agonists, partial agonists, antagonists, or any combination thereof, may be utilized in the treatment of fibrotic and sclerotic diseases, indications, conditions and syndromes in a patient. There are numerous fibrotic and sclerotic diseases, indications, conditions and syndromes which may be so treated. Fibrotic and sclerotic diseases, indications, conditions and syndromes frequently include an inflammatory component, and thus many may similarly be categorized as an inflammatory disease or condition and are listed above. Fibrotic and sclerotic diseases and conditions, in addition to including an inflammatory component, may also be idiopathic, toxic, hereditary and/or pharmacologically induced disorders. In general, fibrotic disorders are characterized by excessive production of extracellular matrix, primarily type I collagen, which may result in loss of organ function. It is believed, without wishing to be bound by theory, that agonism of MC1r can result in suppression of transforming growth factor-$\beta_1$-induced collagen synthesis by human dermal fibroblasts, thereby providing therapeutic and/or prophylactic benefit for fibrotic and sclerotic diseases, indications, conditions and syndromes. Representative fibrotic and sclerotic diseases and conditions that can be so treated include, but are not limited to, localized scleroderma, systemic sclerosis, sclerodermic graft-versus-host disease of the skin, idiopathic lung fibrosis, bleomycin-induced lung fibrosis, cyclosporine-induced nephropathy, cirrhosis of the liver, hypertrophic scars, keloids and the like.

In yet another aspect peptides and compositions of the present invention, including without limitation peptides that are MC1r, MC3r, MC4r and/or MC5r agonists, partial agonists, antagonists, or any combination thereof, and in particular MC1r and MC5r agonists, may be utilized in the treatment of fibrotic diseases, conditions and syndromes in a patient. Such fibrotic process may be secondary to chronic inflammation, and development of fibrosis is a common consequence of chronic inflammation. There is a wide range of diseases in which fibrosis is a cause of mortality and morbidity, including pulmonary fibrosis, liver fibrosis and cirrhosis, chronic kidney disease, myocardial infarction, and systemic autoimmune diseases such as systemic sclerosis. Fibrosis may also occur in ocular diseases, particularly those characterized by chronic inflammation. It is believed that the peptides and compositions of the present invention can both inhibit formation of fibrosis and can have a regenerative property, reducing or ameliorating the effects of fibrosis.

In yet another aspect peptides and compositions of the present invention, including without limitation peptides that are MC1r, MC3r, MC4r and/or MC5r agonists, partial agonists, antagonists, or any combination thereof, may be utilized in the treatment of diseases related to increased cytokine expression and related diseases, indications, conditions and syndromes in a patient. Expression of various cytokines is increased during an inflammatory process, including an inflammatory process secondary to circulatory shock, ischemia, reperfusion injury and the like. TNF-α is a pleiotropic cytokine produced mainly by macrophages, and also by other types of cells. Other cytokines which increase during an inflammatory process, including an inflammatory process secondary to circulatory shock, ischemia, reperfusion injury and the like, include IL-1 and IL-6. While cytokines such as TNF-α have beneficial effects in many instances, significantly increased levels, such as secondary to circulatory shock, ischemia, reperfusion injury and the like, can have pathological effects. In one aspect, reperfusion of hypoxic or ischemic tissues, such as secondary to circulatory shock, results in inflammatory responses, including increased cytokine expression.

In one embodiment, the invention is directed to methods of using one or more of the peptides of the present invention to decrease pro-inflammatory cytokine production and expression, including decreasing pro-inflammatory cytokine production and expression secondary to circulatory shock, ischemia, reperfusion injury and the like. The decrease in pro-inflammatory cytokine production and expression, including without limitation one or more of TNF-α, IL-1 and IL-6, occurs preferably within a short time period following administration of a composition comprising one or more of the peptides of the present invention.

In a related embodiment, the invention is directed to methods of using one or more of the peptides and compositions of the present invention, including without limitation peptides that are MC1r, MC3r, MC4r and/or MC5r agonists, partial agonists, antagonists, or any combination thereof, to increase anti-inflammatory cytokine production and expression. The increase in anti-inflammatory cytokine production and expression, including without limitation IL-10, occurs within a short time period following administration of a composition comprising one or more of the peptides of the present invention.

2.2 Dermatologic Indications

In yet another aspect, peptides and compositions of the present invention, including without limitation peptides that are MC1r agonists or partial agonists, may be utilized in the treatment of dermatologic and cosmetic diseases, indications, conditions and syndromes. In one aspect, peptides and compositions of the present invention are MC1r agonists which stimulate melanocytes and related cells to increase the level of melanin in the skin. By increasing the level of melanin in the skin, protection against ultraviolet radiation (UVR) and sunlight is afforded, including protection against phototoxicity and photosensitivity of the skin caused by UVR, sun and light.

In yet another aspect, peptides and compositions of the present invention, including without limitation peptides that are MC1r, MC3r, MC4r and/or MC5r agonists, partial agonists, antagonists, or any combination thereof, may be utilized for prophylactic and/or therapeutic treatment of dermal diseases, indications, conditions and syndromes such as acne vulgaris (commonly referred to as acne), atopic dermatitis (commonly referred to as atopic eczema or eczema), polymorphous light eruption, psoriasis, rosacea, seborrheic dermatitis, vitiligo, porphyria, porphyria cutanea tarda, erythropoietic protoporphyria, solar urticaria, urticaria pigmentosa or xeroderma pigmentosum. In another aspect, peptides, compositions and methods of the present invention may be utilized to prevent, limit or treat photosensitive or photoresponsive viral infections, such as herpes simplex virus (commonly referred to as cold sores and genital herpes depending on the site of infection), human papilloma virus and varicella zoster virus. In another aspect, peptides, compositions and methods of the present invention may be utilized to prevent, limit or treat cancers of the skin, including use in pre-cancerous conditions, and including use in actinic keratosis, basal cell carcinoma, melanoma or squamous cell carcinoma. In another aspect, peptides, compositions and methods of the present invention may be utilized to prevent or limit adverse effects of various therapies, including phototherapies, such as photodynamic therapy. In yet another aspect, peptides, compositions and methods of the present invention may be utilized to induce a tan, to decrease hair graying or for similar and related purposes relating to increased melanin production.

2.3 Cancers

Certain cancers, such as mesothelioma, are reported to be very sensitive to growth-promoting influences of cytokines and growth factors and may be treatable by means of peptides selective for MC1r. Canania, A., et al., "Autocrine inhibitory influences of α-melanocyte-stimulating hormone in malignant pleural mesothelioma," *J. Leukoc. Biol.* 75:253-259 (2004). Cancers that may be so treated include pleural mesothelioma, known to express mRHA for MC1r and the receptor protein, as well as other tumors that express MC1r including but not limited to adenocarcinoma, such as pulmonary adenocarcinoma.

2.4 Ocular Diseases and Indications

There are a number of ocular diseases, indications, conditions and syndromes characterized by inflammation, including but not limited to increased cytokine production, that may be treated with peptides and compositions of the present invention, including without limitation peptides that are MC1r, MC3r, MC4r and/or MC5r agonists, partial agonists, antagonists, or any combination of the foregoing. One example is dry eye disease, also known as dry eye syndrome or keratoconjunctivitis sicca, an ocular disease affecting approximately 10-20% of the population. This disease progressively affects larger percentages of the population as it ages, with the majority of these patients being women. In addition, ocular irritation is experienced, or the symptoms and/or signs of dry eye as a condition are experienced, from time to time under certain circumstances, such as prolonged visual tasking (e.g., working on a computer), being in a dry environment, using medications that result in ocular drying and so on. In individuals suffering from dry eye, the protective layer of tears that normally protects the ocular surface is compromised, a result of insufficient or unhealthy production of one or more tear components. This can lead to exposure of the surface of the eye, ultimately promoting desiccation and damage of surface cells. Signs and symptoms of dry eye include but are not limited to keratitis, conjunctival and corneal staining, redness, blurry vision, decreased tear film break-up time, decreased tear production, tear volume, and tear flow, increased conjunctival redness, excess debris in the tear film, ocular dryness, ocular grittiness, ocular burning, foreign body sensation in the eye, excess tearing, photophobia, ocular stinging, refractive impairment, ocular sensitivity, and ocular irritation. Patients may experience one or more of these symptoms.

There are many possible variables that can influence a patient's signs or symptoms of dry eye including levels of circulating hormones, various autoimmune diseases (e.g., Sjogren's syndrome and systemic lupus erythematosus), ocular surgeries including PRK or LASIK, many medications, environmental conditions, visual tasking such as computer use, ocular fatigue, contact lens wear, and mechanical influences such as corneal sensitivity, partial lid closure, surface irregularities (e.g., pterygium), and lid irregularities (e.g., ptosis, entropion/ectropion, pinguecula). Environments with low humidity, such as those that cause dehydration, can exacerbate or cause dry eye symptoms, such as sitting in a car with the defroster on or living in a dry climate zone. In addition, visual tasking can exacerbate symptoms. Tasks that can greatly influence symptoms include watching TV or using a computer for long periods of time where the blink rate is decreased.

Uveitis is an ocular disease involving inflammation of the middle layer or uvea of the eye and may also be understood to include any inflammatory process involving the interior of the eye. Uveitis includes anterior, intermediate, posterior and panuveitic forms, with most uveitis cases anterior in location, involving inflammation of the iris and anterior chamber. This condition can occur as a single episode and subside with proper treatment or may take on a recurrent or chronic nature. Symptoms include red eye, injected conjunctiva, pain and decreased vision. Signs include dilated ciliary vessels, presence of cells and flare in the anterior chamber, and keratic precipitates on the posterior surface of the cornea. Intermediate uveitis includes inflammation and the presence of inflammatory cells in the vitreous cavity, and posterior uveitis include the inflammation of the retina and choroid. Uveitis may be secondary to any of a number of diseases and disorders, including acute posterior multifocal placoid pigment epitheliopathy, ankylosing spondylitis, Behçet's disease, birdshot retinochoroidopathy, brucellosis, herpes simplex, herpes zoster, inflammatory bowel disease, juvenile rheumatoid arthritis, Kawasaki disease, leptospirosis, Lyme disease, multiple sclerosis, psoriatic arthritis, Reiter's syndrome, sarcoidosis, syphilis, systemic lupus erythematosus, toxocariasis, toxoplasmosis, tuberculosis, Vogt-Koyanagi-Harada syndrome, Whipple disease or polyarteritis nodosa.

Other ocular inflammatory conditions for which one or more of the peptides of the present invention may be employed for treatment include but are not limited to corneal ulcer, corneal erosion, corneal abrasion, corneal degeneration, corneal perforation, corneal scarring, epithelial defect, keratoconjunctivitis, idiopathic uveitis, corneal transplantation, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, pterygium, a wound sustained to ocular surface, post-photorefractive keratotomy eye pain and inflammation, thermal or chemical burn to the cornea, scleral wound, keratoconus or conjunctival wound.

In one embodiment, the invention is directed to methods of using one or more of the peptides of the present invention for treatment of any of the foregoing ocular diseases, indications, conditions and syndromes. Such treatment may include treatment by means of eye drops, ointments, gels, washes, implants, plugs or other means and methods for delivering one or more of the peptides of the present invention to an ocular surface, or alternatively by intravitreal injection or similar means providing for delivery to the vitreous humor, or alternatively by systemic administration, including oral administration, subcutaneous injection or intravenous injection, to a patient responsive thereto.

For corneal transplant and similar ex vivo procedures, the invention is directed to methods of using one or more of the peptides of the present invention for preservation of transplant tissue, including but not limited to reduction of pro-inflammatory cytokines, enhanced IL-10 production, and increased endothelial cell survival. The invention is thus directed both to methods of using one or more of the peptides of the present invention for preservation of transplant tissue, and also methods of treating patients immediately before, at and following corneal transplant, which treatment may comprise administration of drops or other localized administration of one or more of the peptides of the present invention.

2.5 Ischemia and Related Indications

In yet another aspect, peptides and compositions of the present invention, including without limitation peptides that are that are MC1r, MC3r, MC4r and/or MC5r agonists, partial agonists, antagonists, or any combination thereof, may be used in the treatment of ischemia and related diseases, indications, conditions and syndromes. Ischemia includes any decrease or stoppage in the blood supply to any bodily organ, tissue, cell, or part, particularly where that decrease or stoppage leads to or would likely lead to ischemic damage to the bodily organ, tissue, cell, or part. An "ischemic episode" refers to any transient or permanent period of ischemia. Ischemia may result from any constriction or obstruction of the vasculature, or may result from circulatory shock, such as hemorrhagic shock, hypovolemic shock, or the like. The decrease or lack of blood flow results in a decrease or lack of oxygen to the affected part of the body and may also result in an increase of inflammatory disease mediator chemicals such as various cytokines and other substances. During certain surgical procedures such as cardiac surgery and organ transplantation, the flow of blood is stopped temporarily and then resumed (reperfusion), resulting in ischemia-reperfusion injury. During a heart attack, the blood that supplies the heart is stopped, also resulting in ischemia that can evolve into infarction. Current treatment to relieve heart attacks requires reperfusion of the ischemic area of the heart, such as by using thrombolytic drugs or coronary angioplasty.

The peptides and compositions of the invention have particular application in prevention of injury due to renal ischemia, including lung injury secondary to renal ischemia, preventing or limiting ischemic heart injuries subsequent to a myocardial infarction, preventing or limiting ischemic brain injuries subsequent to a cardiovascular injury, including without limitation myocardial infarction, stroke or the like. Neuroprotection is provided by administration of a composition of the invention to a patient with cerebral ischemia or stroke, particularly patients who are concurrently hypotensive. The peptides and compositions of the invention have further particular application in preventing or limiting ischemic organ damage in organ transplant, including transplant of the heart, kidney, liver, lungs, pancreas or small intestine. In one aspect, a pharmaceutical composition of the present invention may be utilized for perfusion of a transplant organ, which perfusion may be prior to, during or subsequent to transplant of the organ.

In one embodiment, the invention is directed to methods of using one or more of the peptides of the present invention to protect the heart, brain or other organs of a patient against injury caused by ischemia. The protective effect against ischemia occurs instantaneously or within a short time period following administration of a composition comprising one or more of the peptides of the present invention.

Ischemia may also result from any of a variety of diseases or conditions, and in one embodiment the invention is directed to methods of using one or more of the peptides of the present invention to protect the organs of a patient against injury resulting from ischemia, which ischemia is caused by a disease or condition. Such disease or condition may include, by way of example and not limitation, atherosclerotic diseases such as atheromata with thrombosis, embolism from the heart or from blood vessel from any organ, vasospasm, hypotension due to heart disease, hypotension due to systemic disease including infection or allergic reactions, or hypotension resulting from administration, ingestion or other exposure to one or more toxic compounds or drugs. Ischemia may also be secondary ischemia, and in another embodiment the invention is directed to methods of using one or more of the peptides of the present invention to protect the organs of a patient against injury resulting from secondary ischemia. Such secondary ischemia may be secondary to a disease or condition such diabetes mellitus, hyperlipidemia, hyperlipoproteinemia, dyslipidemia Buerger's disease, also called thromboangiitis obliterans, Takayasu's arteritis, arteritis temporalis, Kawasaki disease, also called lymph node syndrome, mucocutaneous node disease, infantile polyarteritis, cardiovascular syphilis, and various connective tissue diseases and disorders.

In yet another aspect, peptides and compositions of the present invention, including without limitation peptides that are that are MC1r, MC3r, MC4r and/or MC5r agonists, partial agonists, antagonists, or any combination thereof, may be used in the treatment of ischemia-reperfusion injury and related diseases, indications, conditions and syndromes. While restoration of blood flow following ischemia is essential to preserve functional tissue, the reperfusion itself is known to be harmful to the tissue. Both ischemia and reperfusion are known to be important contributors to tissue necrosis. Several mechanisms appear to play a causative role in the generation of tissue damage associated with ischemia-reperfusion injury. Certain of the peptides and compositions of the present invention have particular application in preventing or limiting the severity of renal reperfusion injury, including lung injury secondary to renal reperfusion, preventing or limiting reperfusion heart injuries subsequent to a myocardial infarction, preventing or limiting reperfusion brain injuries subsequent to a cardiovascular injury, including without limitation myocardial infarction, stroke or the like. The invention has further particular application in preventing or limiting reperfusion organ damage in organ transplant, including transplant of the heart, kidney, liver, lungs, pancreas or small intestine. In one aspect, the pharmaceutical composition of the present invention may be utilized for perfusion of a transplant organ, which perfusion may be prior to, during or subsequent to transplant of the organ.

In one embodiment, the invention is directed to methods of using one or more of the peptides of the present invention to protect the heart, brain or other organs of a patient against injury caused by ischemia-reperfusion injury, including injury caused by or during reperfusion. The protective effect against ischemia-reperfusion injury occurs instantaneously or within a short time period following administration of a composition comprising one or more of the peptides of the present invention.

In yet another aspect, peptides and compositions of the present invention, including without limitation peptides that are that are MC1r, MC3r, MC4r and/or MC5r agonists, partial agonists, antagonists, or any combination thereof, may be used in the treatment of circulatory shock and related diseases, indications, conditions and syndromes in a patient. The invention provides peptides, compositions for use and methods of treating or preventing shock, including hemorrhagic shock, in a patient, which include administering a composition including one or more of the peptides of the present invention to a patient diagnosed as suffering from blood loss. The blood loss may, but need not, be measured as a percentage of the subject's blood volume, such as, for example, a blood loss of greater than about 15% total blood volume, or greater than 20%, 25%, 30%, 35%, 40%, or 50% of the subject's total volume. Alternatively, the blood loss may, but need not, be measured in terms of a drop in blood volume in any amount sufficient to cause hemorrhagic shock in a particular subject, such as, for example, a loss of about 750 mL, 1000 mL, of about 1500 mL, or of about 2000 mL or more in a human subject. The blood loss may also be measured in terms of a drop in systolic blood pressure, such as, for example, a drop in systolic blood pressure that is about 20 mm Hg, 30 mm Hg, 40 mm Hg, 50 mm Hg, 60 mm Hg, 70 mm Hg, 80 mm Hg, 90 mm Hg or 100 mm Hg or more than 100 mm Hg lower than the subject's normal systolic blood pressure. In particular embodiments, the subject is undergoing or has undergone a medical procedure, such as, but not limited to, surgery, a transfusion or child birth. In other particular embodiments, the subject has suffered a traumatic injury, such as, but not limited to, resulting from a motor vehicle accident, from an industrial injury, or from a gunshot wound.

In additional embodiments of the present invention, the compositions and methods are used to treat cardiogenic shock, hypovolemic shock and vasodilatory shock, each of which can be in any stage of shock. In one particular embodiment of the present invention, the methods are used to treat cardiogenic shock. Cardiogenic shock is, generally speaking, low blood flow or perfusion that is caused by heart malfunction where the heart does not pump adequate blood. Causes can include any condition that interferes with ventricular filling or emptying, such as, but not limited to, embolism, ischemia, regurgitation and valve malfunction. In another particular embodiment of the present invention, the methods are used to treat vasodilatory shock. Vasodilatory shock is caused by severe venous or arteriolar dilation, which results in inadequate blood flow. Several known causes contribute to vasodilatory shock including, but not limited to, cerebral trauma, drug or poison toxicity, anaphylaxis, liver failure, bacteremia and sepsis. In another more particular embodiment of the present invention, the methods are used to treat shock resulting from sepsis or bacteremia. In an even more particular embodiment, the compositions and methods are used to treat septic shock or bacteremic shock in shock referred to as Stage I, II or III shock. In yet another embodiment, the compositions and methods of the present invention are used to treat hypovolemic shock. Hypovolemic shock is, generally speaking, decreased intravascular volume, which decrease in intravascular volume can be relative or absolute. Hemorrhage from conditions such as, but not limited to, ulcers, gastrointestinal injury, trauma, accidents, surgery, and aneurysm may cause hypovolemic shock; but loss of other body fluids may also cause hypovolemic shock. For instance, renal fluid loss, intravascular fluid loss, water or other peritoneal fluid loss may contribute to hypovolemic shock. In one particular embodiment of the present invention, the compositions and methods, including administration of one or more of the peptides of the present invention, are used to treat hypovolemic shock. In an even more particular embodiment, the compositions and methods are used to treat hypovolemic shock in Stage I, Stage II or Stage Ill.

In one embodiment, the invention is directed to methods of using one or more of the peptides of the present invention to protect the heart, brain or other organs of a patient against injury caused by circulatory shock. The protective effect against circulatory shock occurs instantaneously or within a short time period following administration of a composition comprising one or more of the peptides of the present invention, preferably within at least about 40 minutes following administration.

2.6 MC4r Responsive Indications

In yet another aspect, peptides and compositions of the present invention, including without limitation peptides that are MC4r agonists or partial agonists or MC3r agonists or partial agonists, or any combination thereof, may be utilized in treating diseases, disorders and/or conditions responsive to modulation of the MC4r function, more particularly activation of the MC4r, i.e. diseases, disorders and/or conditions which would benefit from agonism (including full or partial agonism) at the MC4r, or responsive to modulation of the MC3r function, more particularly activation of the MC3r, i.e. diseases, disorders and/or conditions which would benefit from agonism (including full or partial agonism) at the MC3r, or modulation of both the MC4r and MC3r function, including energy homeostasis and metabolism related (such as diabetes, in particular type 2 diabetes; dyslipidemia; fatty liver; gout; hypercholesterolemia; hypertriglyceridemia; hyperuricacidemia; impaired glucose tolerance; impaired fasting glucose; insulin resistance syndrome; and metabolic syndrome), food intake related (such as hyperphagia; binge eating; bulimia; and compulsive eating) and/or energy balance and body weight related diseases, disorders and/or conditions, more particularly such diseases, disorders and conditions characterized by excess body weight and/or excess food intake. In one aspect, compounds of the invention are utilized to treat conditions relating to various expression or receptor genetic diseases such as pro-opiomelanocortin deficiency due to mutations in the POMC gene (POMC heterozygous deficiency obesity), Prader-Willi syndrome, obesity due to MC4r deficiency, leptin receptor deficiency obesity, leptin deficiency obesity, including congenital leptin deficiency, Bardet Biedl syndrome, Alstrom syndrome, and various other diseases, conditions, genetic deficiencies, metabolic disorders, and syndromes.

Such peptides are particularly believed to be useful for treatment of body weight related diseases, disorders and/or conditions characterized by excess body weight, including obesity and overweight (by promotion of weight loss, maintenance of weight loss, and/or prevention of weight gain, including medication-induced weight gain or weight gain subsequent to cessation of smoking), and diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

MC4r is a part of the leptin-melanocortin pathway, or pro-opiomelanocortin (POMC)-MC4r pathway. Constituent members of this pathway include a wide diversity of proteins, including α-MSH, POMC, leptin and leptin receptors. Certain diseases, conditions and syndromes result from mutations and variations, including genetic defect disorders, associated with or in one or more constituent members of the POMC-MC4r pathway. The compounds of this invention may, as hereafter described, be useful in treatment of diseases, conditions and syndromes resulting from mutations and variations, including genetic defect disorders, associated with or in one or more constituent members of the POMC-MC4r pathway.

The hypothalamic POMC-MC4r pathway is part of the regulatory system modulating feed behavior, appetite and body weight. There are a number of diseases, conditions and syndromes which have been described associated with disruption of the hypothalamic POMC-MC4r pathway which is believed to result from genetic defects or disruptions, include defects or disruptions in genes in the POMC-MC4r pathway. For example, Prader-Willi syndrome manifests in significant hyperphagia and severe obesity, and may include other features and signs, such as learning disabilities, abnormal neurologic function, hypogonadism, short stature and developmental and cognitive delays. The compounds of this invention may, as hereafter described, be useful in treatment of Prader-Willi syndrome, as well as other diseases, conditions and syndromes involving defects or disruptions in genes in the POMC-MC4r pathway.

Thus compounds of the invention may be utilized and are indicated for the treatment of the obesity and hyperphagia associated with POMC deficiency caused by homozygous or compound heterozygous loss of function mutations in the POMC gene located at chromosome 2, position 23.3. Mutations in the POMC gene that result in complete loss of or that significantly reduce production of the POMC polypeptide lead to no or reduced production of α-MSH. This loss of endogenous α-MSH results in significantly diminished MC4r activity with resulting hyperphagia and obesity. Compounds of this invention may be utilized as a replacement MC4r agonist therapeutic in patients with little or no endogenous α-MSH.

For a variety of diseases, conditions or syndromes associated with disruption of the hypothalamic POMC-MC4r pathway, various genetic and genotyping tests may be employed as part of diagnosis of prospective patients, and determining suitability for use of the compounds of this invention in such prospective patients. By way of example and not limitation, for Prader-Willi syndrome it is possible to utilize genetic testing such as DNA-based methylation testing to ascertain the loss of active genes in a specific part of chromosome 15, the 15q11-q13 region, specifically deletion of at least the 15q11-q13 region of paternal chromosome 15. Similarly, POMC deficiency may be diagnosed by loss of function mutations in the POMC gene. Thus treatment with a compound of this invention may include various diagnostic and genetic tests to ascertain the presence of a loss of function mutation or other mutation in the POMC-MC4r pathway, including but not limited to a loss of function mutation for Prader-Willi syndrome affecting the 15q11-q13 region, loss of function mutations in the POMC gene, the leptin gene, the leptin receptor gene, and various other genes in the POMC-MC4r pathway.

In yet another aspect, peptides and compositions of the present invention, including without limitation peptides that are MC4r agonists or partial agonists, may be employed for the treatment of sexual dysfunction, including both male erectile dysfunction and female sexual dysfunction. Female sexual dysfunction includes, but is not limited to, hypoactive sexual desire disorder. In one particular embodiment, the peptides, compositions and methods of the present invention are used in male patients to increase erectile function, including but not limiting to increasing erectile function so as to permit vaginal intercourse. In another particular embodiment, the peptides, compositions and methods of the present invention are used to treat female sexual dysfunction, including but not limited to an increase in arousal success rate, desire success rate, levels of arousal and desire. For female sexual dysfunction, including hypoactive sexual desire disorder, endpoints may, but need not, be determined by any of a number of validated instruments, including but not limited to the Female Sexual Distress Scale, Female Sexual Encounter Profile, Female Sexual Function Index, and Global Assessment Questionnaire. Patients treated for female sexual dysfunction may be premenopausal women or postmenopausal women.

In yet another aspect, peptides and compositions of the present invention, including without limitation peptides that are MC4r agonists or partial agonists, may be employed for inhibiting alcohol consumption, or for reducing alcohol consumption, or for treating or preventing alcoholism, or for treating or preventing alcohol abuse, or for treating or preventing alcohol-related disorders. In another related aspect, one or more of the present peptides may be employed for inhibiting consumption of drugs of abuse, or for reducing consumption of drugs of abuse, or for treating or preventing drug abuse, or for treating or preventing drug abuse-related disorders. Drugs of abuse are typically controlled substances. These include controlled naturally derived drugs such as heroin, morphine, opium, cocaine, marijuana and the like, as well as synthetically made drugs such as Vicodin®, Lortab®, Lorcet®, Percocet®, Percodan®, Tylox®, hydrocodone, OxyContin®, methadone, tramadol, various methamphetamines, and other tranquilizers, stimulants, or sedatives known to be abused, as well as drugs for which there is no established pharmaceutical utility, such as ecstasy, LSD, or PCP.

In yet another aspect, peptides and compositions of the present invention, including without limitation peptides that are MC4r antagonists, or optionally inverse agonists at MC4r, including MC4r antagonist or inverse agonist peptides that may be agonists, partial agonists, antagonists or inverse agonists at one or more of MC1 r, MC2r, MC3r and MC5r, may be used in the treatment of a variety of body weight disorders including cachexia, sarcopenia and wasting syndrome or disease, and for treatment of inflammation and immune disorders. Body weight disorders include one or more "wasting" disorders (e.g., wasting syndrome, cachexia, sarcopenia) which cause undesirable and unhealthy loss of weight or loss of body cell mass. In the elderly as well as in cancer and AIDS patients, wasting diseases can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, Crohn's disease, psychogenic disease, chronic heart failure or other severe trauma, frequently suffer from wasting disease. Wasting disease is sometimes also referred to as cachexia, and is generally recognized as a metabolic and, sometimes, an eating disorder. Cachexia may additionally be characterized by hypermetabolism and hypercatabolism. Sarcopenia, yet another such disorder which can affect the aging individual, is typically characterized by loss of muscle mass. End stage wasting disease as described above can develop in individuals suffering from either cachexia or sarcopenia.

2.7 Nuclear Medicine and Drug Delivery Applications

In yet another aspect, peptides and compositions of the present invention, including without limitation peptides that are MC1 r agonists, partial agonists, or antagonists, may be used in the targeted imaging and cytotoxic therapy for certain cancers, such melanoma and other indications, in a patient in need thereof. Peptides, compositions and methods of the present invention may be employed for imaging melanoma and other cancers or diseases or conditions characterized, in part, by relatively high expression of MC1r, such as by diagnostic imaging using a radionuclide in combination with a peptide of the present invention. For diagnostic imaging, typically a peptide of the present invention is conjugated to radionuclide by use of a linker, such as a cross-linking agent that couples the peptide of the present invention to a radionuclide. The radionuclide is preferably a gamma emitter that may be imaged using a gamma detector or camera, such as single photon emission computed tomography, or is a positron emitter that may be imaged using positron emission tomography. Gamma emitters that may be so employed include $^{99m}$Tc, $^{111}$In, $^{123}$I and $^{67}$Ga, among others. Positron emitters that may be so employed include $^{11}$C, $^{13}$N, $^{15}$O and $^{18}$F.

In a related aspect, peptides, compositions and methods of the present invention may be employed for cytotoxic therapy of melanoma, other cancers or diseases or conditions characterized, in part, by relatively high expression of MC1r, such as by utilizing a chemotherapeutic agent, including toxins, or radiation therapeutic agent, in combination with a peptide of the present invention. Chemotherapeutic agents include any antineoplastic drug or chemical, such as for example alkylating agents, antimetabolites, anthracyclines, plant alkaloids, topoisomerase inhibitors, and other antitumor agents. Non-limiting examples of alkylating agents include cisplatin, carboplatin, oxaliplatin, mechlorethamine, cyclophosphamide, chlorambucil and ifosfamide; examples of antimetabolites include azathioprine and mercaptopurine; examples of anthracyclines include daunorubicin, doxorubicin, epirubicin, idarubicin, valrubicin and mitoxantrone; examples of plant alkaloids include *vinca* alkaloids such as vincristine, vinblastine, vinorelbine and vindesine and taxanes such as paclitaxel and docetaxel; examples of topoisomerase inhibitors include camptothecins such as irinotecan and topotecan and type II topoisomerases such as amsacrine, etoposide, etoposide phosphate and teniposide. However, any agent suitable for use in targeted cytotoxic therapy may be so employed. Non-limiting examples of radiation therapeutic agents that may be so employed include $^{131}$I, $^{125}$I, $^{211}$At, $^{186}$Re, $^{188}$Re, $^{90}$Y $^{153}$Sm, $^{212}$Bi and $^{32}$P, among others.

Diagnostic imaging or cytotoxic therapy agents may be incorporated into a peptide of the present invention, for example such as by use of $^{11}$C, $^{13}$N, $^{15}$O, among others, in place of nonradioactive isotopes; may be linked directly to a peptide of the present invention, such as for example by halogenation or other direct complexation methods; or may be linked indirectly to a peptide of the present invention, such as conjugation by means of a linker or chelation unit. Linker units are well known in the art, and include, but are not limited to, chemically-linked conjugates including at least one disulfide bond, thioether bond or covalent bond between free reactive groups. Representative cross-linking and conjugating reagents are disclosed in U.S. Pat. Nos. 7,169,603, 7,820,164 and 5,443,816 and US Publication No. 2009/0297444, among others, incorporated herein by reference.

3.0 Combination Therapy for Certain Indications

The peptides, compositions and methods of the present invention may be used for treatment of any of the foregoing diseases, indications, conditions or syndromes, or any disease, indication, condition or syndrome which is MC1r mediated or responsive, by administration in combination with one or more other pharmaceutically active compounds. Such combination administration may be by means of a single dosage form which includes both a peptide of the present invention and one more other pharmaceutically active compounds, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. The term “coadminister” indicates that each of at least two compounds in the combination therapy are administered during a time frame wherein the respective periods of biological activity or effects overlap. Thus the term includes sequential as well as concurrent administration of compounds where one compound is one or more of the peptides of the present invention. If more than one compound is coadministered, the routes of administration of the two or more compounds need not be the same. Without meaning to limit combination therapies, the following exemplifies certain combination therapies which may be employed.

3.1 Combination Therapy with Anti-Inflammatory Agents

For the treatment of inflammation-related diseases, indications, conditions and syndromes, peptides of the present invention may be used in combination therapy, including by means of coadministration, with one or more anti-inflammatory agents. One class of anti-inflammatory agent is glucocorticoids, including but not limited to cortisone, including cortisone acetate, hydrocortisone, prednisone, prednisolone, methylprednisolone, dexamethasone, betamethasone, triamcinolone, beclometasone, prednisone, fludrocortisone acetate, deoxycorticosterone acetate and aldosterone. Other anti-inflammatory agents that may be used in combination therapy, including by means of coadministration, include aspirin, non-steroidal antiinflammatory drugs (NSAIDs) (such as ibuprofen and naproxin), TNF-α inhibitors (such as tenidap and rapamycin or derivatives thereof), or TNF-α antagonists (e.g., infliximab, OR1384), cyclooxygenase inhibitors (i.e., COX-1 and/or COX-2 inhibitors such as Naproxen® or Celebrex®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, prostaglandin synthesis inhibitors, budesonide, clofazimine, p38 mitogen-activated protein kinase inhibitors, protein tyrosine kinase (PTK) inhibitors, IKK inhibitors, therapies for the treatment of irritable bowel syndrome (e.g., Zelmac® and Maxi-K® openers such as those disclosed in U.S. Pat. No. 6,184,231), or other NF-κB inhibitors, such as corticosteroids, calphostin, CSAIDs, 4-substituted imidazo [1,2-A]quinoxalines as disclosed in U.S. Pat. No. 4,200,750; Interleukin-10, salicylates, nitric oxide, and other immunosuppressants; and nuclear translocation inhibitors, such as deoxyspergualin (DSG).

3.2 Combination Therapy with Phosphodiesterase Inhibitors

For certain applications and indications, it is desirable to increase production of and maintain levels of cyclic adenoise 3',5' monophosphate (cAMP), a nucleotide messenger associated with inflammatory cell activity. Peptides of the present invention increase intracellular levels of cAMP and can be coadministered with compounds or substances that inhibit the degradation of cAMP. cAMP is hydrolyzed to an inactive form by phosphodiesterase (PDE); compounds or substances that inhibit PDE may thereby result in maintenance of and/or an increase in available cAMP. A class of compounds known as PDE inhibitors has been extensively studied for use in treatment of inflammatory diseases, such as asthma, COPD and acute respiratory distress syndrome. Preferred are inhibitors of PDE type 1, 2, 3, 4, 7, 8, 10 or 11; in one aspect this includes cAMP-PDE inhibitors that are selective PDE type 4 inhibitors or inhibitors having selectivity for one particular type of PDE 4 isoenzyme, such as, by way of example, rolipram, cilomilast, ibudilast, and piclamilast.

3.3 Combination Therapy in Ocular Indications

For ocular indications, an ophthalmic dosage form may include one or more active ingredients in addition to one or more of the peptides of the present invention, such as for example artificial tear components, topical corticosteroids, non-steroidal anti-inflammatory drugs, or calcineurin inhibitors such as cyclosporine-A ophthalmic emulsion (Restasis®—Allergan). It is also possible that coadministration includes administration of one or more additional compounds given separately from a peptide of the present invention, such as separate administration of an ophthalmic dosage form including an artificial tear component, a topical corticosteroid, a non-steroidal anti-inflammatory drugs, a calcineurin inhibitor such a cyclosporine-A, or a combination of any of the foregoing.

Combination ophthalmic solutions may be employed, including specifically solutions including more than one active pharmaceutical ingredient. In one aspect, a non-steroidal anti-inflammatory drug (NSAID) is employed in combination with a peptide of the present invention. NSAIDs suitable for use in combination ophthalmic solutions include agents, their esters and pharmaceutically acceptable salts thereof that inhibit the cycloxygenase (COX)-1 and/or -2 enzyme, including but not limited to propionic acid compounds such as naproxen, flurbiprofen, oxaprozin, ibuprofen, ketoprofen, fenoprofen; ketorolac tromethamine; acetic acid derivatives such as sulindac, indomethacin, and etodolac; phenylacetic acids such as diclofenac, bromfenac, and suprofen; arylacetic prodrugs such as nepafenac, and amfenac; salicyclic acids, such as aspirin, salsalate, diflunisal, choline magnesium trisalicylate; para-aminophenol derivatives such as acetaminophen; naphthylalkanones such as nabumetone; enolic acid derivatives such as piroxicam and meloxicam; femanates such as mefenamic acid, meclofenamate and flufenamic acid; pyrroleacetic acids such as tolmetin; and pyrazolones such as phenylbutazone; and COX-2 selective inhibitors such as celecoxib, valdecoxib, parecoxib, etoricoxib, and luaricoxib. The ophthalmic solutions may additionally comprise other active ingredients, including, but not limited to, vasoconstrictors, anti-allergenic agents, anti-infectives, steroids, anesthetics, anti-inflammatories, analgesics, dry eye treatment agents (e.g. secretagogues, mucomimetics, polymers, lipids, antioxidants), and the like, or be administered in conjunction (simultaneously or sequentially) with pharmaceutical compositions comprising other active ingredients, including, but not limited to, vasoconstrictors, anti-allergenic agents, anti-infectives, steroids, anesthetics, anti-inflammatories, analgesics, dry eye treatment agents (e.g. secretagogues, mucomimetics, polymers, lipids, antioxidants), and the like.

3.4 Combination Therapy in Shock-Related Indications

The methods of treating or preventing circulatory shock of the present invention also relate to coadministering one or more substances to the subject in addition to one or more of the peptides of the present invention. For example, one or more of the peptides of the present invention may be coadministered with androstenetriol, androstenediol or derivatives thereof, various vasopressin agonists, or other pharmaceutically active substances, such as catecholamines or other a adrenergic agonists, $\alpha_2$ adrenergic agonists, p adrenergic agonists or $\beta_2$ adrenergic agonists, including but not limited to epinephrine, norepinephrine, dopamine, isoproterenol, vasopressin and dobutamine. Alternatively, one or more of the peptides of the present invention may be coadministered with fluids or other substances that are capable of alleviating, attenuating, preventing or removing symptoms in a subject suffering from, exhibiting the symptoms of, or at risk of suffering from hypovolemic shock, vasodilatory shock or cardiogenic shock. Types of fluid that can be coadministered with one or more of the peptides of the present invention should be specific to the circumstances surrounding the particular subject that is suffering from, exhibiting the symptoms of, or at risk of suffering from shock. For example, fluids that may be coadministered with one or more of the peptides of the present invention include, but are not limited to, salt solutions—such as sodium chloride and sodium bicarbonate—as well as whole blood, synthetic blood substitutes, plasma, serum, serum albumin and colloid solutions. Colloid solutions include, but are not limited to, solutions containing hetastarch, albumin or plasma. In one particular embodiment of the present invention, fluids such as one or more of salt solutions, colloidal solutions, whole blood, synthetic blood substitutes, plasma or serum are coadministered with one or more of the peptides of the present invention in patients suffering from or exhibiting the symptoms of a hypovolemic shock, such as hemorrhagic shock.

3.5 Combination Therapy for Obesity and Related Metabolic Syndrome

One or more peptides of the invention may be combined with one or more other pharmacologically active agent(s) that is (are) useful in the treatment of various weight and feeding-related disorders, such as obesity and/or overweight, in particular other anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioral therapy in weight reduction programs.

Generally, a total dosage of the below-described obesity control agents or medications, when used in combination with one or more peptides of the present invention can range from 0.01 to 3,000 mg/day, preferably from about 0.1 to 50 mg/day and more preferably from about 0.1 to 10 mg/day in single or 2-4 divided doses. The exact dose, however, is determined by the attending clinician and is dependent on such factors as the potency of the compound administered, the age, weight, condition and response of the patient.

One or more peptides of the invention may be combined with one or more other pharmacologically active agent(s) that is (are) useful in the treatment of diabetes, such as other anti-diabetic drugs.

One or more peptides of the invention may in addition or alternatively further be combined with one or more other pharmacologically active agent(s) that is (are) useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

According to a further aspect of the invention there is provided a combination treatment comprising the administration of a pharmacologically effective amount of a peptide according to the invention, or a pharmaceutically acceptable salt thereof, optionally together with a pharmaceutically acceptable diluent or carrier, with the simultaneous, sequential or separate administration one or more of the following agents selected from:

- insulin and insulin analogues;
- insulin secretagogues, including sulphonylureas (e.g. glipizide) and prandial glucose regulators (sometimes called "short-acting secretagogues"), such as meglitinides (e.g. repaglinide and nateglinide);
- agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide);
- insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;
- agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;

agents designed to reduce/slow the absorption of glucose from the intestine, such as alpha-glucosidase inhibitors (e.g. miglitol and acarbose);

agents which antagonise the actions of or reduce secretion of glucagon, such as amylin analogues (e.g. pramlintide);

agents that prevent the reabsorption of glucose by the kidney, such as sodium-dependent glucose transporter 2 (SGLT-2) inhibitors (e.g. dapagliflozin);

agents designed to treat the complications of prolonged hyperglycaemia, such as aldose reductase inhibitors (e.g. epalrestat and ranirestat); and agents used to treat complications related to micro-angiopathies;

anti-dyslipidemia agents, such as HMG-CoA reductase inhibitors (statins, e.g. rosuvastatin) and other cholesterol-lowering agents; PPARα agonists (fibrates, e.g. gemfibrozil and fenofibrate); bile acid sequestrants (e.g. cholestyramine); cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants, such as probucol; and omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem); angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide);

haemostasis modulators, including antithrombotics, such as activators of fibrinolysis; thrombin antagonists; factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);

anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant);

feeding behavior modifying agents, such as orexin receptor modulators and melanin-concentrating hormone (MCH) modulators;

glucagon like peptide-1 (GLP-1) receptor modulators;

neuropeptideY (NPY)/NPY receptor modulators;

pyruvate dehydrogenase kinase (PDK) modulators;

serotonin receptor modulators;

leptin/leptin receptor modulators;

ghrelin/ghrelin receptor modulators; or monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

According to a further aspect of the present invention there is provided a combination treatment comprising the administration of a pharmacologically effective amount of a compound according to the invention, or a pharmaceutically acceptable salt thereof, optionally together with a pharmaceutically acceptable carrier, with the simultaneous, sequential or separate administration of very low-calorie diets (VLCD) or low-calorie diets (LCD).

According to an additional further aspect of the present invention, as disclosed in WO2016/168388, "Therapies for Obesity, Diabetes and Related Indications," which is incorporated herein by reference, one or more peptides of the invention, and preferably a peptide that is a MC4r agonist, may be administered in conjunction with a GLP-1 receptor agonist. Thus, the invention herein includes a pharmaceutical composition for subcutaneous administration in treatment of obesity or to induce weight loss, comprising on a per dose basis:

a peptide of the invention that is an MC4r agonist in a quantity sufficient to induce at least minimal weight loss when administered as a monotherapy not in conjunction with a GLP-1 receptor agonist; and a GLP-1 receptor agonist in a quantity sufficient to induce glycemic control but not weight loss when administered as a monotherapy not in conjunction with the MC4r agonist, wherein the pharmaceutical composition preferably has a synergistic anti-obesity effect.

In a related aspect, the invention provides a method of treating a patient with obesity, diabetes or metabolic syndrome, comprising administering to the patient (a) a peptide of the invention that is an MC4r agonist in a quantity sufficient to induce at least minimal weight loss when administered as a monotherapy not in conjunction with a GLP-1 receptor agonist and (b) a GLP-1 receptor agonist in a quantity sufficient to induce glycemic control but not weight loss when administered as a monotherapy not in conjunction with the MC4r agonist. Preferably the method elicits a synergistic effect on treatment of obesity.

In another aspect, the invention provides a method of decreasing side effects associated with therapeutic agents for treatment of obesity, diabetes or metabolic syndrome in a patient, comprising:

administration of a quantity of a peptide of the invention that is an MC4r agonist, wherein the quantity of MC4r agonist peptide administered, if administered as a monotherapy not in conjunction with GLP-1 receptor agonist, is not sufficient to initiate the desired pharmacological response in treating at least one condition from the group comprising obesity, diabetes and metabolic syndrome in the patient when administered as a monotherapy; and administration of a quantity of GLP-1 receptor agonist, wherein the quantity of GLP-1 receptor agonist administered, if administered as a monotherapy not in conjunction with the MC4r agonist, is not sufficient to initiate the desired pharmacological response in treating at least one condition from the group comprising obesity, diabetes and metabolic syndrome in the patient when administered as a monotherapy;

wherein the quantity of the MC4r agonist and the quantity of GLP-1 receptor agonist are together effective to initiate the desired pharmacological response treating at least one condition from the group comprising obesity, diabetes and metabolic syndrome in the patient, thereby reducing side effects in the treatment of at least one of obesity, diabetes or metabolic syndrome in the patient.

3.6 Combination Therapy for Sexual Dysfunction

It is also possible and contemplated to use cyclic peptides of the present invention in combination with other drugs or agents, such as for treatment of sexual dysfunction. These other drugs and agents may include agents that induce erectile activity, including phosphodiesterase-5 (PDE-5) inhibitors, testosterone, prostaglandin and the like. In a preferred embodiment of the invention, cyclic peptides of the invention are used in combination with a therapeutically effective amount of a cyclic-GMP-specific phosphodiesterase inhibitor or an alpha-adrenergic receptor antagonist. The teachings and disclosure of U.S. Pat. No. 7,235,625, entitled "Multiple Agent Therapy for Sexual Dysfunction," are incorporated here by reference as if set forth in full.

The present invention thus provides methods of treating sexual dysfunction, the methods comprising the step of administering to the patient having or at risk of having sexual dysfunction a therapeutically effective amount of a cyclic peptide of the present invention in combination with a therapeutically effective amount of a second sexual dysfunction pharmaceutical agent. The cyclic peptide of the present invention may be administered simultaneously with, prior to or subsequent to administration with a therapeutically effective amount of a second sexual dysfunction pharmaceutical agent. Preferably the peptide of the present invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptide of the present invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptide of the present invention when desired or needed by the patient.

The present invention thus provides methods of treating sexual dysfunction, the methods comprising the step of administering to a patient having or at risk of having sexual dysfunction a therapeutically effective amount of a cyclic peptide of the present invention in combination with another compound that is useful in the treatment of sexual dysfunction. In a preferred embodiment of combination therapy, the sexual dysfunction is female sexual dysfunction, including but not limited to hypoactive sexual desire disorder. In another preferred embodiment of combination therapy the sexual dysfunction is erectile dysfunction.

The present invention also provides pharmaceutical compositions that comprise a cyclic peptide of the present invention and a second compound useful for the treatment of sexual dysfunction. In an embodiment of the composition, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphine; oxytocin modulators; α-adrenergic antagonists; androgens; selective androgen receptor modulators (SARMs); buproprion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase (PDE-5) inhibitor. For example, the PDE-5 inhibitor may be Viagra®, a brand of sildenafil, Levitra®, a brand of monohydrochloride salt of vardenafil, or Cialis®, a brand of tadalafil. Other PDE-5 inhibitors are disclosed in U.S. Pat. No. 7,235,625, issued Jun. 22, 2007, and entitled "Multiple Agent Therapy for Sexual Dysfunction", incorporated here by reference.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napththalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a cyclic peptide of the present invention may be used in combination with any known mechanical aids or devices.

4.0 Methods of Administration and Use

The method of administration and use varies depending upon the characteristic of specific peptides disclosed herein, or of a formula disclosed herein, the disease, indication, condition or syndrome to be treated, and other factors known to those in the art. In general, any method of administration and use known in the art or hereafter developed may be employed with the peptides disclosed herein, or of a formula disclosed herein. Without limiting the foregoing, the following methods of administration and use have specific application for the indicated indications.

4.1 Subcutaneous Injection Use

In one aspect, a composition including one or more peptides of the present invention is formulated for subcutaneous injection, and a subcutaneous injection is given at specified intervals, such as weekly or one or more times each day. In another aspect, the composition is formulated as an injectable sustained release formulation. In one embodiment, a peptide of the present invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a peptide of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a peptide of the present invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a sustained release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of peptide, the biodegradation rate of the polymer, and other factors known to those of skill in the art.

4.2 Inhalation Use

In one aspect, a composition including one or more peptides of the present invention is formulated for administration to the respiratory tract, such as in the form of an aerosol or solution for a nebulizer, or as a microfine powder for insufflation or inhalation (e.g., topically to the lung and/or airways), alone or in combination with one or more inert carriers or additional active pharmaceutical ingredients, and in the form of a solution, a suspension, an aerosol or a dry powder formulation. See generally, Cryan, S.-A., "Carrier-based strategies for targeting protein and peptide drugs to the lungs," *The AAPS Journal* 7:E20-41 (2005). In general, the peptides of the present invention may be used the devices, formulations, compositions and means described in one or more of the following U.S. patents or patent applications, each of which is incorporated herein by reference: U.S. Pat. Appl. No. 20090241949, "Dry powder inhalation system"; U.S. Pat. Appl. No. 20080066741, "Methods and systems of delivering medication via inhalation"; U.S. Pat. Appl. No. 20070298116, "Amorphous, spray-dried powders having a reduced moisture content and a high long term stability"; U.S. Pat. Appl. No. 20070140976, "Aqueous inhalation pharmaceutical composition"; U.S. Pat. Appl. No. 20060054166, "Inhalation nebulizer"; U.S. Pat. Appl. No. 20050211244, "Dry powder preparations"; U.S. Pat. Appl. No. 20050123509. "Modulating charge density to produce improvements in the characteristics of spray-dried proteins"; U.S. Pat. Appl. No. 20040241232, "Dry powder medicament formulations"; U.S. Pat. No. 7,582,284, "Particulate materials"; U.S. Pat. No. 7,481,212, "Increased dosage metered dose inhaler"; U.S. Pat. No. 7,387,794, "Preparation of powder agglomerate"; U.S. Pat. No. 7,258,873, "Preservation of bioactive materials by spray drying"; U.S. Pat. No. 7,186,401, "Dry powder for inhalation"; U.S. Pat. No. 7,143,764, "Inhalation device"; U.S. Pat. No. 7,022,311, "Powdery inhalational preparations and process for producing the same"; U.S. Pat. No. 6,962,151, "Inhalation nebulizer"; U.S. Pat. No. 6,907,880, "Inhalation device"; U.S. Pat. No. 6,881,398, "Therapeutic dry powder preparation"; U.S. Pat. No. 6,698,425, "Powder inhaler"; U.S. Pat. No. 6,655,380, "Inhalation device"; U.S. Pat. No. 6,645,466, "Dry powder for inhalation"; U.S. Pat. No. 6,632,456, "Compositions for inhalation"; U.S. Pat. No. 6,610,272, "Medicinal aerosol formulation"; U.S. Pat. No. 6,596,261, "Method of administering a medicinal aerosol formulation"; U.S. Pat. No. 6,585,957, "Medicinal aerosol formulation"; U.S. Pat. No. 6,582,729, "Powered pharmaceutical formulations having improved dispersibility"; U.S. Pat. No. 6,572,893, "Systems and processes for spray drying hydrophobic drugs with hydrophilic excipients"; U.S. Pat. No. 6,551,578, "Modulated release particles for aerosol delivery"; U.S. Pat. No. 6,520,179, "Inhalation device"; U.S. Pat. No. 6,518,239, "Dry powder compositions having improved dispersivity"; U.S. Pat. No. 6,503,481, "Compositions for aerosolization and inhalation"; U.S. Pat. No. 6,358,530, "Powdered pharmaceutical formulations having improved dispersibility"; U.S. Pat. No. 6,325,061, "Inhalation device"; U.S. Pat. No. 6,257,232, "Inhalation device"; U.S. Pat. No. 6,187,344, "Powdered pharmaceutical formulations having improved dispersibility"; U.S. Pat. No. 6,116,237, "Methods of dry powder inhalation"; U.S. Pat. No. 5,934,272, "Device and method of creating aerosolized mist of respiratory drug"; and, U.S. Pat. No. 5,558,085, "Intrapulmonary delivery of peptide drugs".

The composition may be a dry powder composition for topical delivery to the lung by inhalation. The composition may contain a powder mix for inhalation of a peptide of the present invention and a suitable powder base, diluent or carrier substance such as lactose, glucose, dextran, mannitol or another sugar or starch. The composition may be used in any of a variety of dry powder devices, such as a reservoir dry powder inhaler, a multi-dose dry powder inhaler, or a metered dose inhaler. The composition may include additional excipients, such as an alcohol, a surfactant, a lubricant, an anti-oxidant or a stabilizing agent. Suitable propellants include hydrocarbon, chlorofluorocarbon and hydrofluoroalkane propellants, or mixtures of any such propellants.

Inhalation solutions also can be formulated in a liquefied propellant for aerosol delivery, such as with a pressurized metered dose inhaler. In yet another formulation, solutions may be in the form of a nebulised aqueous suspension or solution, with or without a suitable pH or tonicity adjustment, either as a single dose or multidose device.

4.3 Nasal Delivery

Formulations or compositions suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. Alternatively, suitable formulations may comprise a liquid carrier, as for example a nasal spray or nasal drops, which may comprise aqueous or oily solutions of the active ingredients.

4.4 Buccal and Mucosal Membrane Delivery

Pharmaceutical compositions may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Furthermore, one or more other active ingredients may (but need not) be included in the pharmaceutical compositions provided herein.

4.5 Oral Delivery

In one aspect, a peptide of the present invention that comprises an MC1r agonist is orally administered and delivered substantially intact to the lumen of all or a portion of the intestinal tract, including in certain aspects the colon of a patient, for treatment of an inflammatory bowel disease, colitis or other melanocortin receptor-mediated or responsive diseases, indications, conditions and syndromes of the gastrointestinal tract. A delay release polymer formulation comprising the peptide of the present invention, including but not limited to a pH-dependent release polymer, may be employed. The teachings and disclosure of International Publication Number WO 2019/183472, filed as International Application Number PCT/US2019/023575, and entitled "Melanocortin Receptor-Specific Formulations and Methods for Gastrointestinal Tract-Specific Delivery," are incorporated herein by reference as if set forth in full.

For systemic administration, compositions including one or more peptides disclosed herein, or of a formula disclosed herein, may be administered orally in an individual dosage form such as a tablet or capsule. In one preferred aspect, the individual dosage form includes an enteric coating, and optionally one or more agents to increase uptake, decrease protease degradation, increase cellular permeability, and the like. Any of a variety of delivery technologies, including but not limited to liposomal compositions, muco-adhesive or gastroretentive delivery systems, absorption enhancers, multifunctional drug delivery systems, co-administration of permeation enhancers and/or protease inhibitors, covalent conjugation with various chemical or biological adjuncts, such as to increase cell-penetrating capabilities, enteric coatings, various nanoparticles and the like, may be employed in oral delivery of peptides of this invention.

5.0 Methods of Making

In general, the peptides disclosed herein, or of a formula disclosed herein, may be synthesized by any means known in the art, including by solid-phase synthesis, and may be purified according to methods known in the art. Any of a number of well-known procedures utilizing a variety of resins and reagents may be used to prepare the peptides disclosed herein, or of a formula disclosed herein.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods.

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods. Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbonyl, and allyloxycarbonyl (Alloc). Fmoc is particularly suitable for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arg. Other reactive groups, including amines and carboxylic acid groups, may similarly be protected, such as for example 1-tert-butyl ester (OtBu) for Glu, Boc for Trp, trityl (Trt) for His and the like.

The linear peptide precursors of the peptides of the invention described herein were prepared using solid phase synthesis with an automated peptide synthesizer, using programming modules as provided by the manufacturer and following the protocols set forth in the manufacturer's manual.

Solid phase synthesis is commenced from the C-terminal end of the peptide. In one aspect, the diamine linker or diamine ether linker is coupled to a suitable resin, thereby forming a starting resin, and a protected alpha amino acid is then coupled to the diamine or diamine ether linker. For example, such starting material may be prepared by attaching an alpha amino-protected amino acid by a diamine or diamine ether linker to a p-benzyloxybenzyl alcohol (Wang) resin, a 2-chlorotrityl chloride resin or an oxime resin. Diamine and diamine ether trityl resins are commercially available and generally used when commercially available.

The cyclic peptides disclosed herein, or of a formula disclosed herein, may be readily synthesized by known conventional procedures for the formation of a peptide linkage between amino acids. Such conventional procedures include, for example, any solution phase procedure permitting a condensation between the free alpha amino group of an amino acid residue having its carboxyl group and other reactive groups protected and the free primary carboxyl group of another amino acid residue having its amino group or other reactive groups protected. In a preferred conventional procedure, the cyclic peptides disclosed herein, or of a formula disclosed herein, may be synthesized by solid-phase synthesis and purified according to methods known in the art. Any of a number of well-known procedures utilizing a variety of resins and reagents may be used to prepare the peptides disclosed herein, or of a formula disclosed herein.

The process for synthesizing the cyclic peptides may be carried out by a procedure whereby each amino acid residue in the desired sequence is added one at a time in succession to another amino acid residue or by a procedure whereby peptide fragments with the desired amino acid sequence are first synthesized conventionally. The resulting linear peptide is then cyclized in solution phase to yield a cyclic peptide of the invention.

In one aspect, solid-phase synthesis is employed to make the peptides of this invention. In this method, N-terminal protecting groups (PG) may be employed, such as Fmoc or Boc, depending on the protecting group scheme employed. Amino acid side chains with reactive groups may further be orthogonally protected, as for example Trp(Boc), Arg(Pbf), His(Trt), Glu(OtBu) and the like. Typically protecting groups are selected such that upon cleavage of the peptide from the solid-phase resin the peptide is globally deprotected, including removal of orthogonal protecting groups.

The solid support (shown in the diagram below by the bolded circle) is a small, polymeric resin bead, functionalized with the desired reactive group. In one aspect the reactive group comprises a diamine group, preferably selected from the group comprising:

—NH—$(CH_2)_{2-8}$—NH— or

—NH—$(CH_2)_{2-5}$—O—$(CH_2)_{2-5}$—NH—.

In the scheme shown below, the reactive diamine group depicted is —NH—$(CH_2)_{2-8}$—NH—, but it is to be understood that the reactive group —NH—$(CH_2)_{2-5}$—O—$(CH_2)_{2-5}$—NH— may similarly be employed.

Each amino acid to be couple to the peptide chain N-terminus must be protected on its N-terminus and, if the amino acid contains a reactive group, on its side chain. The employs an amide resin, in one embodiment of the present invention a resin with a diamine linker, which diamine linker may comprise —NH—$(CH_2)_{2-8}$—NH— or —NH—$(CH_2)_{2-5}$—O—$(CH_2)_{2-5}$—NH—, is employed.

In one embodiment preloaded trityl groups are employed for ease of synthesis; by way of example and not limitation, the starting resin may be a trityl resin which further comprises a diamine linker group, such as:

1,4-diaminobutane trityl resin (Chemlmpex, Cat. No. 04303), 1,2-diaminoethane trityl resin (Chemlmpex, Cat. No. 04306), or 1,5-diaminopentane trityl resin (Chemlmpex, Cat. No. 04308).

However, other resins may be employed, and other diamine or diamine ether linker groups may be employed. As necessary, specific resins may be made to provide the desired diamine linker group. In one aspect, a resin such as 2-chloro-trityl is utilized, and the initial step is linking the selected diamine or diamine ether linker group to the resin, and thereafter commencing synthesis.

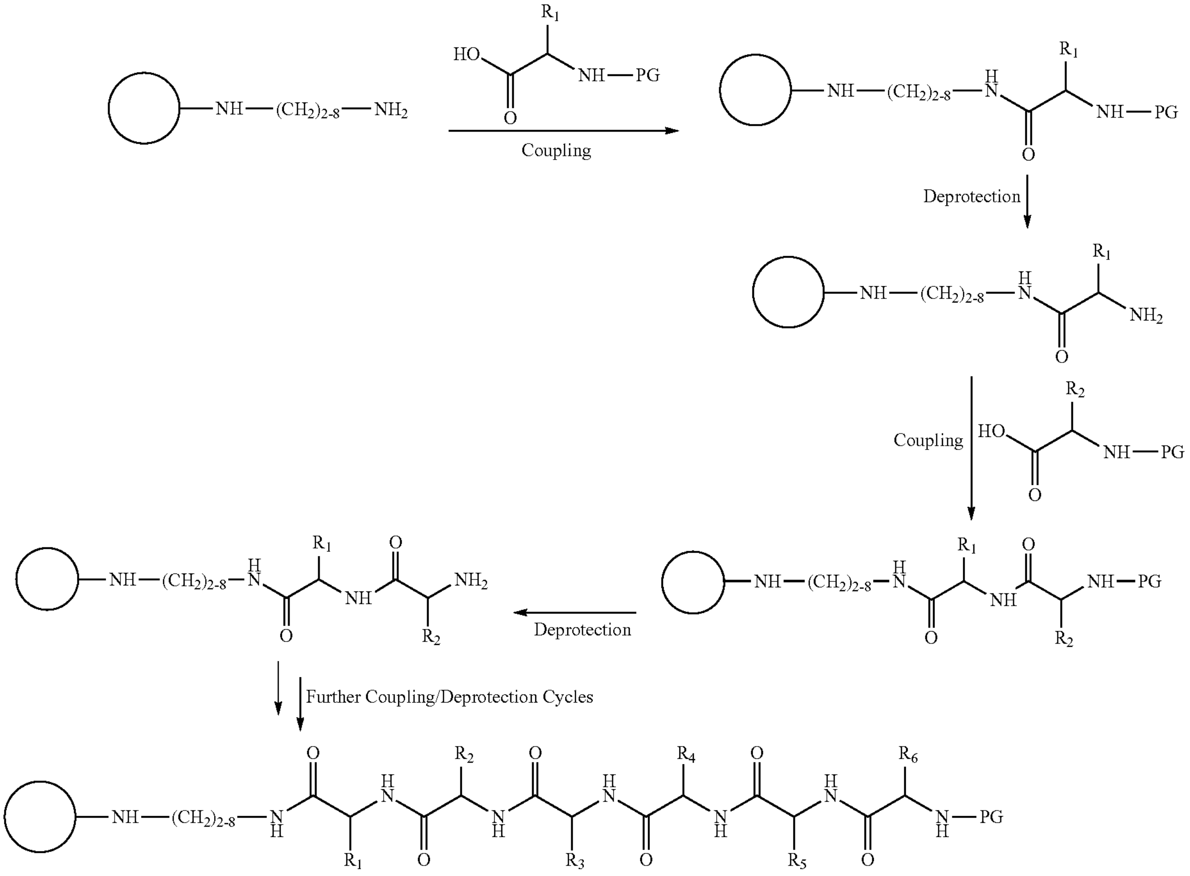

N-terminus may be protected by using any appropriate protecting group; Boc and Fmoc are protecting groups commonly employed in solid phase peptide synthesis and may similarly be employed in the practice of this invention. As may be seen below, the solid phase peptide synthesis proceeds conventionally, by repeated cycles of alternate N-terminal deprotection and coupling reactions. However, unlike conventional solid phase peptide synthesis, which By way of example, the starting resin 1,4-diaminobutane trityl resin (Chemlmpex, Cat No. 04303, 0.77 mmol/g, 0.4 mmol), is loaded onto a peptide synthesizer. The next sequential amino acid residue is the carboxy-terminal amino acid, which may be, for example, Trp. In that case, a protected Trp is employed, such as Trp(Boc), resulting in -Trp(Boc)-NH—$(CH_2)_4$—NH-resin following deprotection of the -Trp(Boc) protecting group. It may readily be seen that other diamine linkers may be employed, and similarly diamine ether linkers may be employed.

Each deprotection step may comprise, for example, the use of piperidine, 1,8-diazabicyclo[5.4.0]undec-7-ene (DBU), 1-hydroxybenzotriazole (HOBT), N,N-dimethylformamide (DMF) and the like, followed by wash cycles, such as with DMF or methyl tert-butyl ether (MBTE), with repeat cycles as appropriate.

Each coupling step may comprise, for example, the use of the desired protected amino acid, such as an Fmoc-AA-OH, with coupling reagents including dichloromethane (DCM), HOBT, N,N-diisopropylethylamine (DIPEA), DMF, or 2-(1H-benzotriazol-1-yl)-1,1,3,3-tetramethyluronium hexafluorophosphate (HBTU), among others. Following coupling wash cycles may be employed, such as with DMF or MBTE.

While the synthesized peptide is coupled to resin or in solution, the N-terminus may be modified, such as by acetylation. In one aspect, a method is employed wherein after removal of the protecting group at the N-terminal, the resin-bound peptide is reacted with acetic anhydride in dichloromethane in the presence of an organic base, such as diisopropylethylamine. Other methods of N-terminus acetylation are known in the art, including solution phase acetylation, and may be employed.

The resulting resin-bound peptide may be cleaved from resin by any means known in the art, such as mixing the resin-bound peptide with a mixture of trifluoroacetic acid (TFA), tri-isopropylsilane (TIS) and water, such as TFA/TIS/$H_2O$ (95:2.5:2.5, v/v/v), for a suitable period, such as 20 minutes, at a suitable temperature, such as room temperature. As desired, one or more additional cycles of mixing the resin-bound peptide with the mixture of TFA/TIS/$H_2O$ may be conducted following filtration. Combined filtrates may be stored, such as at room temperature for a period of two hours, and then may be concentrated by purging with an $N_2$ stream. The cleaved linear peptide may then be precipitated from cold ether, with the resulting residue then dissolved in 50% t-butanol/water and lyophilized to yield linear peptide.

The resulting crude linear peptide may then be cyclized in solution by conventional reaction means for cyclization through amide bond condensation. The linear peptides are first dissolved in suitable solvents, such as DMF, tetrahydrofuran (THF), DCM or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), HBTU, benzotriazole-1-yl-oxy-tris (dimethylamino)phosphoniumhexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is conventionally initiated by use of a suitable base, such as DIPEA, sym-collidine or N-methylmorpholine (NMM).

Following the solution cyclization, the resulting mixture may be concentrated by means known, and may then be partially purified such as by trituration utilizing methyl tert-butyl ether (MTBE). Resulting fractions may then be pooled and lyophilized.

For peptide No. 60 of this invention, synthesis commenced with loading a starting resin of 1,4-diaminobutane trityl resin (Chemlmpex, Cat. No. 04303, 0.77 mmol/g, 0.4 mmol) onto a peptide synthesizer. The amino acids Fmoc-Trp(Boc), Fmoc-Arg(Pbf), Fmoc-D-Phe(4-F), Fmoc-His (Trt), Fmoc-Glu(OtBu) and Fmoc-Nle were individually coupled in order, with deprotection following each individual coupling, with the Fmoc-Nle deprotected and the resulting amine acylated, such as by use of acetic anhydride and pyridine in DMF for a suitable period, to yield the orthogonally-protected resin-bound linear peptide:

Ac-Nle-Glu(OtBu)-His(Trt)-D-Phe(4-F)-Arg(Pbf)-Trp (Boc)-$NH(CH_2)_4NH$-Resin (SEQ ID NO:4)

The peptide-resin was mixed with 8 mL of cleavage solution comprising TFA/TIS/$H_2O$ (95:2.5:2.5, v/v/v) for 20 minutes, which also cleaved the orthogonal protecting groups. Mixing was then repeated by mixing with 8 mL fresh cleavage solution for an additional 20 minutes. Combined filtrates were stored at room temperature for two hours before being concentrated to about 25 mL by use of a purging $N_2$ stream. The cleaved linear peptide was precipitated from cold ether. The residue was dissolved in 50% t-butanol/water and lyophilized to yield linear peptide (~0.4 mmol):

Ac-Nle-Glu-His-D-Phe(4-F)-Arg-Trp-$NH(CH_2)_4NH_2$ (SEQ ID NO:5)

The crude linear peptide was dissolved in mixture of 3 mL of DMF and 3 mL of DCM, and the resulting solution chilled in an ice cold water bath. To the cold solution was added 0.35 mL of EDC (0.18 g, 0.9 mmol) and HOAt (1.5 mL of 0.6 M solution in DMF, 0.9 mmol), followed by diisopropylethylamine (DIEA) (0.35 mL, 2.5 mmol) to pH 9. The reaction mixture was stirred while warming to room temperature, with continued stirring at room temperature overnight. LC/MS analysis showed cyclization was completed. 2 mL of 1N HCl was added to the reaction mixture and stirred for an additional two hours, and pH was then adjusted to pH 3 to pH 4. The pH adjusted reaction mixture was loaded directly to preparative HPLC, and resulting pure fractions were pooled and lyophilized, yielding 97.2 mg (yield 19.8%) of the cyclic peptide (SEQ ID NO: 51):

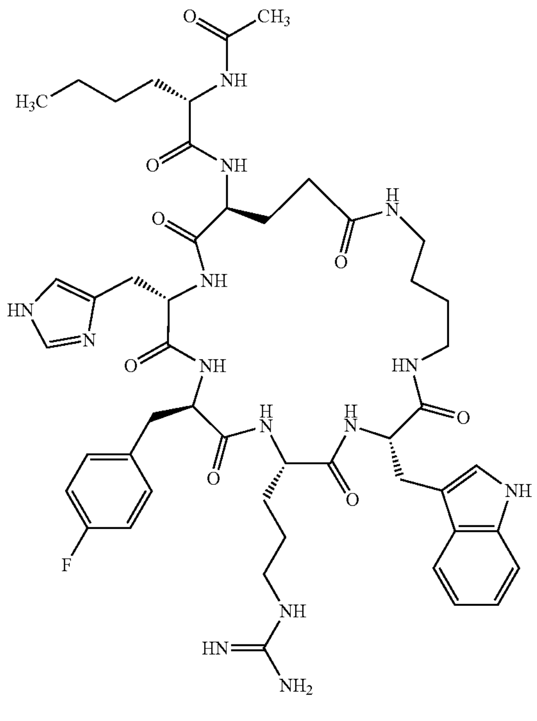 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O]

Final purification can also be by reverse phase high performance liquid chromatography (RP-HPLC), using a suitable column, such as a $C_{18}$ column, or other methods of separation or purification, such as methods based on the size or charge of the peptide, may also be employed. Once purified, the peptide can be characterized by any number of methods, such as high-performance liquid chromatography (HPLC), amino acid analysis, mass spectrometry, and the like.

Peptide No. 54 of this invention was synthesized as set forth above, substituting Met($O_2$) for His and D-Nal 1 for D-Phe(4-F). Following synthesis, cleavage from resin and global deprotection, cyclization of the crude linear peptide (~6 mmol) was initiated by mixing with PyBop (3.3 g, 6 mmol) in 200 mL of DMF/THF mixture (3:7, v/v), with the resulting suspension chilled in an ice cold water bath. A mixture of PyBop (6.4 g, 12 mmol) and NMM (6.52 mL, 59.4 mmol, 9.9 eq) in 40 mL of a mixture of DMF/THF (3:7, v/v) was added to the cold solution. This was allowed to react for 3 hours, and the reaction mixture was concentrated on a rotatory evaporator and then triturated with cold MTBE 3-4 times. The resulting oily residue was dissolved in 20 mL of 50% AcOH/water and stored overnight and then subjected to HPLC purification. Pure fractions were pooled and lyophilized, producing 670 mg of peptide No. 54 (yield 9.7%).

Peptides No. 71 and 72 of this invention were synthesized as set forth above for peptide No. 60, except that each consisted of five amino acids, with the N-terminus group being heptanoyl for peptide No. 71 and 3-phenylpropanoyl for peptide No. 72. In each instance, following synthesis, cleavage from resin and global deprotection, cyclization of the crude linear peptide (~3 mmol) was initiated by mixing with PyBop (1.6 g, 3 mmol) in 100 mL of DMF/THF mixture (3:7, v/v), with the resulting suspension chilled in an ice cold water bath. A mixture of PyBop (3.2 g, 6 mmol) and NMM (3.26 mL, 29.7 mmol, 9.9 eq) in 20 mL of a mixture of DMF/THF (3:7, v/v) was added to the cold solution. This was allowed to react for 3 hours, and the reaction mixture was concentrated on a rotatory evaporator and then triturated with cold MTBE 3-4 times. The oily residue was dissolved in 10 mL of 50% AcOH/water and stored overnight and then subjected to HPLC purification. Pure fractions were pooled and lyophilized to produce peptide No. 71 (312 mg, yield 8.8%), and peptide No. 72 (320 mg, yield 8.9%).

Peptide No. 77 was synthesized as set forth above for peptide No. 60, except that peptide No. 75 consisted of five amino acids, with the N-terminus group being 2-naphthylacetyl. Cyclization of the crude linear peptide (~4 mmol) was initiated by mixing with PyBop (4.16 g, 4 mmol) in 140 mL of DMF/THF mixture (3:7, v/v), with the resulting suspension chilled in an ice cold water bath. A mixture of PyBop (4.16 g, 8 mmol) and NMM (6.52 mL, 39.6 mmol, 9.9 eq) in 20 mL of a mixture of DMF/THF (3:7, v/v) was added to the cold solution. This was allowed to react for 3 hours, and the reaction mixture was concentrated on a rotatory evaporator and then triturated with cold MTBE 3-4 times. The oily residue was dissolved in 15 mL of 50% AcOH/water and stored overnight and then subjected to HPLC purification. Pure fractions were pooled and lyophilized to produce peptide No. 77 (586 mg, yield 11.8%).

Orthogonal protecting groups may also be used as appropriate. For example, the peptides of the invention contain multiple amino acids with an amino group-containing side chain. Any of a variety of protecting groups may be employed, including an Allyl-Alloc protection scheme with certain amino acids, and orthogonal protecting groups, cleavable under different reactive conditions, used for other amino acids with amino group-containing side chains. Thus, for example, Fmoc-Glu(OAll)-OH amino acids (Glu(OAll) refers to glutamic acid 5-allyl ester) can be employed for the position linked to the C-terminus diamine group upon cyclization, while other amino acids with amino group-containing side chains may have a different and orthogonal protecting group, such as with Fmoc-Arg(Pbf)-OH, Fmoc-Lys (Pbf)-OH, Fmoc-Dab(Pbf)-OH or the like. Other protecting groups may be similarly employed; by way of example and not limitation, Mtt (4-methyltrityl) or Mtt/OPp (4-methyltrityl/2-phenylisopropyl) can be employed with the side chain of His, with orthogonal protecting groups being utilized for other positions that are not cleavable using conditions suitable for cleavage of Mtt or Mtt/OPp.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

While synthesis has been described primarily with reference to solid phase Fmoc chemistry, it is to be understood that other chemistries and synthetic methods may be employed to make the cyclic peptides of the invention, such as by way of example and not limitation, any method that may be employed utilizing solid-phase peptide synthesis, methods employing Boc chemistry, solution chemistry, any of a variety of protecting groups schemes, fragment condensation, either on-resin or off-resin cyclization and other chemistries and synthetic methods.

6.0 Formulations

Depending on the desired route of administration, the formulation of a composition including one or more cyclic peptides disclosed herein, or of a formula disclosed herein, may be varied. Thus the formulation may be suitable for subcutaneous injection, slow-release subcutaneous injection, intravenous injection, for nasal spray applications, for inhalation applications, for oral administration, including but not limited to oral release for treatment of gastrointestinal diseases, for buccal or other mucosal applications, for other transdermal applications and the like. In general, formulations may be employed for any form of administration of a peptide of this invention.

6.1 Salt Form of Cyclic Peptides

The cyclic peptides disclosed herein, or of a formula disclosed herein, may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the cyclic peptides disclosed herein, or of a formula disclosed herein, is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, TFA, and the like. Acid addition salts of the peptides disclosed herein, or of a formula disclosed herein, are prepared in a suitable solvent from the peptide and an excess of an acid, such as hydrochloric, hydrobromic, sulfuric, phosphoric, acetic, TFA, citric, tartaric, maleic, succinic or methanesulfonic acid.

The acetate, ammonium acetate and TFA salt forms are especially useful. Where the peptides disclosed herein, or of a formula disclosed herein, include an acidic moiety, suitable pharmaceutically acceptable salts may include alkali metal salts, such as sodium or potassium salts, or alkaline earth metal salts, such as calcium or magnesium salts. It is also to be understood that certain peptides of formulas I through V can exist in solvated forms, including solvates of the free peptide or solvates of a salt of the compound, as well as unsolvated forms. The term "solvate" is used herein to describe a molecular complex comprising the compound of the invention and one or more pharmaceutically acceptable solvent molecules, for example, ethanol. The term "hydrate" is employed when said solvent is water. It is to be understood that all polymorphs, including mixtures of different polymorphs, are included within the scope of the claimed peptides.

6.2 Pharmaceutical Compositions

The invention provides a pharmaceutical composition that includes a cyclic peptide disclosed herein, or of a formula disclosed herein, and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions disclosed herein, or of a formula disclosed herein, may be formulated or compounded into pharmaceutical compositions that include at least one cyclic peptide disclosed herein, or of a formula disclosed herein, together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy propyl cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, cellulose derivatives, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or sustained-release formulations and additives may be employed, so that the dosage may be formulated so as to provide delivery of a peptide disclosed herein, or of a formula disclosed herein, over a period of time.

In general, the actual quantity of cyclic peptides disclosed herein, or of a formula disclosed herein, administered to a patient will vary between fairly wide ranges depending on the mode of administration, the formulation used, and the response desired.

In practical use, the cyclic peptides disclosed herein, or of a formula disclosed herein, can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another advantageous dosage unit form, sublingual constructs may be employed, such as sheets, wafers, tablets or the like.

The tablets, pills, capsules, and the like may also contain binders such as povidone, gum tragacanth, acacia, corn starch or gelatin; diluents; fillers such as microcrystalline cellulose; excipients such as dicalcium phosphate; disintegrating agents such as corn starch, potato starch or alginic acid; preservatives; colorants; lubricants such as magnesium stearate; and sweetening agents such as sucrose, lactose or saccharin. When a dosage unit form is a capsule, it may contain, in addition to materials of the above type, a liquid carrier such as fatty oil. Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

If formulated for oral delivery, the peptide may be formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will disintegrate after passing through the stomach to release the active drug substance. Materials that may be used includes cellulose acetate phthalate, hydroxypropylmethylethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach and may be selected such that the enteric coating dissolves at a pH of approximately at least 5.5, more preferable at a pH of from about 6.0 to about 8.0.

Any of a variety of permeation enhancers may be employed, to increase uptake in the intestines upon dissolution of the enteric coating. In one aspect, permeation enhancers increase either paracellular or transcellular transport systems. Representative, non-limiting examples of such permeation enhancers include calcium chelators, bile salts (such as sodium cholate), and fatty acids. In some embodiments, peptides or polypeptides that act as substrates for intestinal proteases are further added.

Cyclic peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The cyclic peptides disclosed herein may be therapeutically applied by means of nasal administration. The peptides may be in an aqueous solution, such as a solution including saline, citrate or other common excipients or preservatives, as well as absorption or permeation enhancers, transcellular permeation enhancers, mucoadhesive polymers, and various carrier systems. The peptides may also be in a dry or powder formulation. The cyclic peptides disclosed herein, or of a formula disclosed herein, may be formulated with any of a variety of agents that increase effective nasal absorption of drugs, including peptide drugs. These agents may increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the cyclic peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, cyclic peptides disclosed herein, or of a formula disclosed herein, may be administered directly into the lung. Intrapulmonary administration may be performed by means of a metered dose inhaler, a device allowing self-administration of a metered bolus of a peptide disclosed herein, or of a formula disclosed herein, when actuated by a patient during inspiration. In one aspect of this embodiment, the cyclic peptide may be in a dried and particulate form, for example particles between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying, and a quick freeze aerosol followed by lyophilization. With microparticles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The cyclic peptides disclosed herein, or of a formula disclosed herein, may be therapeutically administered by means of an injection of a sustained release formulation. In one embodiment, a cyclic peptide disclosed herein, or of a formula disclosed herein, is formulated for a deep intramuscular injection, such as in the gluteal or deltoid muscle, of a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a cyclic peptide disclosed herein, or of a formula disclosed herein, is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are in one aspect preferably also adhesive polymers, may be employed in a sustained release injectable formulation. Alternatively other sustained release formulations may be employed, including formulations permitting subcutaneous injection, which other formulations may include one or more of nano/microspheres (such as compositions including PLGA polymers), liposomes, emulsions (such as water-in-oil emulsions), gels, insoluble salts or suspensions in oil. The formulation may be such that an injection is required on a daily, weekly, monthly or other periodic basis, depending on the concentration and amount of cyclic peptide, the sustained release rate of the materials employed, and other factors known to those of skill in the art.

6.3 Routes of Administration

If a composition including one or more peptides disclosed herein, or of a formula disclosed herein, is administered by injection, the injection may be intravenous, subcutaneous, intramuscular, intraperitoneal or other means known in the art. The peptides disclosed herein, or of a formula disclosed herein, may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

6.4 Therapeutically Effective Amount

In general, the actual quantity of cyclic peptides disclosed herein, or of a formula disclosed herein, administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. The cyclic peptides disclosed herein, or of a formula disclosed herein, are generally highly active. For example, the cyclic peptide can be administered at about 0.001, 0.01, 0.1, 0.5, or 1 μg/kg body weight, depending on the specific peptide selected, the desired therapeutic response, the route of administration, the formulation and other factors known to those of skill in the art.

7.0 Tests and Assays Employed in Evaluation of Peptides

The melanocortin receptor-specific peptides disclosed herein, or of a formula disclosed herein, may be tested by a variety of assay systems and animal models to determine binding, functional status and efficacy.

7.1 Assay for Agonist Activity Performed at CEREP

Evaluation of the agonist activity of compounds at the melanocortin receptors was determined by measuring their effects on cAMP production using the HTRF detection method at CEREP (Eurofins CEREP SA, Celle-Levescault, France). The cells were suspended in HBSS buffer (Invitrogen) complemented with 20 mM HEPES (pH 7.4) and 500 μM IBMX, then distributed in microplates and incubated in the presence of HBSS (basal control), the test compound or the reference agonist. Incubation time, temperature, cell number, reference agonist and cell line information are included in the Table 1 below. For stimulated control measurement, separate assay wells contain reference compound. Following incubation, the cells are lysed and the fluorescence acceptor ($D_2$-labeled cAMP) and fluorescence donor (anti-cAMP antibody labeled with europium cryptate) were added. After 60 minutes at room temperature, the fluorescence transfer was measured at excitation wavelength 337 nm and emission wavelengths 620 and 665 nm using a microplate reader (Envision, Perkin Elmer). The cAMP concentration was determined by dividing the signal measured at 665 nm by that measured at 620 nm (ratio).

The results are expressed as a percent of the control response to 1 μM of the reference. The standard reference agonist is tested in each experiment at several concentrations to generate a concentration-response curve from which its $EC_{50}$ value is calculated.

| CEREP assay No. | Protein Name | Species | Cell type | Control | Incubation time, min | Incubation temp | Cell number per well |
|---|---|---|---|---|---|---|---|
| 2147 | MC1 | Mouse | B16-F1 | NDP-alpha-MSH | 10 | room temp | 10,000 |
| 2240 | MC2 | Human | Cloudman S91 (M3) | ACTH(1-39) | 10 | room temp | 10,000 |
| 959 | MC3 | Human | CHO-K1 | NDP-alpha-MSH | 30 | 37 C. | 10,000 |
| 699 | MC4 | Human | CHO-K1 | NDP-alpha-MSH | 30 | 37 C. | 5,000 |
| 1869 | MC5 | Human | CHO-K1 | Alpha-MSH | 30 | 37 C. | 10,000 |

7.2 Assay for Antagonist Activity Performed at CEREP

This assay was utilized to evaluate the antagonist activity of compounds at melanocortin receptors determined by measuring effects on cAMP production using the HTRF detection method.

The desired cells with melanocortin receptors are suspended in HBSS buffer (Invitrogen) complemented with 20 mM HEPES (pH 7.4) and 500 μM IBMX, then distributed in microplates in the presence of HBSS (basal control), the test compound or the reference antagonist. Thereafter, one concentration of agonist is added to stimulate cAMP production. For basal control measurements, separate assay wells do not contain reference agonist. Incubation time, temperature, cell number, reference agonist and cell line information are included in Table 2 below.

Following incubation, the cells are lysed and the fluorescence acceptor ($D_2$-labeled cAMP) and fluorescence donor (anti-cAMP antibody labeled with europium cryptate) are added. After 60 minutes at room temperature, the fluorescence transfer is measured at excitation wavelength 337 nm and emission wavelengths 620 and 665 nm using a microplate reader (Envision, Perkin Elmer). The cAMP concentration is determined by dividing the signal measured at 665 nm by that measured at 620 nm (ratio). The results are expressed as a percent inhibition of the control response to reference agonist. The standard reference antagonist is tested in each experiment at several concentrations to generate a concentration-response curve from which its $IC_{50}$ value is calculated.

| CEREP assay No. | Protein Name | Species | Cell type | Stimulation Agonist | Incubation Time with Antagonist, min | Incubation Time with Agonist, min | Incubation Temp | Cell number per well |
|---|---|---|---|---|---|---|---|---|
| 2148 | MC1 | Mouse | B16-F1 | NDP-alpha - MSH (10 nM) | 5 | 10 | room temp | 10,000 |
| 2241 | MC2 | Human | Cloudman S91 (M3) | ACTH (1-39) (100 nM) | 5 | 10 | room temp | 10,000 |
| 1755 | MC3 | Human | CHO-K1 | NDP-alpha - MSH (30 nM) | 5 | 30 | 37 C. | 10,000 |
| 700 | MC4 | Human | CHO-K1 | NDP-alpha - MSH (1 nM) | 5 | 30 | 37 C. | 5,000 |
| 1870 | MC5 | Human | CHO-K1 | alpha -MSH (1000 nM) | 5 | 30 | 37 C. | 10,000 |

7.3 Alternative Assay for Agonist Activity

Accumulation of intracellular cAMP was examined as a measure of the ability of the peptides to elicit a functional response in either HEK-293 cells that express recombinant MC3r or MC4r or B16-F10 (mouse) and HBL (human) cell lines that express native MC1 r. Confluent cells were detached from culture plates by incubation in enzyme-free cell dissociation buffer. Dispersed cells were suspended in Hank's Balanced Salt Solution containing 10 mM HEPES (pH 7.5), 1 mM $MgCl_2$, 1 mM glutamine, 0.5% albumin and 0.3 mM 3-isobutyl-1-methyl-xanthine (IBMX), a phosphodiesterase inhibitor. The cells were dispensed into 96-well plates at a density of $0.5\times10^5$ cells per well and pre-incubated for 10 minutes. Cells were exposed for 15 minutes at 37° C. to peptides dissolved in DMSO (final DMSO concentration of 1%) at a concentration range of 0.05-5000 nM in a total assay volume of 200 μL. NDP-α-MSH was used as the reference agonist. cAMP levels were determined by an HTRF® cAMP cell-based assay system from Cisbio Bioassays utilizing cryptate-labeled anti-cAMP and $D_2$-labeled cAMP, with plates read on a Perkin-Elmer Victor plate reader at 665 and 620 nM. Data analysis was performed by nonlinear regression analysis with Graph-Pad Prism® software. The maximum efficacies of the test peptides were compared to that achieved by the reference melanocortin agonist NDP-α-MSH.

7.4 High and Low Density hMC4r Functional Assay

A HEK293 cell line transfected with human MC4r (from Palatin Technologies, US, with license from the University of Michigan) was used. The human MC4r was introduced to HEK293 by using the T-REx™ System, Invitrogen. The T-REx™ System employs a tetracycline-regulated mammalian expression system that uses regulatory elements from the *E. coli* Tn10-encoded tetracycline (Tet) resistance operon. By use of the T-REx™ System, expression of the gene of interest, the human MC4r gene, is repressed in the absence of tetracycline or doxycycline and induced in the presence of tetracycline or doxycycline (see T-REx™ System Manual, published by Invitrogen).

HEK293-T-REx-MC4r cells were cultured in DMEM (Gibco 11965) supplemented with L-Glutamine (Gibco 25030), 10% fetal bovine serum (FBS), 200 μg/mL Zeocin (Invitrogen 46-0072) and 6 mg/mL Blasticidin (Invitrogen 46-1120) in 5% $CO_2$ and 95% humidity at 37° C. T-150 flasks of cells at 75% confluence were incubated with two concentrations of doxycycline (0.1 ng/mL to provide a low density hMC4r system and 10 ng/mL to provide a high density hMC4r system) in 5% $CO_2$ at 37° C. for 16-18 hours to induce MC4r expression. On the day of the assay, the cells were washed with PBS (Gibco 14190) and harvested using cell dissociation buffer (Gibco 13150-016), then centrifuged and resuspended in Hanks' Balanced Salt Solution (+Ca, +Mg) (Gibco 14025), 10 mM 4-(2-hydroxyethyl)-1-piperazineethanesulfonic acid (HEPES) (pH 7.4) (Sigma H0887), 1 mM L-Glutamine (Gibco 25030), 1 mg/mL bovine serum albumin (BSA) (Sigma A3311) and 0.3 mM 3-isobutyl-1-methyl-xanthine (IBMX).

The cells were then dispensed into 96-well plates (BD 353916) in 198 μL (about $5\times10^4$) cells/well and incubated for 10 minutes at 37° C. Cells were exposed for 15 minutes at 37° C. to peptides dissolved in DMSO (final DMSO concentration of 1%) at a concentration range from $10^{-5}$ to $10^{-13}$ M in total assay volumes of 200 μL, with NDP-α-MSH used as the reference agonist. The reaction was stopped by adding 15 μL of lysis buffer per well and the plates were shook for 30 minutes at room temperature.

cAMP levels were determined by an HTRF® cAMP cell-based assay system from Cisbio Bioassays utilizing cryptate-labeled anti-cAMP and d2-labeled cAMP, with plates read on a Perkin-Elmer Victor plate reader at 665 and 620 nM. Data analysis was performed by nonlinear regression analysis with Graph-Pad Prism® software. The maximum efficacies of the test peptides were compared to that achieved by the reference melanocortin agonist NDP-α-MSH.

Agonist stimulation of the MC4r activates adenylate cyclase, which is an enzyme that catalyses the formation 3',5'-cyclic adenosine monophosphate (cAMP) from adenosine triphosphate (ATP). Thus, agonist stimulation of the MC4r increases the levels of cAMP. cAMP-levels were measured with the cAMP dynamic 2 HTRF kit (CisBio Catalog No. 62AM4PEC; see manual published by CisBio). cAMP levels were normalised against plate controls (1% DMSO for 0%, 400 nM NDP-α-MSH for 100%) and a calibration curve ranging from 712 nM to 0.04 nM cAMP (as described in the CisBio HTRF kit). The plates were incubated on a shaker at room temperature for 1 hour and read on the Perkin-Elmer Victor plate reader at 665 and 620 nm. Fluorescence ratios were then calculated as described in the CisBio HTRF kit, with GraphPad Prism software used to plot the change in fluorescence percent values versus cAMP concentration using the variable slope dose response curve and, based on calculated cAMP concentrations, to determine $EC_{50}$ and $E_{max}$ values.

8.0 Peptide Structures Examples

In one aspect, there is provided a cyclic peptide which contains a core sequence derived from or a modification of the sequence His-Phe-Arg-Trp (SEQ ID NO: 82) within the cyclic portion, which peptide is cyclized through the side chain of the amino acid immediately adjacent, on the N terminus side, the His (or derivative, modification of or substitute for His) and the C terminus group of the peptide. The cyclic peptide is at least a cyclic pentapeptide, containing five amino acids within the cyclic portion, and optionally is a cyclic hexapeptide, heptapeptide or larger cyclic peptide, with one or more additional amino acid residues outside the cyclic portion on the N terminus end.

For MC4r antagonists, which may simultaneously comprise MC1 r, MC3r or MC54 agonists, or a combination thereof, the core sequence derived from His-Phe-Arg-Trp (SEQ ID NO: 82) in some aspects will include D-Phe is the Phe position rather than L-Phe, Nal 1 or Nal 2 substitutions in the Phe position, such as D-Nal 1 or D-Nal 2, or alternatively may include substituted Phe in the Phe position, such as substituted L-Phe or D-Phe. A variety of amino acids may be utilitized for the remaining amino acids in the core sequence. In general, the His position may be a substituted or unsubstituted Pro, or may be an amino acid with a side chain including at least one primary amine, secondary amine, alkyl, cycloalkyl, cycloheteroalkyl, aryl, heteroaryl, alcohol, ether, sulfide, sulfone, sufoxide, carbamoyl or carboxyl. The Arg position may be a substituted or unsubstituted Pro or may be an amino acid with a side chain including at least one primary amine, secondary amine, guanidine, urea, alkyl, cycloalkyl, cycloheteroalkyl, aryl, heteroaryl, or ether. The Trp position may be an amino acid with a side chain including at least one substituted or unsubstituted aryl or heteroaryl, or alternatively may be omitted.

The peptides encompassed within formulas I, II, III, IV and V contain one or more asymmetric elements such as stereogenic centers, stereogenic axes and the like, so that the peptides encompassed within such formulas can exist in different stereoisomeric forms. For both specific and generically described peptides, including the peptides encompassed within formulas I, II, III, IV and V, all forms of isomers at all chiral or other isomeric centers, including enantiomers and diastereomers, are intended to be covered herein. The peptides of the invention each include multiple chiral centers, and may be used as a racemic mixture or an enantiomerically enriched mixture, in addition to use of the peptides of the invention in enantiopure preparations. Typically, the peptides of the invention will be synthesized with the use of chirally pure reagents, such as specified L- or D-isomer amino acids, using reagents, conditions and methods such that enantiomeric purity is maintained, but it is possible and contemplated that racemic mixtures may be made. Such racemic mixtures may optionally be separated using well-known techniques and an individual enantiomer may be used alone. In cases and under specific conditions of temperature, solvents and pH wherein peptides may exist in tautomeric forms, each tautomeric form is contemplated as being included within this invention whether existing in equilibrium or predominantly in one form. Thus, a single enantiomer of a peptide of formulas I through V, which is an optically active form, can be obtained by asymmetric synthesis, synthesis from optically pure precursors, or by resolution of the racemates.

The peptides disclosed herein are a specific stereoisomeric form of the peptides of formulas I through V, but the invention should not be construed as being limited to the stereoisomeric forms encompassed by peptides disclosed herein.

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo into a peptide of formulas I through V. Prodrugs are any covalently bonded compounds, which release the active parent peptide drug of formulas I through V in vivo. Conventional procedures for the selection and preparation of suitable prodrug derivatives are described, for example, in "Design of Prodrugs", ed. H. Bundgaard, Elsevier, 1985. Typical examples of prodrugs have biologically labile protecting groups on a functional moiety, such as for example by esterification of hydroxyl, carboxyl or amino functions. Thus by way of example and not limitation, a prodrug includes peptides of formulas I through V wherein an ester prodrug form is employed, such as, for example, lower alkyl esters of an R group of formulas I through V, such as where R is —OH, which lower alkyl esters may include from 1-8 carbons in an alkyl radical or aralkyl esters which have 6-12 carbons in an aralkyl radical. Broadly speaking, prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce an active parent peptide drug of formula I in vivo.

The subject invention also includes peptides which are identical to those recited in formulas I though V, but for the fact that one or more atoms depicted in such formulas are replaced by an atom having an atomic mass or mass number different from the atomic mass or mass number usually found in nature. Examples of isotopes that can be incorporated into peptides of the invention include isotopes of hydrogen, carbon, nitrogen and oxygen, such as $^{2}H$, $^{3}H$, $^{13}C$, $^{14}C$, $^{15}N$, $^{18}O$ and $^{17}O$, respectively. Peptides disclosed herein, or of a formula disclosed herein, and pharmaceutically acceptable salts or solvates of said peptides which contain the aforementioned isotopes and/or other isotopes of other atoms are within the scope of this invention. Certain isotopically-labeled peptides, for example those into which radioactive isotopes such as $^{3}H$ and $^{14}C$ are incorporated, may have use in a variety of assays, such as in drug and/or substrate tissue distribution assays. Substitution with heavier isotopes, such as substitution of one or more hydrogen atoms with deuterium ($^{2}H$), can provide pharmacological advantages in some instances, including increased metabolic stability. Isotopically labeled peptides of formula I can generally be prepared by substituting an isotopically labeled reagent for a non-isotopically labeled reagent.

9.0 Examples

The invention is further exemplified by the following non-limiting examples:

9.1 Peptides Synthesized and Functional Data 9.1.1 Peptides of the following structures were synthesized by the general methods described above, and $EC_{50}$ values for peptides were determined as indicated. $EC_{50}$ values marked with an "*" were determined by CEREP. The "%" indicates $E_{max}$ percent (percent of the maximal response obtained with the positive control) in the case of $EC_{50}$ values. An $EC_{50}$ value of "NC" indicates that the $EC_{50}$ value was over 10,000 nM and hence was not calculable.

| No. | Structure | Amino Acid Sequence and Functional Data |
|---|---|---|
| 1 | 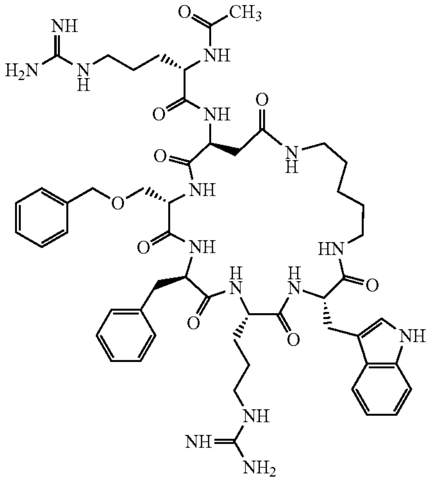 [SMILES: CC(=O)N[C@@H](CCCNC(=N)N)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2ccccc2)NC(=O)[C@H](COCc2ccccc2)NC1=O] | Ac-Arg-Asp-Ser(Bzl)-D-Phe-Arg-Trp (Arg NH—$(CH_2)_5$—NH Trp)<br>Receptor / Assay / Value (nM) / %<br>hMC1r / $EC_{50}$ / 125 / 70%<br>hMC4r / $EC_{50}$ / 1.0 / 42% |
| 2 | 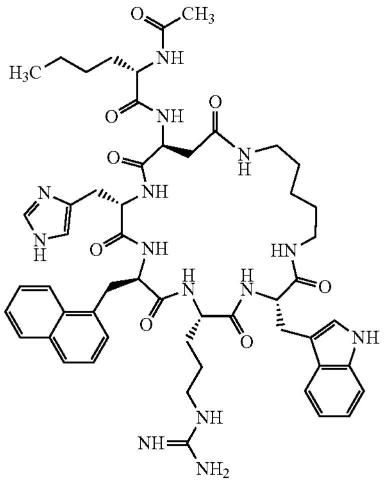 [SMILES: CCCC[C@H](NC(C)=O)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](Cc2c[nH]cn2)NC1=O] | Ac-Nle-Asp-His-D-Nal 1-Arg-Trp (Asp NH—$(CH_2)_5$—NH Trp)<br>Receptor / Assay / Value (nM) / %<br>hMC1r* / $EC_{50}$ / 0.08 / 81%<br>mMC1r* / $EC_{50}$ / 0.22 / 102%<br>hMC3r* / $EC_{50}$ / NC / 36%<br>hMC4r* / $EC_{50}$ / 0.18 / 46%<br>hMC5r* / $EC_{50}$ / 140 / 60% |

-continued

| No. | Structure | Amino Acid Sequence and Functional Data |
|---|---|---|

3

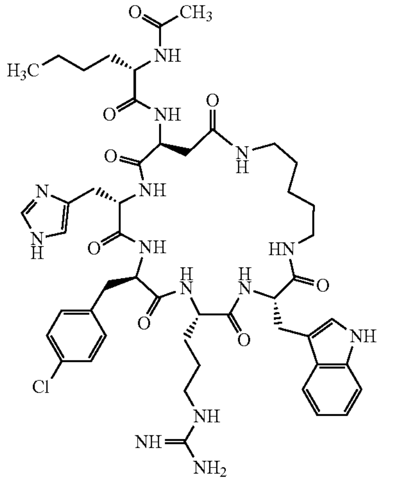 [SMILES: CCCC[C@H](NC(C)=O)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2ccc(Cl)cc2)NC(=O)[C@H](Cc2c[nH]cn2)NC1=O]

Ac-Nle-Asp-His-D-Phe(4-Cl)-Arg-Trp
NH———$(CH_2)_5$———NH

| Receptor | Assay | Value (nM) | % |
|---|---|---|---|
| mMC1r | $EC_{50}$ | 0.03 | 74% |
| mMC1r* | $EC_{50}$ | 0.032 | 78% |
| hMC3r | $EC_{50}$ | 0.933 | 33% |
| hMC4r | $EC_{50}$ | 2 | 60% |
| hMC5r* | $EC_{50}$ | NC | 24% |

4

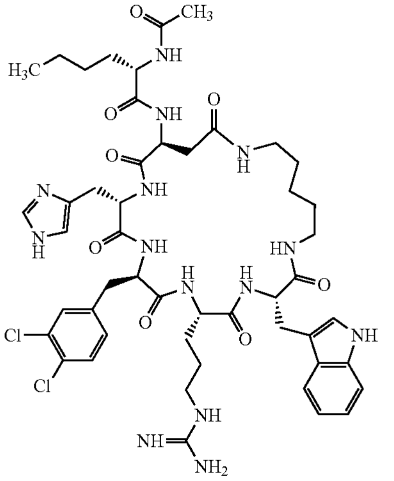 [SMILES: CCCC[C@H](NC(C)=O)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2ccc(Cl)c(Cl)c2)NC(=O)[C@H](Cc2c[nH]cn2)NC1=O]

Ac-Nle-Asp-His-D-Phe(3,4-Cl)-Arg-Trp
NH———$(CH_2)_5$———NH

| Receptor | Assay | Value (nM) | % |
|---|---|---|---|
| mMC1r | $EC_{50}$ | 2 | 54% |
| mMC1r* | $EC_{50}$ | 1 | 50% |
| hMC3r | $EC_{50}$ | NC | 5% |
| hMC4r | $EC_{50}$ | 120 | 15% |

5

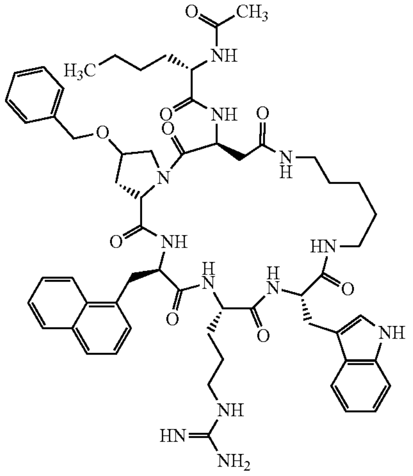

Ac-Nle-Asp-Hyp(Bzl)-D-Nal 1-Arg-Trp
NH———$(CH_2)_5$———NH

| Receptor | Assay | Value (nM) | % |
|---|---|---|---|
| mMC1r | $EC_{50}$ | 5 | 35% |
| mMC1r* | $EC_{50}$ | 3 | 37% |
| hMC3r | $EC_{50}$ | NC | 7% |
| hMC3r* | $EC_{50}$ | NC | 7% |
| hMC4r | $EC_{50}$ | 5002 | 19% |
| hMC4r* | $EC_{50}$ | NC | 15% |
| hMC5r* | $EC_{50}$ | 1 | 111% |
| hMC5r | $EC_{50}$ | 0.7 | 92% |

-continued

| No. | Structure | Amino Acid Sequence and Functional Data |
|---|---|---|

6

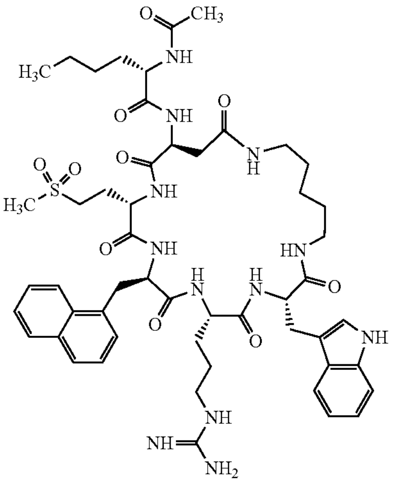 [SMILES: CCCC[C@H](NC(C)=O)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](CCS(C)(=O)=O)NC1=O]

Ac-Nle-Asp-Met($O_2$)-D-Nal 1-Arg-Trp

NH——$(CH_2)_5$——NH

| Receptor | Assay | Value (nM) | % |
|---|---|---|---|
| mMC1r | $EC_{50}$ | 8 | 74% |
| mMC1r* | $EC_{50}$ | 28 | 81% |
| hMC3r* | $EC_{50}$ | 5 | 10% |
| hMC3r* | $EC_{50}$ | NC | 10% |
| hMC4r | $EC_{50}$ | 5 | 28% |
| hMC4r* | $EC_{50}$ | 0.55 | 50% |
| hMC5r* | $EC_{50}$ | 14 | 75% |

7

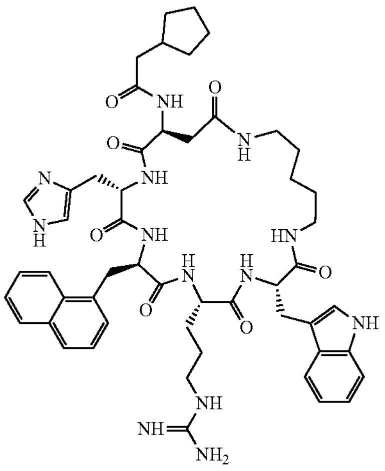 [SMILES: N=C(N)NCCC[C@@H]1NC(=O)[C@@H](Cc2cccc3ccccc23)NC(=O)[C@H](Cc2c[nH]cn2)NC(=O)[C@@H](NC(=O)CC2CCCC2)CC(=O)NCCCCCNC(=O)[C@H](Cc2c[nH]c3ccccc23)NC1=O]

cyclopentyl acetyl-Asp-His-D-Nal 1-Arg-Trp

NH——$(CH_2)_5$——NH

| Receptor | Assay | Value (nM) | % |
|---|---|---|---|
| mMC1r* | $EC_{50}$ | 0.14 | 76% |
| hMC3r | $EC_{50}$ | 0.5 | 55% |
| hMC5r* | $EC_{50}$ | 46 | 58% |

8

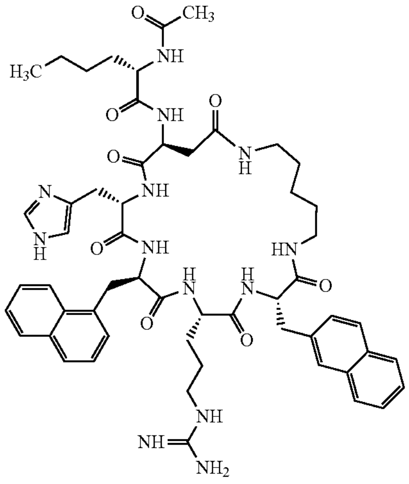 [SMILES: CCCC[C@H](NC(C)=O)C(=O)N[C@H]1CC(=O)NCCCCCNC(=O)[C@H](Cc2ccc3ccccc3c2)NC(=O)[C@H](CCCNC(=N)N)NC(=O)[C@@H](Cc2cccc3ccccc23)NC(=O)[C@H](Cc2c[nH]cn2)NC1=O]

Ac-Nle-Asp-His-D-Nal 1-Arg-Nal 2

NH——$(CH_2)_5$——NH

| Receptor | Assay | Value (nM) | % |
|---|---|---|---|
| mMC1r* | $EC_{50}$ | 3 | 59% |
| hMC3r | $EC_{50}$ | 0.2 | 21% |
| hMC4r | $EC_{50}$ | 0.95 | 35% |
| hMC5r* | $EC_{50}$ | 6 | 47% |

-continued

| No. | Structure | Amino Acid Sequence and Functional Data |
|---|---|---|

9

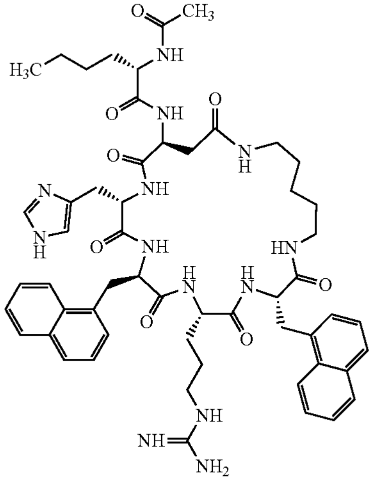 [SMILES: CCCC[C@H](NC(C)=O)C(=O)N[C@H]1CC(=O)NCCCCCNC(=O)[C@H](Cc2cccc3ccccc23)NC(=O)[C@H](CCCNC(=N)N)NC(=O)[C@@H](Cc2cccc3ccccc23)NC(=O)[C@H](Cc2c[nH]cn2)NC1=O]

Ac-Nle-Asp-His-D-Nal 1-Arg-Nal 1

NH——$(CH_2)_5$——NH

| Receptor | Assay | Value (nM) | % |
|---|---|---|---|
| mMC1r* | $EC_{50}$ | 160 | 65% |
| hMC3r | $EC_{50}$ | 20 | 39% |
| hMC4r | $EC_{50}$ | 3 | 43% |
| hMC5r* | $EC_{50}$ | 3400 | 77% |

10

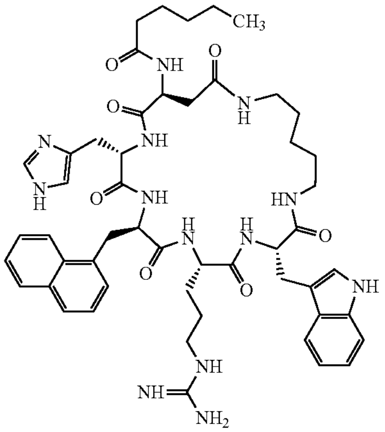 [SMILES: CCCCCC(=O)N[C@H]1CC(=O)NCCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](Cc2c[nH]cn2)NC1=O]

Hexanoyl-Asp-His-D-Nal 1-Arg-Trp

NH——$(CH_2)_5$——NH

| Receptor | Assay | Value (nM) | % |
|---|---|---|---|
| mMC1r* | $EC_{50}$ | 0.66 | 76% |
| hMC3r | $EC_{50}$ | 132 | 60% |
| hMC4r | $EC_{50}$ | 0.6 | 54% |
| hMC5r* | $EC_{50}$ | 360 | 61% |

11

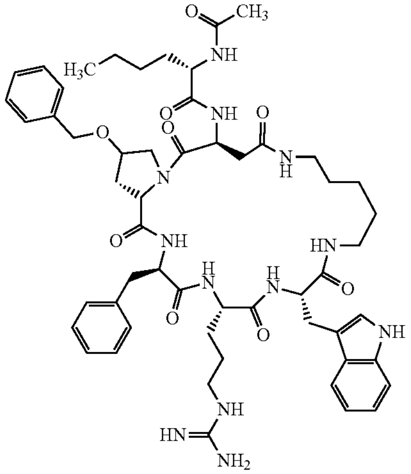

Ac-Nle-Asp-Hyp(Bzl)-D-Phe-Arg-Trp

NH——$(CH_2)_5$——NH

| Receptor | Assay | Value (nM) | % |
|---|---|---|---|
| mMC1r | $EC_{50}$ | 2 | 96% |
| mMC1r* | $EC_{50}$ | 7 | 54% |
| hMC3r | $EC_{50}$ | 3 | 40% |
| hMC4r | $EC_{50}$ | 2 | 78% |
| hMC5r* | $EC_{50}$ | 4 | 49% |

-continued

| No. | Structure | Amino Acid Sequence and Functional Data |
|---|---|---|
| 12 | 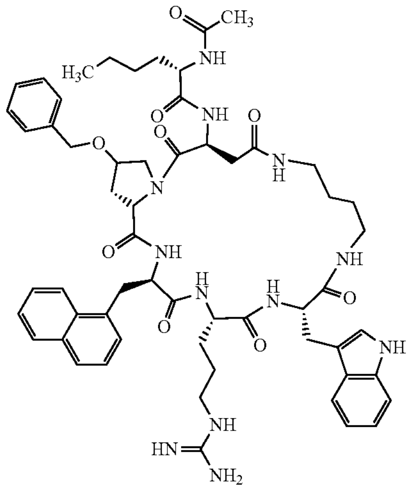 | Ac-Nle-Asp-Hyp(Bzl)-D-Nal 1-Arg-Trp, with NH—$(CH_2)_4$—NH bridge |
| 13 | 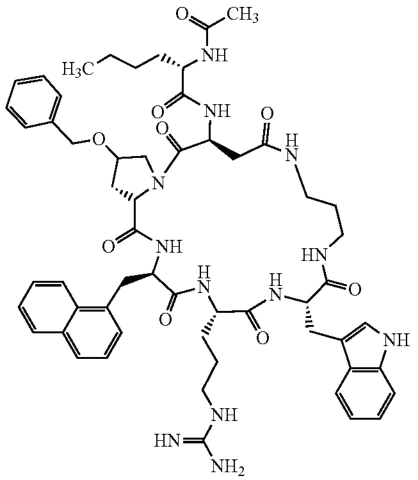 | Ac-Nle-Asp-Hyp(Bzl)-D-Nal 1-Arg-Trp, with NH—$(CH_2)_3$—NH bridge |
| 14 | 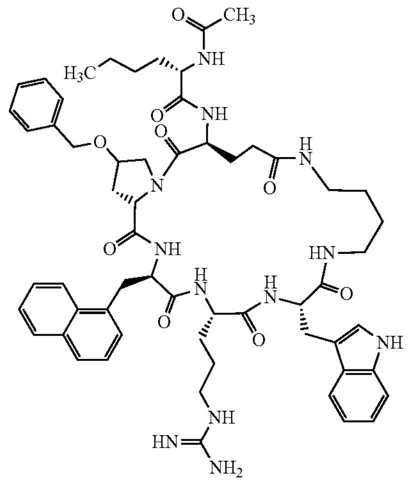 | Ac-Nle-Glu-Hyp(Bzl)-D-Nal 1-Arg-Trp, with NH—$(CH_2)_4$—NH bridge |

No. 12:

| Receptor | Assay | Value (nM) | % |
|---|---|---|---|
| mMC1r | $EC_{50}$ | 0.38 | 30% |
| hMC3r | $EC_{50}$ | NC | 10% |
| hMC4r | $EC_{50}$ | NC | 16% |

No. 13:

| Receptor | Assay | Value (nM) | % |
|---|---|---|---|
| mMC1r | $EC_{50}$ | 0.08 | 22% |
| hMC3r | $EC_{50}$ | NC | 2% |
| hMC4r | $EC_{50}$ | NC | 16% |

No. 14:

| Receptor | Assay | Value (nM) | % |
|---|---|---|---|
| mMC1r | $EC_{50}$ | 0.2 | 33% |
| hMC3r | $EC_{50}$ | NC | 13% |
| hMC4r | $EC_{50}$ | 1 | 30% |

-continued

<table>
<tr><th>No.</th><th>Structure</th><th>Amino Acid Sequence and Functional Data</th></tr>
<tr><td>15</td><td>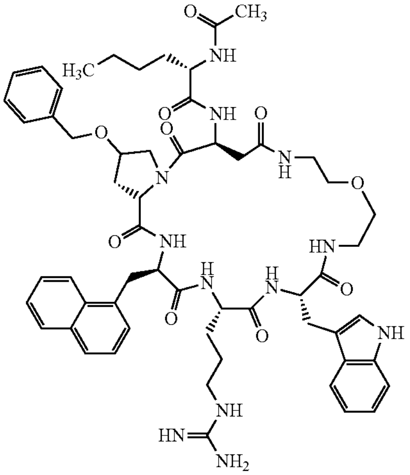</td><td>Ac-Nle-Asp-Hyp(Bzl)-D-Nal 1-Arg-Trp<br>NH—$(CH_2)_2$—O—$(CH_2)_2$—NH<br><table><tr><th>Receptor</th><th>Assay</th><th>Value (nM)</th><th>%</th></tr><tr><td>mMC1r</td><td>$EC_{50}$</td><td>3</td><td>39%</td></tr><tr><td>hMC3r</td><td>$EC_{50}$</td><td>NC</td><td>9%</td></tr><tr><td>hMC4r</td><td>$EC_{50}$</td><td>NC</td><td>17%</td></tr></table></td></tr>
<tr><td>16</td><td>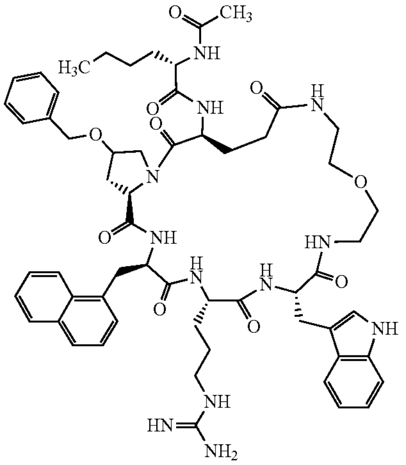</td><td>Ac-Nle-Glu-Hyp(Bzl)-D-Nal 1-Arg-Trp<br>NH—$(CH_2)_2$—O—$(CH_2)_2$—NH<br><table><tr><th>Receptor</th><th>Assay</th><th>Value (nM)</th><th>%</th></tr><tr><td>mMC1r</td><td>$EC_{50}$</td><td>0.18</td><td>43%</td></tr><tr><td>hMC3r</td><td>$EC_{50}$</td><td>13</td><td>19%</td></tr><tr><td>hMC4r</td><td>$EC_{50}$</td><td>0.85</td><td>25%</td></tr></table></td></tr>
<tr><td>17</td><td>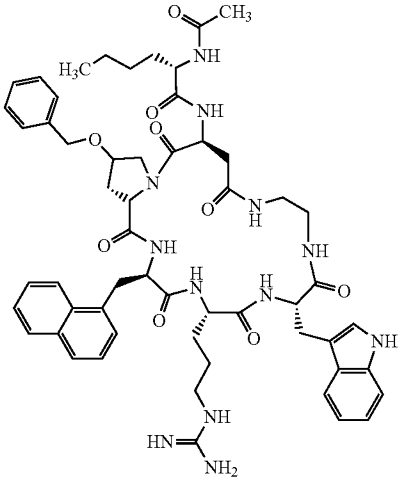</td><td>Ac-Nle-Asp-Hyp(Bzl)-D-Nal 1-Arg-Trp<br>NH——$(CH_2)_2$——NH<br><table><tr><th>Receptor</th><th>Assay</th><th>Value (nM)</th><th>%</th></tr><tr><td>mMC1r</td><td>$EC_{50}$</td><td>115</td><td>27%</td></tr><tr><td>hMC3r</td><td>$EC_{50}$</td><td>NC</td><td>8%</td></tr><tr><td>hMC4r</td><td>$EC_{50}$</td><td>3334</td><td>25%</td></tr></table></td></tr>
</table>

-continued

| No. | Structure | Amino Acid Sequence and Functional Data |
|---|---|---|
| 18 | 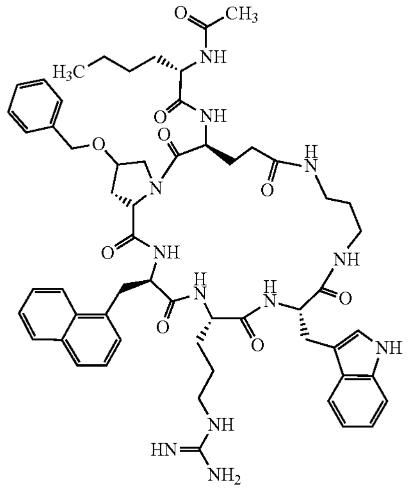 | Ac-Nle-Glu-Hyp(Bzl)-D-Nal 1-Arg-Trp<br>NH—$(CH_2)_3$—NH |

| Receptor | Assay | Value (nM) | % |
|---|---|---|---|
| mMC1r | $EC_{50}$ | 2 | 53% |
| mMC1r* | $EC_{50}$ | 490 | 61% |
| hMC3r | $EC_{50}$ | NC | 4% |
| hMC3r* | $EC_{50}$ | NC | 5% |
| hMC4r | $EC_{50}$ | NC | 12% |
| hMC4r* | $EC_{50}$ | 0.35 | 39% |
| hMC5r | $EC_{50}$ | 0.01 | 92% |
| hMC5r* | $EC_{50}$ | 0.4 | 101% |

| No. | Structure | Amino Acid Sequence and Functional Data |
|---|---|---|
| 19 | 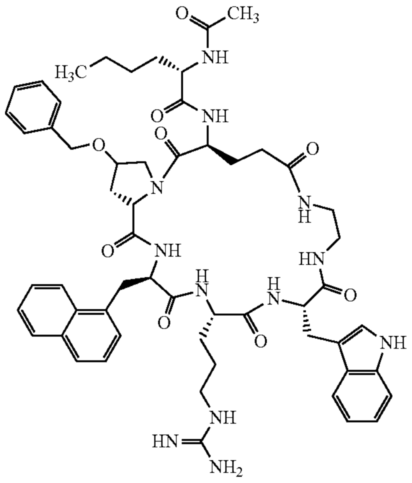 | Ac-Nle-Glu-Hyp(Bzl)-D-Nal 1-Arg-Trp<br>NH—$(CH_2)_2$—NH |

| Receptor | Assay | Value (nM) | % |
|---|---|---|---|
| mMC1r | $EC_{50}$ | 3 | 55% |
| hMC3r | $EC_{50}$ | NC | -2% |
| hMC4r | $EC_{50}$ | 0.667 | 25% |
| hMC5r | $EC_{50}$ | 0.005 | 93% |
| hMC5r* | $EC_{50}$ | 0.098 | 93% |

| No. | Structure | Amino Acid Sequence and Functional Data |
|---|---|---|
| 20 | 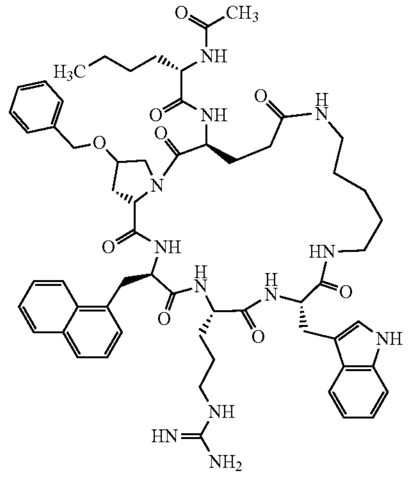 | Ac-Nle-Glu-Hyp(Bzl)-D-Nal 1-Arg-Trp<br>NH—$(CH_2)_5$—NH |

| Receptor | Assay | Value (nM) | % |
|---|---|---|---|
| hMC1r | $EC_{50}$ | 0.3 | 56% |
| mMC1r | $EC_{50}$ | 0.35 | 54% |
| hMC3r | $EC_{50}$ | NC | 14% |
| hMC4r | $EC_{50}$ | 0.633 | 29% |
| hMC5r | $EC_{50}$ | 0.01 | 60% |
| hMC5r* | $EC_{50}$ | 0.1 | 93% |

-continued

<table>
<tr><th>No.</th><th>Structure</th><th>Amino Acid Sequence and Functional Data</th></tr>
<tr><td>21</td><td>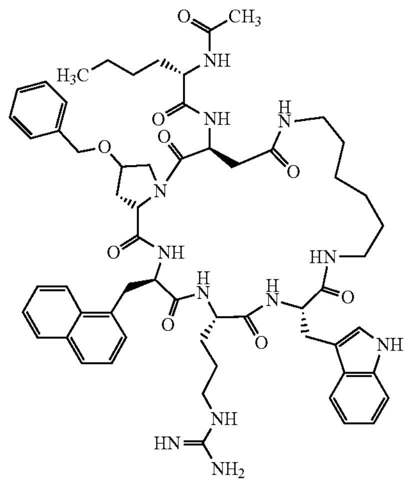</td><td>Ac-Nle-Asp-Hyp(Bzl)-D-Nal 1-Arg-Trp<br>NH—$(CH_2)_6$—NH
<table>
<tr><th>Receptor</th><th>Assay</th><th>Value (nM)</th><th>%</th></tr>
<tr><td>mMC1r</td><td>$EC_{50}$</td><td>11</td><td>48%</td></tr>
<tr><td>hMC3r</td><td>$EC_{50}$</td><td>5</td><td>28%</td></tr>
<tr><td>hMC4r</td><td>$EC_{50}$</td><td>10</td><td>35%</td></tr>
</table></td></tr>
<tr><td>22</td><td>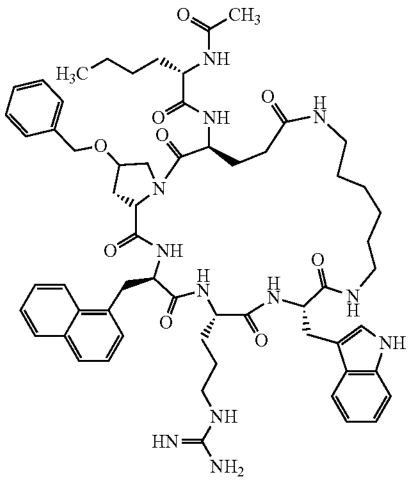</td><td>Ac-Nle-Glu-Hyp(Bzl)-D-Nal 1-Arg-Trp<br>NH—$(CH_2)_6$—NH
<table>
<tr><th>Receptor</th><th>Assay</th><th>Value (nM)</th><th>%</th></tr>
<tr><td>mMC1r</td><td>$EC_{50}$</td><td>3</td><td>69%</td></tr>
<tr><td>hMC3r</td><td>$EC_{50}$</td><td>2</td><td>15%</td></tr>
<tr><td>hMC4r</td><td>$EC_{50}$</td><td>12</td><td>29%</td></tr>
<tr><td>hMC5r*</td><td>$EC_{50}$</td><td>0.81</td><td>118%</td></tr>
</table></td></tr>
<tr><td>23</td><td>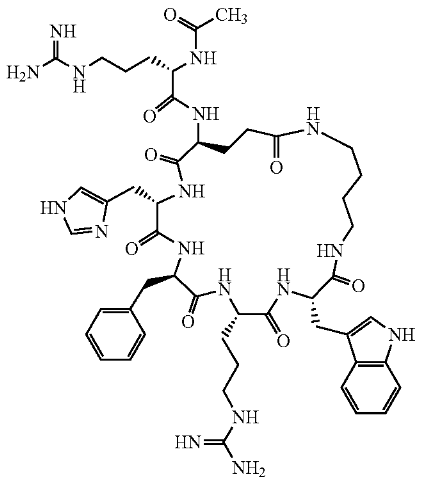 [SMILES: CC(=O)N[C@@H](CCCNC(=N)N)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O]</td><td>Ac-Arg-Glu-His-D-Phe-Arg-Trp<br>NH—$(CH_2)_4$—NH
<table>
<tr><th>Receptor</th><th>Assay</th><th>Value (nM)</th><th>%</th></tr>
<tr><td>mMC1r</td><td>$EC_{50}$</td><td>0.52</td><td>94%</td></tr>
<tr><td>mMC1r*</td><td>$EC_{50}$</td><td>0.16</td><td>86%</td></tr>
<tr><td>hMC3r</td><td>$EC_{50}$</td><td>0.4</td><td>95%</td></tr>
<tr><td>hMC3r*</td><td>$EC_{50}$</td><td>0.17</td><td>123%</td></tr>
<tr><td>hMC4r</td><td>$EC_{50}$</td><td>0.07</td><td>106%</td></tr>
<tr><td>hMC4r*</td><td>$EC_{50}$</td><td>0.037</td><td>108%</td></tr>
<tr><td>hMC5r*</td><td>$EC_{50}$</td><td>130</td><td>29%</td></tr>
</table></td></tr>
</table>

-continued

| No. | Structure | Amino Acid Sequence and Functional Data |
|---|---|---|

24

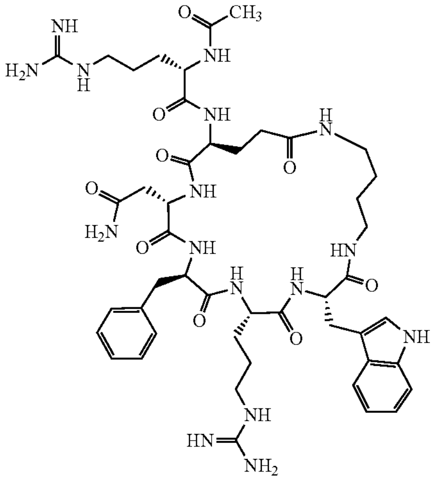 [SMILES: CC(=O)N[C@@H](CCCNC(=N)N)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O]

Ac-Arg-Glu-Asn-D-Phe-Arg-Trp

NH—$(CH_2)_4$—NH

| Receptor | Assay | Value (nM) | % |
|---|---|---|---|
| hMC1r | $EC_{50}$ | 39 | 100% |
| mMC1r | $EC_{50}$ | 127 | 87% |
| mMC1r* | $EC_{50}$ | 78 | 84% |
| hMC3r | $EC_{50}$ | 2 | 73% |
| hMC3r* | $EC_{50}$ | 7 | 98% |
| hMC4r | $EC_{50}$ | 0.2 | 123% |
| hMC4r* | $EC_{50}$ | 0.19 | 88% |
| hMC5r | $EC_{50}$ | 45 | 39% |
| hMC5r* | $EC_{50}$ | 680 | 70% |

25

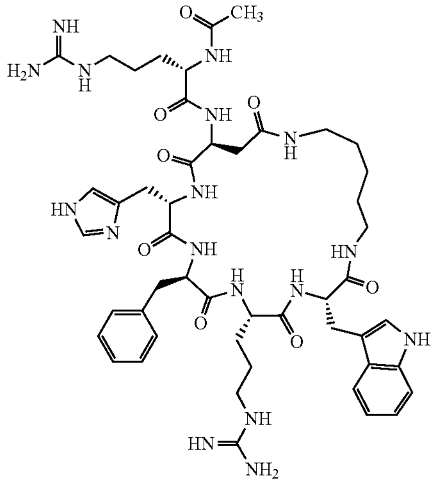 [SMILES: CC(=O)N[C@@H](CCCNC(=N)N)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O]

Ac-Arg-Asp-His-D-Phe-Arg-Trp

NH—$(CH_2)_5$—NH

| Receptor | Assay | Value (nM) | % |
|---|---|---|---|
| mMC1r | $EC_{50}$ | 4 | 86% |
| hMC3r | $EC_{50}$ | 3 | 95% |
| hMC4r | $EC_{50}$ | 0.22 | 98% |
| hMC5r* | $EC_{50}$ | NC | 25% |

26

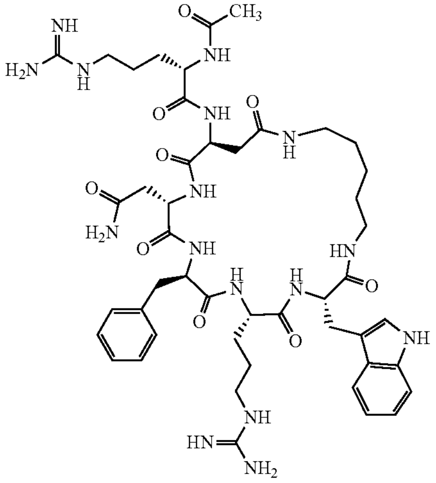 [SMILES: CC(=O)N[C@@H](CCCNC(=N)N)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O]

Ac-Arg-Asp-Asn-D-Phe-Arg-Trp

NH—$(CH_2)_5$—NH

| Receptor | Assay | Value (nM) | % |
|---|---|---|---|
| hMC1r | $EC_{50}$ | 179 | 76% |
| mMC1r | $EC_{50}$ | 489 | 58% |
| mMC1r* | $EC_{50}$ | 750 | 90% |
| hMC3r | $EC_{50}$ | 27 | 62% |
| hMC3r* | $EC_{50}$ | 79 | 50% |
| hMC4r | $EC_{50}$ | 0.885 | 91% |
| hMC4r* | $EC_{50}$ | 2 | 89% |
| hMC5r* | $EC_{50}$ | NC | 30% |

-continued

| No. | Structure | Amino Acid Sequence and Functional Data |
|---|---|---|
| 27 | 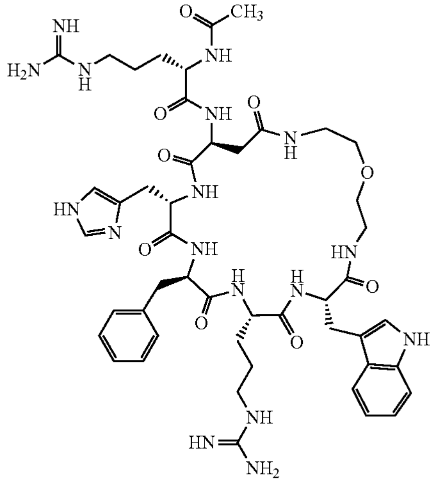 [SMILES: CC(=O)N[C@@H](CCCNC(=N)N)C(=O)N[C@H]1CC(=O)NCCOCCNC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O] | Ac-Arg-Asp-His-D-Phe-Arg-Trp (linked: NH-$(CH_2)_2$-O-$(CH_2)_2$-NH) |
| 28 | 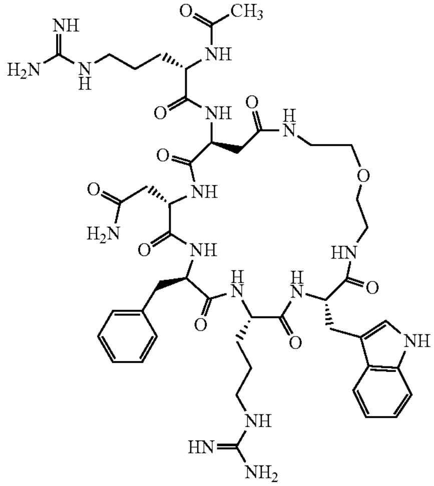 [SMILES: CC(=O)N[C@@H](CCCNC(=N)N)C(=O)N[C@H]1CC(=O)NCCOCCNC(=O)[C@H](Cc2c[nH]c3ccccc23)NC(=O)[C@H](CCCNC(=N)N)NC(=O)[C@@H](Cc2ccccc2)NC(=O)[C@H](CC(N)=O)NC1=O] | Ac-Arg-Asp-Asn-D-Phe-Arg-Trp (linked: NH-$(CH_2)_2$-O-$(CH_2)_2$-NH) |
| 29 | 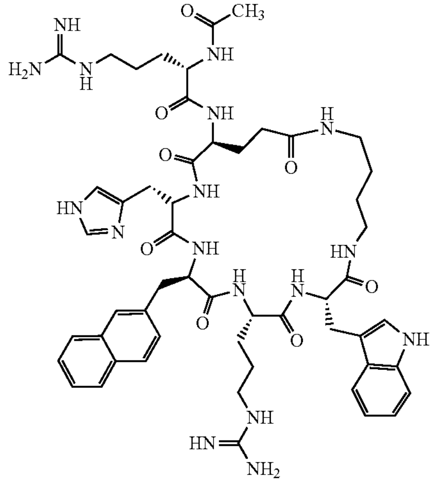 | Ac-Arg-Glu-His-D-Nal 2-Arg-Trp (linked: NH——$(CH_2)_4$——NH) |

Compound 27:

| Receptor | Assay | Value (nM) | % |
|---|---|---|---|
| mMC1r | $EC_{50}$ | 4 | 80% |
| hMC3r | $EC_{50}$ | 2 | 103% |
| mMC4r | $EC_{50}$ | 0.28 | 98% |
| hMC5r* | $EC_{50}$ | NC | 21% |

Compound 28:

| Receptor | Assay | Value (nM) | % |
|---|---|---|---|
| mMC1r | $EC_{50}$ | 135 | 66% |
| hMC3r | $EC_{50}$ | 20 | 56% |
| hMC4r | $EC_{50}$ | 0.875 | 102% |
| hMC5r* | $EC_{50}$ | NC | 30% |

Compound 29:

| Receptor | Assay | Value (nM) | % |
|---|---|---|---|
| mMC1r | $EC_{50}$ | 8 | 56% |
| hMC3r | $EC_{50}$ | 4 | 16% |
| hMC4r | $EC_{50}$ | NC | 13% |
| hMC5r* | $EC_{50}$ | 5 | 72% |

-continued

| No. | Structure | Amino Acid Sequence and Functional Data |
|---|---|---|
| 30 | 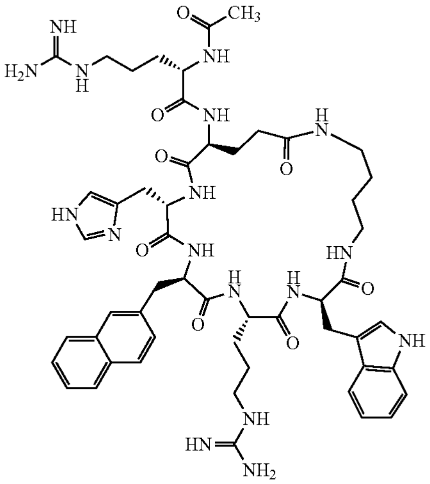 [SMILES: CC(=O)N[C@@H](CCCNC(=N)N)C(=O)N[C@H]1CCC(=O)NCCCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Arg-Glu-His-D-Nal 2-Arg-D-Trp<br>NH—$(CH_2)_4$—NH |

| Receptor | Assay | Value (nM) | % |
|---|---|---|---|
| mMC1r | $EC_{50}$ | 25 | 43% |
| hMC3r | $EC_{50}$ | NC | 2% |
| hMC4r | $EC_{50}$ | NC | 5% |
| hMC5r* | $EC_{50}$ | NC | 17% |

| No. | Structure | Amino Acid Sequence and Functional Data |
|---|---|---|
| 31 | 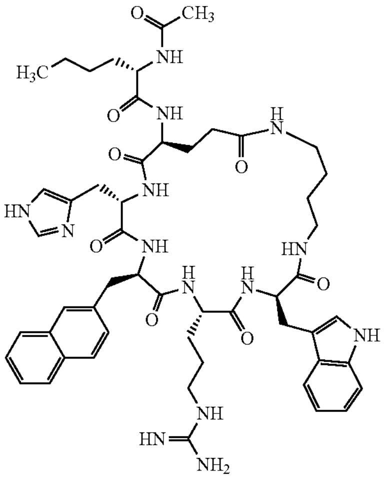 [SMILES: CCCC[C@H](NC(C)=O)C(=O)N[C@H]1CCC(=O)NCCCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Nle-Glu-His-D-Nal 2-Arg-D-Trp<br>NH—$(CH_2)_4$—NH |

| Receptor | Assay | Value (nM) | % |
|---|---|---|---|
| mMC1r | $EC_{50}$ | 0.7 | 40% |
| hMC3r | $EC_{50}$ | NC | 2% |
| hMC4r | $EC_{50}$ | NC | 6% |
| hMC5r* | $EC_{50}$ | NC | 11% |

| No. | Structure | Amino Acid Sequence and Functional Data |
|---|---|---|
| 32 | 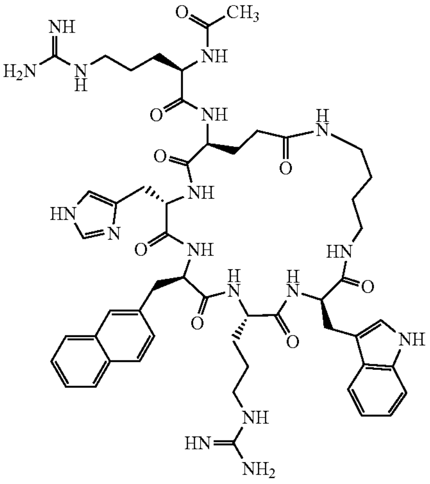 [SMILES: CC(=O)N[C@H](CCCNC(=N)N)C(=O)N[C@H]1CCC(=O)NCCCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-D-Arg-Glu-His-D-Nal 2-Arg-D-Trp<br>NH—$(CH_2)_4$—NH |

| Receptor | Assay | Value (nM) | % |
|---|---|---|---|
| mMC1r | $EC_{50}$ | 45 | 53% |
| hMC3r | $EC_{50}$ | NC | 0% |
| hMC4r | $EC_{50}$ | NC | 7% |
| hMC5r* | $EC_{50}$ | NC | 25% |

-continued

| No. | Structure | Amino Acid Sequence and Functional Data |
|---|---|---|
| 33 | 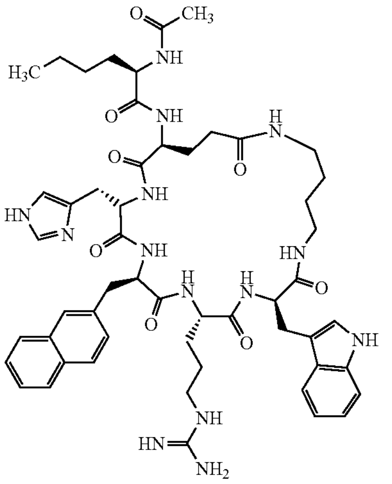 | Ac-D-Nle-Glu-His-D-Nal 2-Arg-D-Trp<br>NH——$(CH_2)_4$——NH |

| Receptor | Assay | Value (nM) | % |
|---|---|---|---|
| mMC1r | $EC_{50}$ | 0.4 | 48% |
| hMC3r | $EC_{50}$ | NC | 3% |
| hMC4r | $EC_{50}$ | NC | 5% |
| hMC5r* | $EC_{50}$ | NC | 12% |

| No. | Structure | Amino Acid Sequence and Functional Data |
|---|---|---|
| 34 | 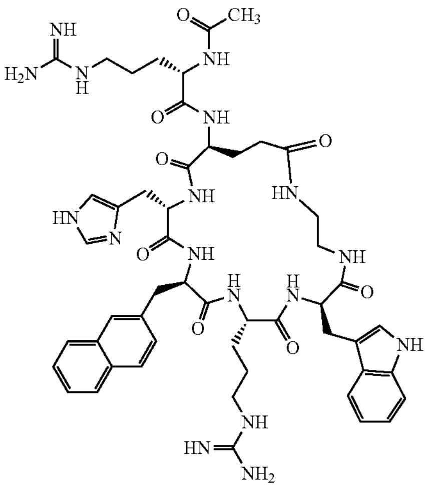 [SMILES: CC(=O)N[C@@H](CCCNC(=N)N)C(=O)N[C@H]1CCC(=O)NCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Arg-Glu-His-D-Nal 2-Arg-D-Trp<br>NH——$(CH_2)_2$——NH |

| Receptor | Assay | Value (nM) | % |
|---|---|---|---|
| mMC1r | $EC_{50}$ | 120 | 67% |
| hMC3r | $EC_{50}$ | NC | 0% |
| hMC4r | $EC_{50}$ | NC | 7% |

| No. | Structure | Amino Acid Sequence and Functional Data |
|---|---|---|
| 35 | 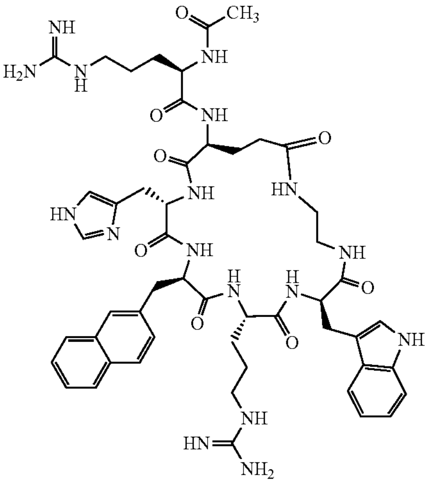 [SMILES: CC(=O)N[C@H](CCCNC(=N)N)C(=O)N[C@H]1CCC(=O)NCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-D-Arg-Glu-His-D-Nal 2-Arg-D-Trp<br>NH——$(CH_2)_2$——NH |

| Receptor | Assay | Value (nM) | % |
|---|---|---|---|
| mMC1r | $EC_{50}$ | 65 | 60% |
| hMC3r | $EC_{50}$ | NC | -1% |
| hMC4r | $EC_{50}$ | NC | 3% |

-continued

| No. | Structure | Amino Acid Sequence and Functional Data |
|---|---|---|
| 36 | 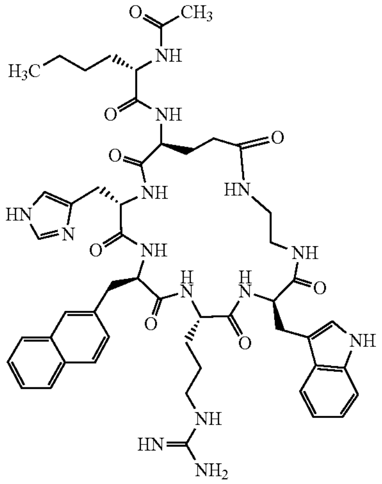 [SMILES: CCCC[C@H](NC(C)=O)C(=O)N[C@H]1CCC(=O)NCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Nle-Glu-His-D-Nal 2-Arg-D-Trp<br>NH——$(CH_2)_2$——NH |

| Receptor | Assay | Value (nM) | % |
|---|---|---|---|
| mMC1r | $EC_{50}$ | 3 | 53% |
| hMC3r | $EC_{50}$ | NC | -1% |
| hMC4r | $EC_{50}$ | NC | 1% |

| No. | Structure | Amino Acid Sequence and Functional Data |
|---|---|---|
| 37 | 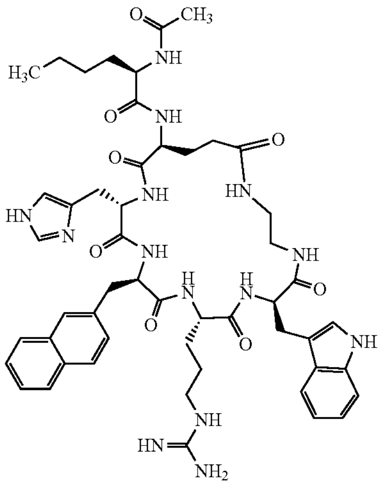 [SMILES: CCCC[C@@H](NC(C)=O)C(=O)N[C@H]1CCC(=O)NCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-D-Nle-Glu-His-D-Nal 2-Arg-D-Trp<br>NH——$(CH_2)_2$——NH |

| Receptor | Assay | Value (nM) | % |
|---|---|---|---|
| mMC1r | $EC_{50}$ | 4 | 54% |
| hMC3r | $EC_{50}$ | NC | -1% |
| hMC4r | $EC_{50}$ | NC | 0% |

| No. | Structure | Amino Acid Sequence and Functional Data |
|---|---|---|
| 38 | 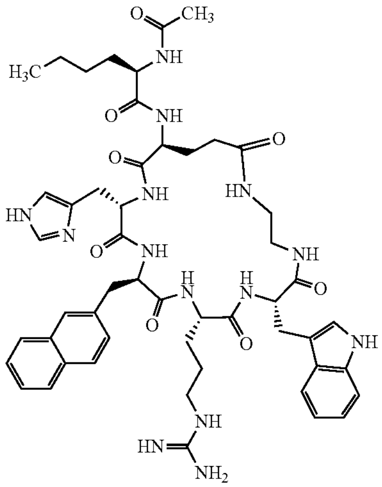 [SMILES: CCCC[C@@H](NC(C)=O)C(=O)N[C@H]1CCC(=O)NCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-D-Nle-Glu-His-D-Nal 2-Arg-Trp<br>NH——$(CH_2)_2$——NH |

| Receptor | Assay | Value (nM) | % |
|---|---|---|---|
| mMC1r | $EC_{50}$ | 0.6 | 68% |
| hMC3r | $EC_{50}$ | NC | 0% |
| hMC4r | $EC_{50}$ | NC | 0% |
| hMC5r* | $EC_{50}$ | 0.1 | 33% |

-continued

| No. | Structure | Amino Acid Sequence and Functional Data |
|---|---|---|
| 39 | 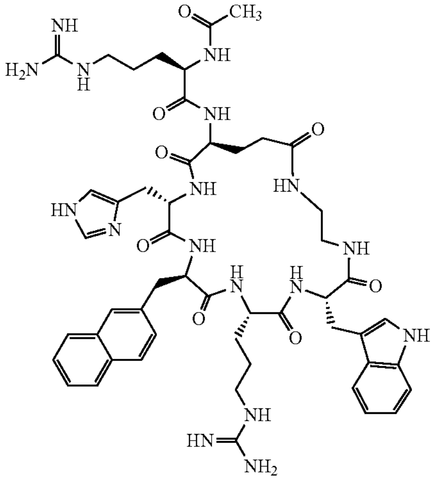 [SMILES: CC(=O)N[C@H](CCCNC(=N)N)C(=O)N[C@H]1CCC(=O)NCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-D-Arg-Glu-His-D-Nal 2-Arg-Trp<br>NH—$(CH_2)_2$—NH |
| 40 | 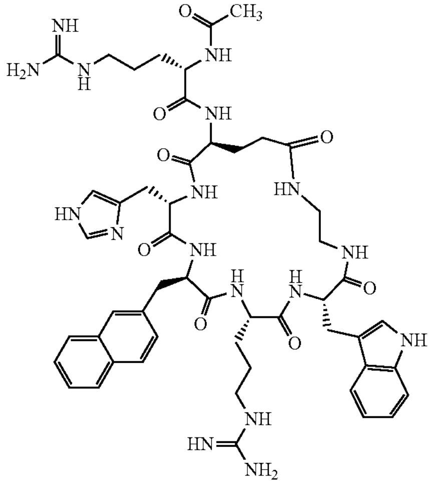 [SMILES: CC(=O)N[C@@H](CCCNC(=N)N)C(=O)N[C@H]1CCC(=O)NCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Arg-Glu-His-D-Nal 2-Arg-Trp<br>NH—$(CH_2)_2$—NH |
| 41 | 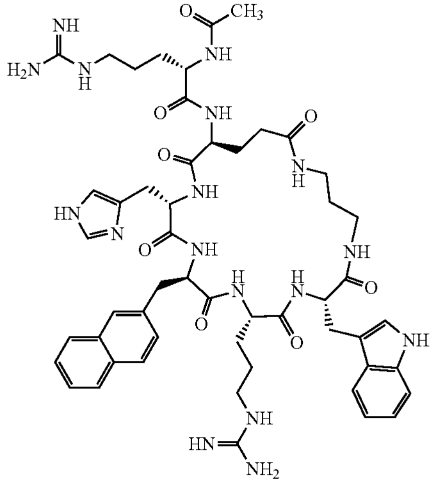 [SMILES: CC(=O)N[C@@H](CCCNC(=N)N)C(=O)N[C@H]1CCC(=O)NCCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Arg-Glu-His-D-Nal 2-Arg-Trp<br>NH—$(CH_2)_3$—NH |

Functional data for compound 39:

| Receptor | Assay | Value (nM) | % |
|---|---|---|---|
| mMC1r | $EC_{50}$ | 15 | 47% |
| hMC3r | $EC_{50}$ | NC | -1% |
| hMC4r | $EC_{50}$ | NC | 1% |

Functional data for compound 40:

| Receptor | Assay | Value (nM) | % |
|---|---|---|---|
| mMC1r | $EC_{50}$ | 15 | 47% |
| hMC3r | $EC_{50}$ | NC | 0% |
| hMC4r | $EC_{50}$ | NC | 1% |

Functional data for compound 41:

| Receptor | Assay | Value (nM) | % |
|---|---|---|---|
| mMC1r | $EC_{50}$ | 4 | 51% |
| hMC3r | $EC_{50}$ | NC | 0% |
| hMC4r | $EC_{50}$ | NC | 2% |

-continued

| No. | Structure | Amino Acid Sequence and Functional Data |
|---|---|---|
| 42 | 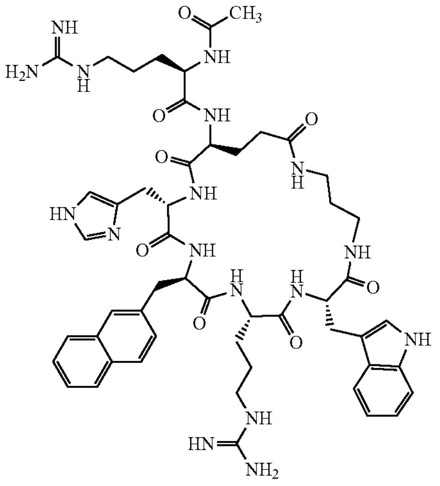 [SMILES: CC(=O)N[C@H](CCCNC(=N)N)C(=O)N[C@H]1CCC(=O)NCCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-D-Arg-Glu-His-D-Nal 2-Arg-Trp<br>NH—$(CH_2)_3$—NH |

| Receptor | Assay | Value (nM) | % |
|---|---|---|---|
| mMC1r | $EC_{50}$ | 5 | 52% |
| hMC3r | $EC_{50}$ | NC | -2% |
| hMC4r | $EC_{50}$ | NC | 2% |

| No. | Structure | Amino Acid Sequence and Functional Data |
|---|---|---|
| 43 | 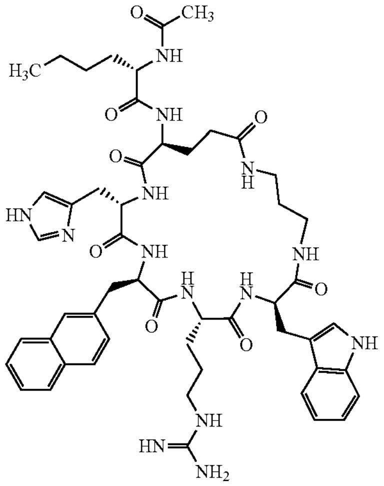 [SMILES: CCCC[C@H](NC(C)=O)C(=O)N[C@H]1CCC(=O)NCCCNC(=O)[C@@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Nle-Glu-His-D-Nal 2-Arg-D-Trp<br>NH—$(CH_2)_3$—NH |

| Receptor | Assay | Value (nM) | % |
|---|---|---|---|
| mMC1r | $EC_{50}$ | 0.06 | 53% |
| hMC3r | $EC_{50}$ | NC | -1% |
| hMC4r | $EC_{50}$ | NC | -1% |
| hMC5r* | $EC_{50}$ | 0.1 | 44% |

| No. | Structure | Amino Acid Sequence and Functional Data |
|---|---|---|
| 44 | 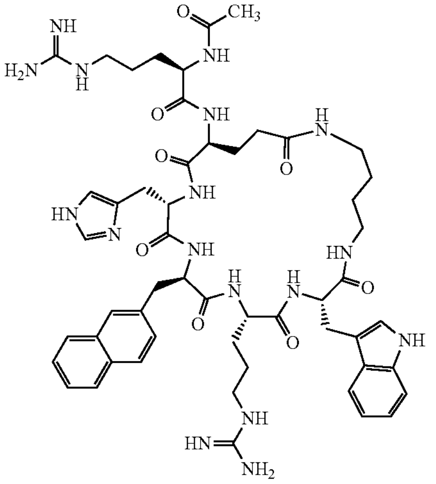 [SMILES: CC(=O)N[C@H](CCCNC(=N)N)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-D-Arg-Glu-His-D-Nal 2-Arg-Trp<br>NH—$(CH_2)_4$—NH |

| Receptor | Assay | Value (nM) | % |
|---|---|---|---|
| mMC1r | $EC_{50}$ | 8 | 41% |
| hMC3r | $EC_{50}$ | NC | -1% |
| hMC4r | $EC_{50}$ | NC | 6% |

-continued

| No. | Structure | Amino Acid Sequence and Functional Data |
|---|---|---|

45

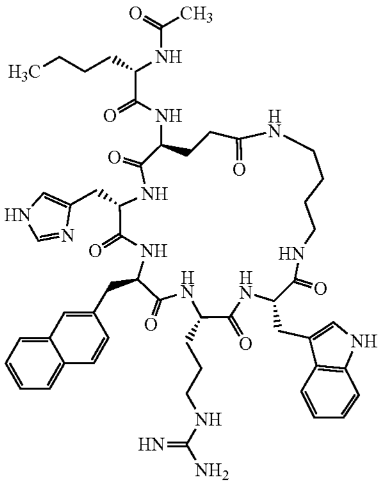 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O]

Ac-Nle-Glu-His-D-Nal 2-Arg-Trp

NH—(CH$_2$)$_4$—NH

| Receptor | Assay | Value (nM) | % |
|---|---|---|---|
| mMC1r | EC$_{50}$ | 0.149 | 54% |
| hMC3r | EC$_{50}$ | NC | -1% |
| hMC4r | EC$_{50}$ | NC | 3% |
| hMC5r* | EC$_{50}$ | 0.03 | 69% |

46

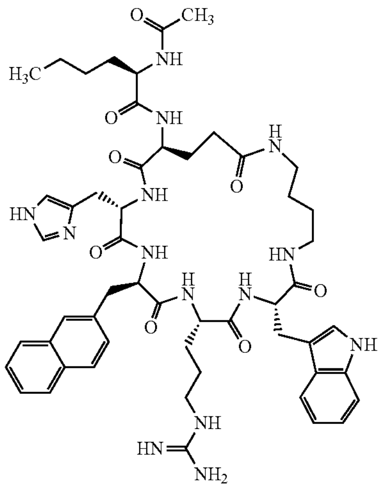 [SMILES: CCCC[C@@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O]

Ac-D-Nle-Glu-His-D-Nal 2-Arg-Trp

NH—(CH$_2$)$_4$—NH

| Receptor | Assay | Value (nM) | % |
|---|---|---|---|
| hMC1r | EC$_{50}$ | 0.175 | 78% |
| mMC1r | EC$_{50}$ | 0.258 | 49% |
| hMC3r | EC$_{50}$ | NC | -2% |
| hMC4r | EC$_{50}$ | NC | 3% |
| hMC5r* | EC$_{50}$ | 0.2 | 65% |

47

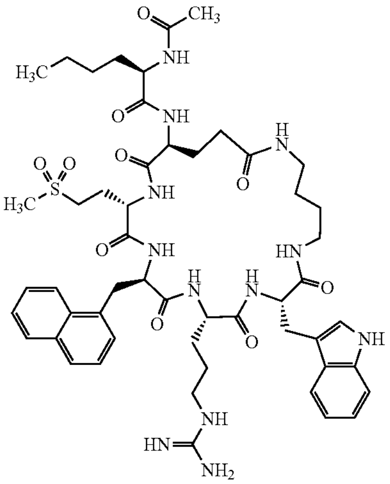 [SMILES: CCCC[C@@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](CCS(C)(=O)=O)NC1=O]

Ac-D-Nle-Glu-Met(O$_2$)-D-Nal 1-Arg-Trp

NH—(CH$_2$)$_4$—NH

| Receptor | Assay | Value (nM) | % |
|---|---|---|---|
| hMC1r | EC$_{50}$ | 1 | 80% |
| mMC1r | EC$_{50}$ | 2 | 60% |
| hMC3r | EC$_{50}$ | NC | 11% |
| hMC4r | EC$_{50}$ | 3 | 32% |
| hMC5r* | EC$_{50}$ | 0.94 | 74% |

-continued

| No. | Structure | Amino Acid Sequence and Functional Data |
|---|---|---|
| 48 | 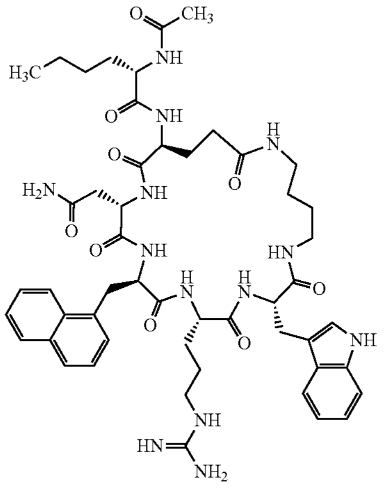 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](CC(N)=O)NC1=O] | Ac-D-Nle-Glu-Asn-D-Nal 1-Arg-Trp<br>NH—(CH<sub></sub>$_2$)$_4$—NH |

| Receptor | Assay | Value (nM) | % |
|---|---|---|---|
| mMC1r | $EC_{50}$ | 1 | 63% |
| hMC3r | $EC_{50}$ | 2 | 19% |
| hMC4r | $EC_{50}$ | 1.0 | 62% |
| hMC5r* | $EC_{50}$ | 5 | 87% |

| No. | Structure | Amino Acid Sequence and Functional Data |
|---|---|---|
| 49 | 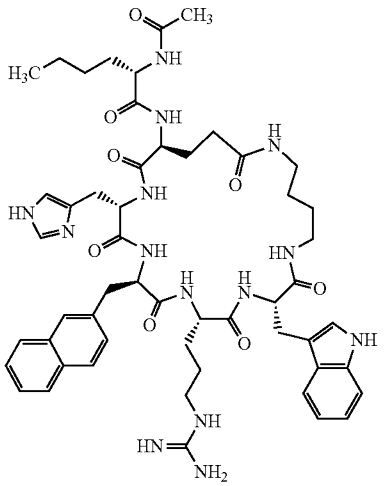 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc3ccccc3c2)NC(=O)[C@H](Cc2c[nH]cn2)NC1=O] | Ac-Nle-Glu-His-D-Nal 2-Arg-Trp<br>NH—$(CH_2)_4$—NH |

| Receptor | Assay | Value (nM) | % |
|---|---|---|---|
| mMC1r | $EC_{50}$ | 0.09 | 55% |
| hMC3r | $EC_{50}$ | NC | -4% |
| hMC4r | $EC_{50}$ | NC | 11% |
| hMC5r* | $EC_{50}$ | 0.41 | 56% |

| No. | Structure | Amino Acid Sequence and Functional Data |
|---|---|---|
| 50 | 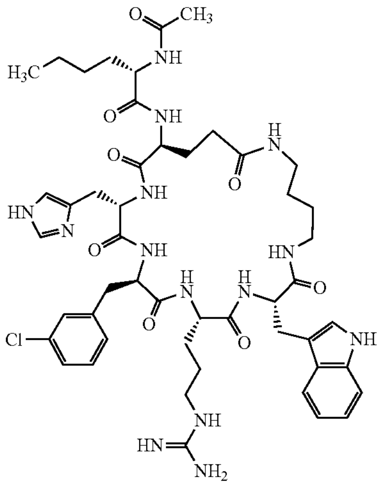 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2cccc(Cl)c2)NC(=O)[C@H](Cc2c[nH]cn2)NC1=O] | Ac-Nle-Glu-His-D-Phe(3-Cl)-Arg-Trp<br>NH—$(CH_2)_4$—NH |

| Receptor | Assay | Value (nM) | % |
|---|---|---|---|
| hMC1r | $EC_{50}$ | 0.12 | 86% |
| mMC1r | $EC_{50}$ | 0.068 | 77% |
| hMC3r | $EC_{50}$ | 0.85 | 26% |
| hMC5r | $EC_{50}$ | 0.8 | 76% |
| hMC5r* | $EC_{50}$ | 0.61 | 26% |

-continued

| No. | Structure | Amino Acid Sequence and Functional Data |
|---|---|---|

51

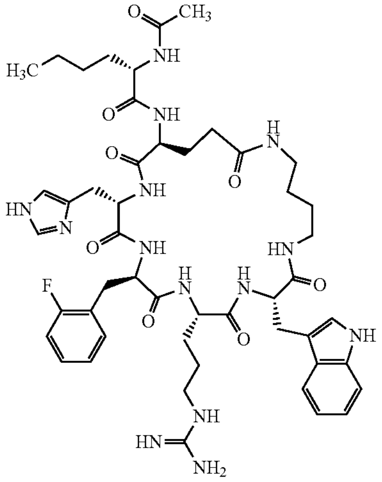

Ac-Nle-Glu-His-D-Phe(2-F)-Arg-Trp

NH—$(CH_2)_4$—NH

| Receptor | Assay | Value (nM) | % |
|---|---|---|---|
| hMC1r | $EC_{50}$ | 0.05 | 131% |
| mMC1r | $EC_{50}$ | 0.067 | 100% |
| mMC1r* | $EC_{50}$ | 0.018 | 116% |
| hMC3r | $EC_{50}$ | 0.157 | 101% |
| hMC3r* | $EC_{50}$ | 0.19 | 128% |
| hMC4r | $EC_{50}$ | 0.05 | 135% |
| hMC4r* | $EC_{50}$ | 0.009 | 91% |
| hMC5r | $EC_{50}$ | 1 | 59% |
| hMC5r* | $EC_{50}$ | 3 | 47% |

52

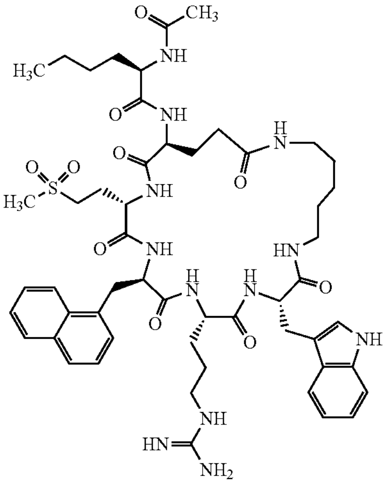 [SMILES: CCCC[C@@H](NC(C)=O)C(=O)N[C@H]1CCC(=O)NCCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](CCS(C)(=O)=O)NC1=O]

Ac-D-Nle-Glu-Met($O_2$)-D-Nal 1-Arg-Trp

NH—$(CH_2)_5$—NH

| Receptor | Assay | Value (nM) | % |
|---|---|---|---|
| hMC1r | $EC_{50}$ | 1 | 88% |
| mMC1r | $EC_{50}$ | 0.6 | 66% |
| hMC3r | $EC_{50}$ | NC | 4% |
| hMC4r | $EC_{50}$ | 4 | 29% |
| hMC5r* | $EC_{50}$ | 1 | 65% |

53

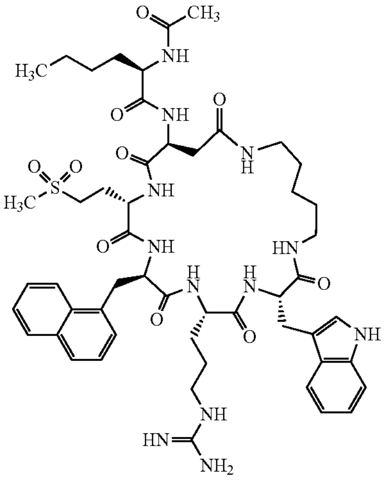 [SMILES: CCCC[C@@H](NC(C)=O)C(=O)N[C@H]1CC(=O)NCCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](CCS(C)(=O)=O)NC1=O]

Ac-D-Nle-Asp-Met($O_2$)-D-Nal 1-Arg-Trp

NH—$(CH_2)_5$—NH

| Receptor | Assay | Value (nM) | % |
|---|---|---|---|
| hMC1r | $EC_{50}$ | 7 | 90% |
| mMC1r | $EC_{50}$ | 18 | 66% |
| hMC3r | $EC_{50}$ | NC | 4% |
| hMC4r | $EC_{50}$ | 5 | 33% |
| hMC5r* | $EC_{50}$ | 31 | 95% |

-continued

| No. | Structure | Amino Acid Sequence and Functional Data |
|---|---|---|

54

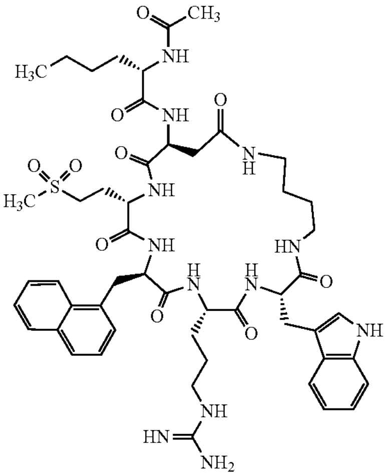 [SMILES: CCCC[C@H](NC(C)=O)C(=O)N[C@H]1CC(=O)NCCCCNC(=O)[C@H](Cc2c[nH]c3ccccc23)NC(=O)[C@H](CCCNC(=N)N)NC(=O)[C@@H](Cc2cccc3ccccc23)NC(=O)[C@H](CCS(C)(=O)=O)NC1=O]

Ac-Nle-Asp-Met($O_2$)-D-Nal 1-Arg-Trp

NH——($CH_2$)$_4$——NH

| Receptor | Assay | Value (nM) | % |
|---|---|---|---|
| hMC1r | $EC_{50}$ | 8 | 97% |
| mMC1r | $EC_{50}$ | 3 | 73% |
| mMC1r | *$EC_{50}$ | 12 | 86% |
| hMC3r | $EC_{50}$ | NC | 9% |
| hMC3r | *$EC_{50}$ | NC | 11% |
| hMC4r | $EC_{50}$ | 1.1 | 21% |
| hMC4r | *$EC_{50}$ | 2 | 54% |
| hMC5r | $EC_{50}$ | 2 | 66% |
| hMC5r | *$EC_{50}$ | 23 | 100% |

55

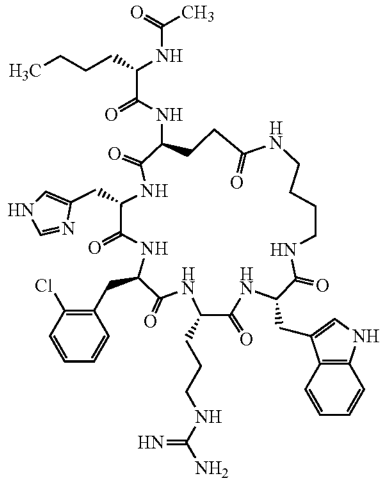 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2Cl)NC(=O)[C@H](Cc2c[nH]cn2)NC1=O]

Ac-Nle-Glu-His-D-Phe(2-Cl)-Arg-Trp

NH——($CH_2$)$_4$——NH

| Receptor | Assay | Value (nM) | % |
|---|---|---|---|
| hMC1r | $EC_{50}$ | 0.03 | 115% |
| mMC1r | $EC_{50}$ | 0.01 | 102% |
| mMC1r* | $EC_{50}$ | 0.033 | 117% |
| hMC3r | $EC_{50}$ | 0.057 | 109% |
| hMC4r | $EC_{50}$ | 0.03 | 132% |
| hMC5r* | $EC_{50}$ | 1 | 33% |

56

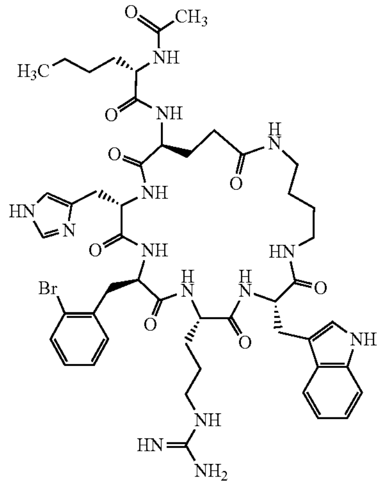 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2Br)NC(=O)[C@H](Cc2c[nH]cn2)NC1=O]

Ac-Nle-Glu-His-D-Phe(2-Br)-Arg-Trp

NH——($CH_2$)$_4$——NH

| Receptor | Assay | Value (nM) | % |
|---|---|---|---|
| hMC1r | $EC_{50}$ | 0.03 | 139% |
| mMC1r | $EC_{50}$ | 0.04 | 100% |
| mMC1r* | $EC_{50}$ | 0.025 | 105% |
| hMC3r | $EC_{50}$ | 0.223 | 107% |
| hMC4r | $EC_{50}$ | 0.06 | 136% |
| hMC5r* | $EC_{50}$ | 2 | 27% |

-continued

| No. | Structure | Amino Acid Sequence and Functional Data |
|---|---|---|

57

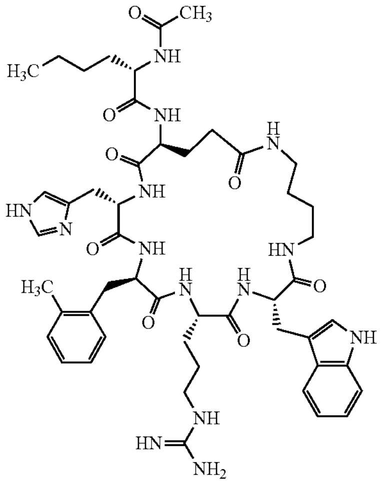 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2C)NC(=O)[C@H](Cc2c[nH]cn2)NC1=O]

Ac-Nle-Glu-His-D-Phe(2-Me)-Arg-Trp

NH——$(CH_2)_4$——NH

| Receptor | Assay | Value (nM) | % |
|---|---|---|---|
| mMC1r | $EC_{50}$ | 0.02 | 85% |
| hMC3r | $EC_{50}$ | 0.137 | 97% |
| hMC4r | $EC_{50}$ | 0.1 | 104% |
| hMC5r | $EC_{50}$ | 2 | 25% |
| hMC5r* | $EC_{50}$ | 2 | 36% |

58

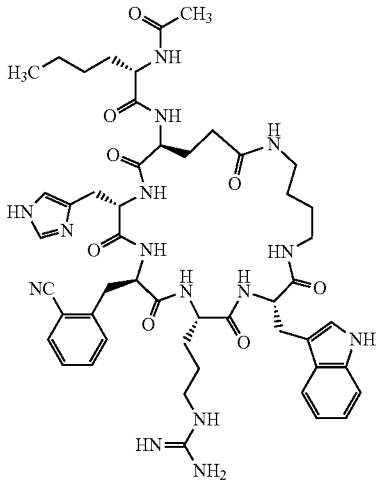 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2C#N)NC(=O)[C@H](Cc2c[nH]cn2)NC1=O]

Ac-Nle-Glu-His-D-Phe(2-CN)-Arg-Trp

NH——$(CH_2)_4$——NH

| Receptor | Assay | Value (nM) | % |
|---|---|---|---|
| mMC1r | $EC_{50}$ | 0.02 | 89% |
| hMC3r | $EC_{50}$ | 0.5 | 98% |
| hMC4r | $EC_{50}$ | 0.06 | 121% |
| hMC5r | $EC_{50}$ | 15 | 28% |
| hMC5r* | $EC_{50}$ | 39 | 37% |

59

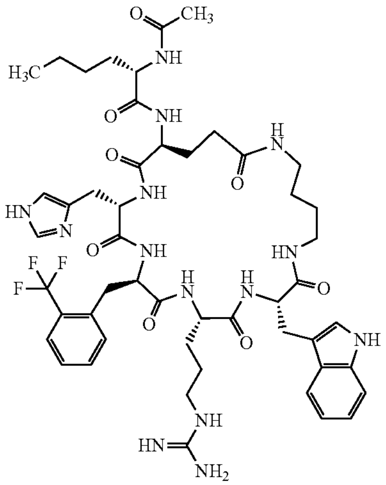 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2C(F)(F)F)NC(=O)[C@H](Cc2c[nH]cn2)NC1=O]

Ac-Nle-Glu-His-D-Phe(2-CF3)-Arg-Trp

NH——$(CH_2)_4$——NH

| Receptor | Assay | Value (nM) | % |
|---|---|---|---|
| mMC1r | $EC_{50}$ | 0.02 | 68% |
| hMC3r | $EC_{50}$ | 2 | 83% |
| hMC4r | $EC_{50}$ | 0.2 | 127% |
| hMC5r | $EC_{50}$ | 1 | 28% |
| hMC5r* | $EC_{50}$ | 1 | 51% |

-continued

| No. | Structure | Amino Acid Sequence and Functional Data |
|---|---|---|

60

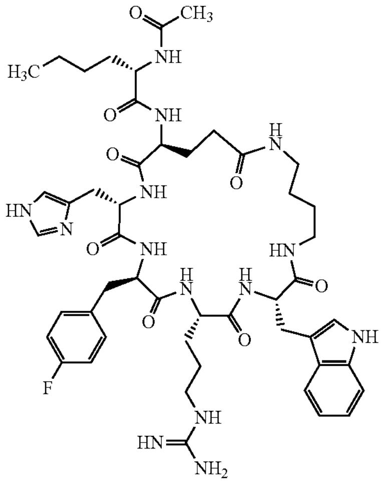 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O]

Ac-Nle-Glu-His-D-Phe(4-F)-Arg-Trp

NH——$(CH_2)_4$——NH

| Receptor | Assay | Value (nM) | % |
|---|---|---|---|
| hMC1r | $EC_{50}$ | 0.129 | 87% |
| mMC1r | $EC_{50}$ | 0.02 | 89% |
| mMC1r* | $EC_{50}$ | 0.013 | 97% |
| hMC3r | $EC_{50}$ | 0.77 | 115% |
| hMC3r* | $EC_{50}$ | 0.022 | 95% |
| hMC4r | $EC_{50}$ | 2 | 136% |
| hMC4r* | $EC_{50}$ | 0.014 | 116% |
| hMC5r | $EC_{50}$ | 0.15 | 55% |
| hMC5r* | $EC_{50}$ | 0.387 | 59% |

61

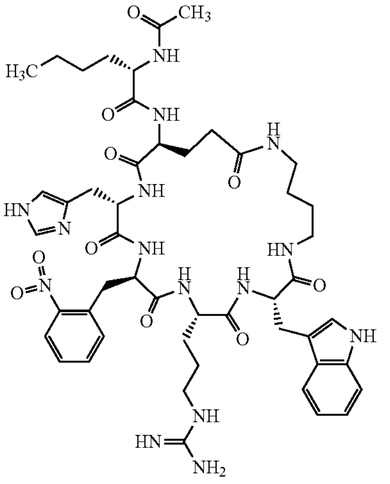 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccccc2[N+](=O)[O-])NC(=O)[C@H](Cc2c[nH]cn2)NC1=O]

Ac-Nle-Glu-His-D-Phe(2-$NO_2$)-Arg-Trp

NH——$(CH_2)_4$——NH

| Receptor | Assay | Value (nM) | % |
|---|---|---|---|
| mMC1r | $EC_{50}$ | 0.03 | 84% |
| hMC3r | $EC_{50}$ | 0.7 | 112% |
| hMC4r | $EC_{50}$ | 5 | 108% |
| hMC5r | $EC_{50}$ | 5 | 36% |
| hMC5r* | $EC_{50}$ | 35 | 67% |

62

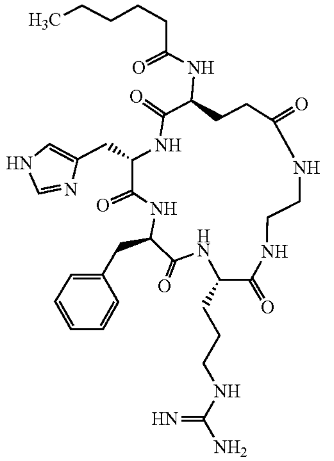 [SMILES: CCCCCC(=O)N[C@H]1CCC(=O)NCCNC(=O)[C@H](CCCNC(=N)N)NC(=O)[C@@H](Cc2ccccc2)NC(=O)[C@H](Cc2c[nH]cn2)NC1=O]

Hexanoyl-Glu-His-D-Phe-Arg

NH—$(CH_2)_2$—NH

| Receptor | Assay | Value (nM) | % |
|---|---|---|---|
| mMC1r | $EC_{50}$ | 1250 | 65% |
| hMC3r | $EC_{50}$ | NC | 0% |
| hMC4r | $EC_{50}$ | NC | 0% |
| hMC5r | $EC_{50}$ | NC | 0% |
| hMC5r* | $EC_{50}$ | NC | 4% |

-continued

| No. | Structure | Amino Acid Sequence and Functional Data |
|---|---|---|
| 63 | 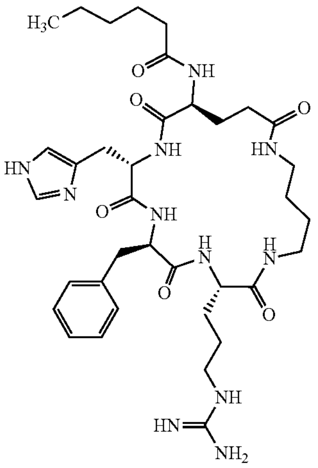 [SMILES: CCCCCC(=O)N[C@H]1CCC(=O)NCCCCNC(=O)[C@H](CCCNC(=N)N)NC(=O)[C@@H](Cc2ccccc2)NC(=O)[C@H](Cc2c[nH]cn2)NC1=O] | Hexanoyl-Glu-His-D-Phe-Arg<br>NH—$(CH_2)_4$—NH |
| 64 | 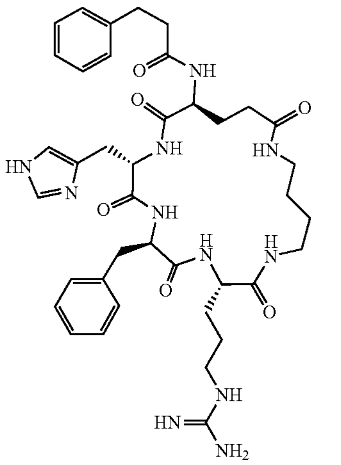 [SMILES: N=C(N)NCCC[C@@H]1NC(=O)[C@@H](Cc2ccccc2)NC(=O)[C@H](Cc2c[nH]cn2)NC(=O)[C@@H](NC(=O)CCc2ccccc2)CCC(=O)NCCCCNC1=O] | 3-phenylpropanoyl-Glu-His-D-Phe-Arg<br>NH—$(CH_2)_4$—NH |
| 65 | 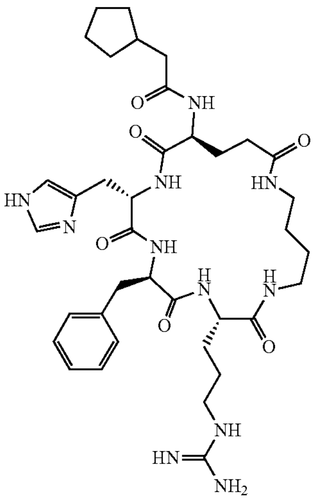 [SMILES: N=C(N)NCCC[C@@H]1NC(=O)[C@@H](Cc2ccccc2)NC(=O)[C@H](Cc2c[nH]cn2)NC(=O)[C@@H](NC(=O)CC2CCCC2)CCC(=O)NCCCCNC1=O] | cyclopentylacetyl-Glu-His-D-Phe-Arg<br>NH—$(CH_2)_4$—NH |

Compound 63:

| Receptor | Assay | Value (nM) | % |
|---|---|---|---|
| hMC1r | $EC_{50}$ | 7 | 86% |
| mMC1r | $EC_{50}$ | 655 | 77% |
| mMC1r* | $EC_{50}$ | 3250 | 62% |
| hMC3r | $EC_{50}$ | NC | 0% |
| hMC3r* | $EC_{50}$ | NC | 12% |
| hMC4r | $EC_{50}$ | NC | 19% |
| hMC4r* | $EC_{50}$ | NC | 33% |
| hMC5r* | $EC_{50}$ | NC | 2% |

Compound 64:

| Receptor | Assay | Value (nM) | % |
|---|---|---|---|
| hMC1r | $EC_{50}$ | 20 | 80% |
| hMC4r | $EC_{50}$ | NC | 5% |
| hMC5r | $EC_{50}$ | NC | 2% |

Compound 65:

| Receptor | Assay | Value (nM) | % |
|---|---|---|---|
| hMC1r | $EC_{50}$ | 1 | 102% |
| mMC1r* | $EC_{50}$ | 1400 | 72% |
| hMC4r | $EC_{50}$ | NC | 12% |
| hMC5r | $EC_{50}$ | NC | 4% |

-continued

| No. | Structure | Amino Acid Sequence and Functional Data |
|---|---|---|
| 66 | 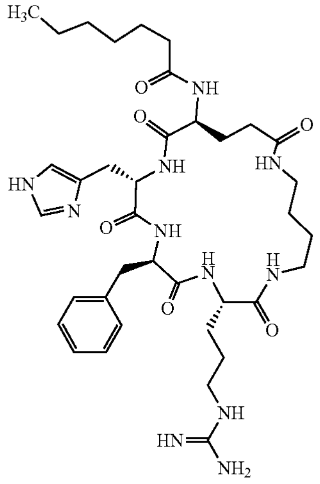 [SMILES: CCCCCCC(=O)N[C@H]1CCC(=O)NCCCCNC(=O)[C@H](CCCNC(=N)N)NC(=O)[C@@H](Cc2ccccc2)NC(=O)[C@H](Cc2c[nH]cn2)NC1=O] | Hexanoyl-Glu-His-D-Phe-Arg-Trp<br>NH—$(CH_2)_4$—NH |

| Receptor | Assay | Value (nM) | % |
|---|---|---|---|
| hMC1r | $EC_{50}$ | 2 | 98% |
| mMC1r | $EC_{50}$ | 30 | 63% |
| hMC4r | $EC_{50}$ | NC | 22% |
| hMC5r | $EC_{50}$ | NC | 0% |

| No. | Structure | Amino Acid Sequence and Functional Data |
|---|---|---|
| 67 | 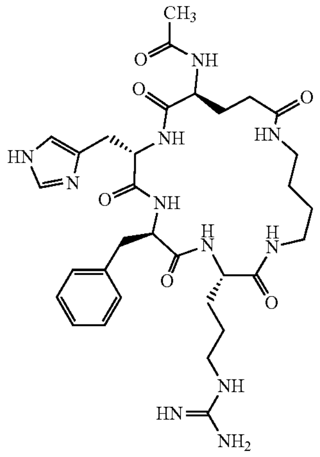 [SMILES: CC(=O)N[C@H]1CCC(=O)NCCCCNC(=O)[C@H](CCCNC(=N)N)NC(=O)[C@@H](Cc2ccccc2)NC(=O)[C@H](Cc2c[nH]cn2)NC1=O] | Ac-Glu-His-D-Phe-Arg<br>NH—$(CH_2)_4$—NH |

| Receptor | Assay | Value (nM) | % |
|---|---|---|---|
| hMC1r | $EC_{50}$ | 221 | 89% |
| hMC4r | $EC_{50}$ | 1300 | 63% |
| hMC5r | $EC_{50}$ | 4617 | 46% |

| No. | Structure | Amino Acid Sequence and Functional Data |
|---|---|---|
| 68 | 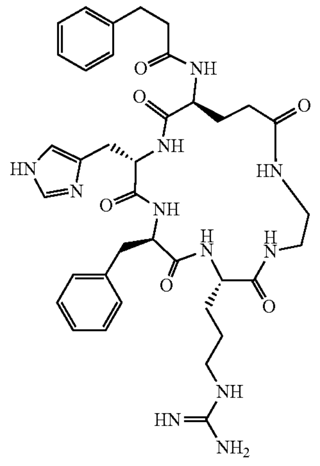 [SMILES: N=C(N)NCCC[C@@H]1NC(=O)[C@@H](Cc2ccccc2)NC(=O)[C@H](Cc2c[nH]cn2)NC(=O)[C@@H](NC(=O)CCc2ccccc2)CCC(=O)NCCNC1=O] | 3-phenylpropanoyl-Glu-His-D-Phe-Arg<br>NH—$(CH_2)_2$—NH |

| Receptor | Assay | Value (nM) | % |
|---|---|---|---|
| hMC1r | $EC_{50}$ | 64 | 93% |
| hMC4r | $EC_{50}$ | NC | 29% |
| hMC5r | $EC_{50}$ | NC | -1% |

-continued

| No. | Structure | Amino Acid Sequence and Functional Data |
|---|---|---|
| 69 | 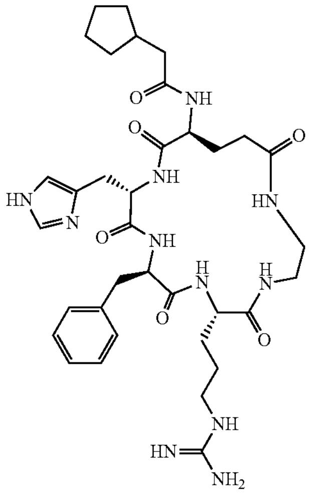 [SMILES: N=C(N)NCCC[C@@H]1NC(=O)[C@@H](Cc2ccccc2)NC(=O)[C@H](Cc2c[nH]cn2)NC(=O)[C@@H](NC(=O)CC2CCCC2)CCC(=O)NCCNC1=O] | cyclopentylacetyl-Glu-His-D-Phe-Arg<br>NH—(CH$_2$)$_2$—NH |
| 70 | 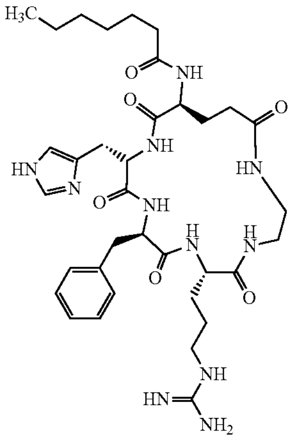 | Heptanoyl-Glu-His-D-Phe-Arg<br>NH—(CH$_2$)$_2$—NH |
| 71 | 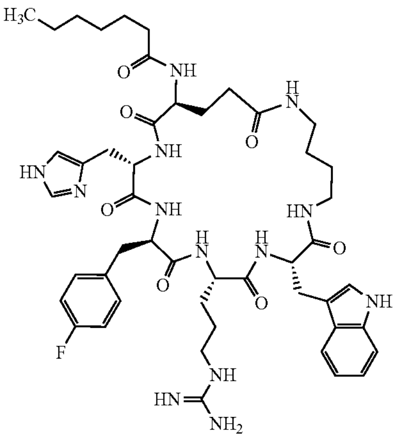 [SMILES: CCCCCCC(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O] | Heptanoyl-Glu-His-D-Phe(4-F)-Arg-Trp<br>NH—(CH$_2$)$_4$—NH |

Compound 69:

| Receptor | Assay | Value (nM) | % |
|---|---|---|---|
| hMC1r | $EC_{50}$ | 2 | 82% |
| hMC4r | $EC_{50}$ | NC | 19% |
| hMC5r | $EC_{50}$ | NC | 5% |

Compound 70:

| Receptor | Assay | Value (nM) | % |
|---|---|---|---|
| hMC1r | $EC_{50}$ | 10 | 96% |
| hMC4r | $EC_{50}$ | NC | 9% |
| hMC5r | $EC_{50}$ | NC | -2.5% |

Compound 71:

| Receptor | Assay | Value (nM) | % |
|---|---|---|---|
| hMC1r | $EC_{50}$ | 0.018 | 100% |
| mMC1r | $EC_{50}$ | 0.017 | 78% |
| mMC1r* | $EC_{50}$ | 0.011 | 95% |
| hMC3r | $EC_{50}$ | 0.03 | 84% |
| hMC3r* | $EC_{50}$ | 0.028 | 117% |
| hMC4r | $EC_{50}$ | 0.15 | 108% |
| hMC4r* | $EC_{50}$ | 0.012 | 109% |
| hMC5r | $EC_{50}$ | 0.275 | 70% |
| hMC5r* | $EC_{50}$ | 0.67 | 73% |

-continued

| No. | Structure | Amino Acid Sequence and Functional Data |
|---|---|---|

72

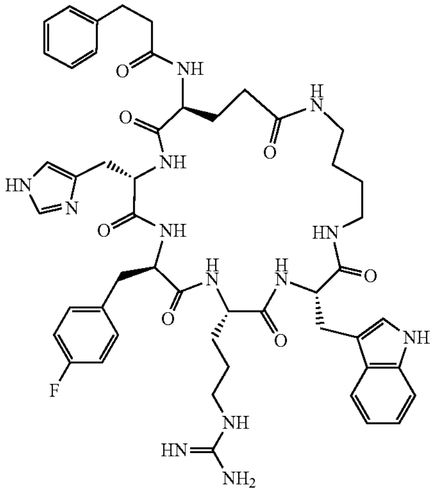 [SMILES: N=C(N)NCCC[C@@H]1NC(=O)[C@@H](Cc2ccc(F)cc2)NC(=O)[C@H](Cc2c[nH]cn2)NC(=O)[C@@H](NC(=O)CCc2ccccc2)CCC(=O)NCCCCNC(=O)[C@H](Cc2c[nH]c3ccccc23)NC1=O]

3-phenylpropanoyl-Glu-His-D-Phe(4-F)-Arg-Trp
NH———$(CH_2)_4$———NH

| Receptor | Assay | Value (nM) | % |
|---|---|---|---|
| hMC1r | $EC_{50}$ | 0.037 | 103% |
| mMC1r | $EC_{50}$ | 0.02 | 79% |
| mMC1r* | $EC_{50}$ | 0.04 | 108% |
| hMC3r | $EC_{50}$ | 0.09 | 81% |
| hMC3r* | $EC_{50}$ | 0.082 | 107% |
| hMC4r | $EC_{50}$ | 0.075 | 52% |
| hMC4r* | $EC_{50}$ | 0.011 | 100% |
| hMC5r | $EC_{50}$ | 3 | 84% |
| hMC5r* | $EC_{50}$ | 5 | 77% |

73

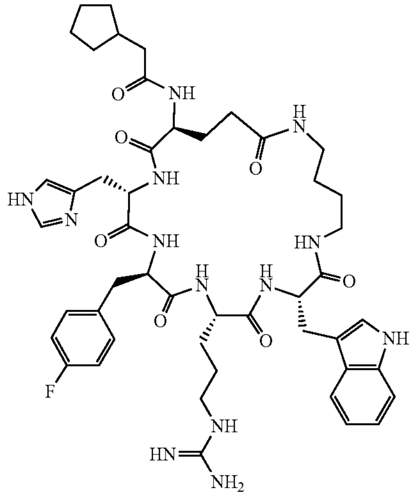 [SMILES: N=C(N)NCCC[C@@H]1NC(=O)[C@@H](Cc2ccc(F)cc2)NC(=O)[C@H](Cc2c[nH]cn2)NC(=O)[C@@H](NC(=O)CC2CCCC2)CCC(=O)NCCCCNC(=O)[C@H](Cc2c[nH]c3ccccc23)NC1=O]

cyclopentylacetyl-Glu-His-D-Phe(4-F)-Arg-Trp
NH———$(CH_2)_4$———NH

| Receptor | Assay | Value (nM) | % |
|---|---|---|---|
| hMC1r | $EC_{50}$ | 0.15 | 114% |
| mMC1r* | $EC_{50}$ | 0.017 | 95% |
| hMC4r | $EC_{50}$ | 0.3 | 78% |
| hMC5r | $EC_{50}$ | 0.8 | 62% |
| hMC5r* | $EC_{50}$ | 2 | 64% |

74

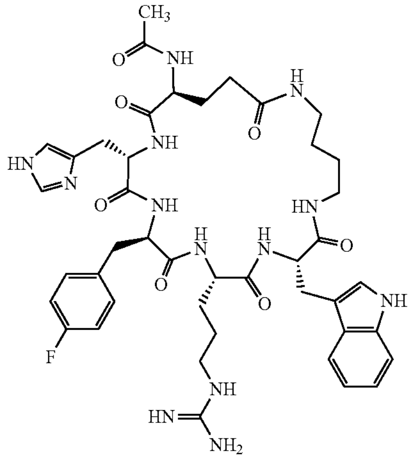 [SMILES: CC(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O]

Ac-Glu-His-D-Phe(4-F)-Arg-Trp
NH———$(CH_2)_4$———NH

| Receptor | Assay | Value (nM) | % |
|---|---|---|---|
| hMC1r | $EC_{50}$ | 0.2 | 101% |
| mMC1r* | $EC_{50}$ | 0.16 | 95% |
| hMC4r | $EC_{50}$ | 0.3 | 98% |
| hMC5r | $EC_{50}$ | 107 | 63% |
| hMC5r* | $EC_{50}$ | 2300 | 64% |

-continued

| No. | Structure | Amino Acid Sequence and Functional Data |
|---|---|---|
| 75 | 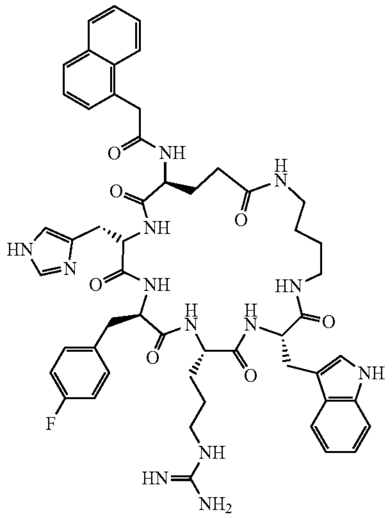 | 1-Naphthylacetyl-Glu-His-D-Phe(4-F)-Arg-Trp<br>NH—$(CH_2)_4$—NH (bridging Glu and Trp) |
| 76 | 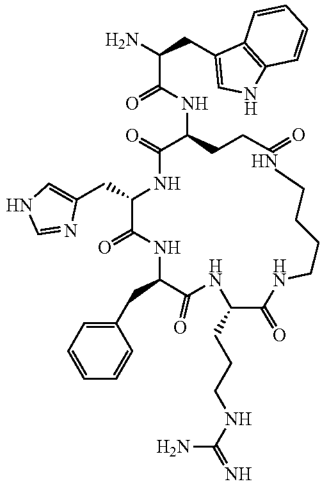 | Trp-Glu-His-D-Phe-Arg<br>NH—$(CH_2)_4$—NH (bridging Glu and Arg) |
| 77 | 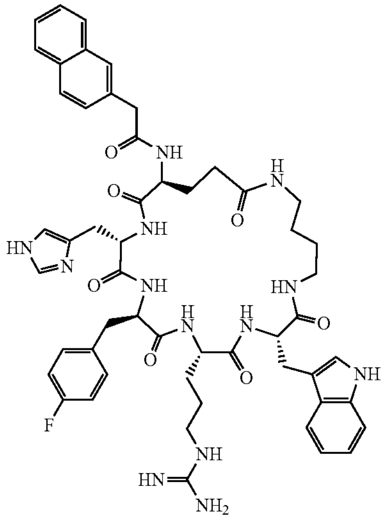 [SMILES: N=C(N)NCCC[C@@H]1NC(=O)[C@@H](Cc2ccc(F)cc2)NC(=O)[C@H](Cc2c[nH]cn2)NC(=O)[C@@H](NC(=O)Cc2ccc3ccccc3c2)CCC(=O)NCCCCNC(=O)[C@H](Cc2c[nH]c3ccccc23)NC1=O] | 2-Naphthylacetyl-Glu-His-D-Phe(4-F)-Arg-Trp<br>NH—$(CH_2)_4$—NH (bridging Glu and Trp) |

Compound 75:

| Receptor | Assay | Value (nM) | % |
|---|---|---|---|
| hMC1r | $EC_{50}$ | 0.047 | 88% |
| hMC4r | $EC_{50}$ | 0.4 | 93% |
| hMC5r | $EC_{50}$ | 0.25 | 71% |

Compound 76:

| Receptor | Assay | Value (nM) | % |
|---|---|---|---|
| hMC1r | $EC_{50}$ | 66 | 88% |
| hMC4r | $EC_{50}$ | NC | -1% |
| hMC5r | $EC_{50}$ | NC | 0% |

Compound 77:

| Receptor | Assay | Value (nM) | % |
|---|---|---|---|
| hMC1r | $EC_{50}$ | 0.082 | 98% |
| mMC1r | $EC_{50}$ | 0.019 | 84% |
| mMC1r* | $EC_{50}$ | 0.007 | 84% |
| hMC3r | $EC_{50}$ | 0.1 | 86% |
| hMC3r* | $EC_{50}$ | 0.02 | 109% |
| hMC4r | $EC_{50}$ | 0.07 | 88% |
| hMC4r* | $EC_{50}$ | 0.005 | 108% |
| hMC5r | $EC_{50}$ | 3 | 89% |
| hMC5r* | $EC_{50}$ | 10 | 70% |

-continued

| No. | Structure | Amino Acid Sequence and Functional Data |
|---|---|---|

78

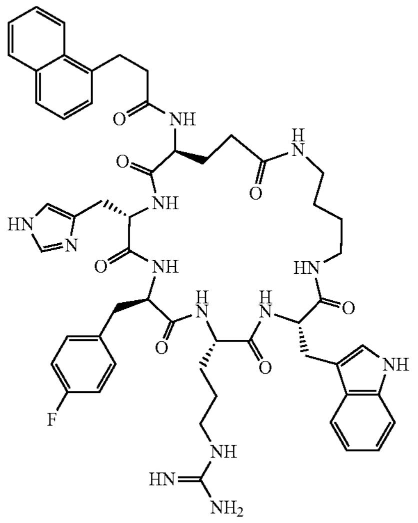 [SMILES: N=C(N)NCCC[C@@H]1NC(=O)[C@@H](Cc2ccc(F)cc2)NC(=O)[C@H](Cc2c[nH]cn2)NC(=O)[C@@H](NC(=O)CCc2cccc3ccccc23)CCC(=O)NCCCCNC(=O)[C@H](Cc2c[nH]c3ccccc23)NC1=O]

3-(1-Naphthyl)propanoyl-Glu-His-D-Phe(4-F)-Arg-Trp

NH———$(CH_2)_4$———NH

| Receptor | Assay | Value (nM) | % |
|---|---|---|---|
| hMC1r | $EC_{50}$ | 0.023 | 99% |
| hMC4r | $EC_{50}$ | 0.08 | 83% |
| hMC5r | $EC_{50}$ | 2 | 63% |

79

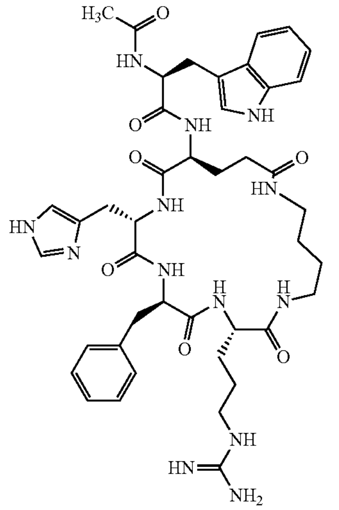 [SMILES: CC(=O)N[C@@H](Cc1c[nH]c2ccccc12)C(=O)N[C@H]1CCC(=O)NCCCCNC(=O)[C@H](CCCNC(=N)N)NC(=O)[C@@H](Cc2ccccc2)NC(=O)[C@H](Cc2c[nH]cn2)NC1=O]

Ac-Trp-Glu-His-D-Phe-Arg

NH—$(CH_2)_4$—NH

| Receptor | Assay | Value (nM) | % |
|---|---|---|---|
| hMC1r | $EC_{50}$ | 33 | 74% |
| hMC3r | $EC_{50}$ | NC | 45% |
| hMC4r | $EC_{50}$ | 1200 | 73% |
| hMC5r | $EC_{50}$ | NC | 4% |

80

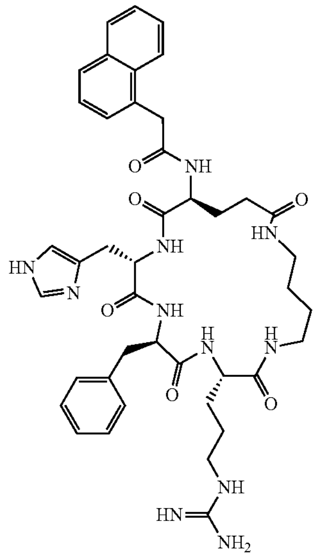 [SMILES: N=C(N)NCCC[C@@H]1NC(=O)[C@@H](Cc2ccccc2)NC(=O)[C@H](Cc2c[nH]cn2)NC(=O)[C@@H](NC(=O)Cc2cccc3ccccc23)CCC(=O)NCCCCNC1=O]

1-Naphthylacetyl-Glu-His-D-Phe-Arg

NH—$(CH_2)_4$—NH

| Receptor | Assay | Value (nM) | % |
|---|---|---|---|
| hMC1r | $EC_{50}$ | 45 | 65% |
| hMC3r | $EC_{50}$ | NC | 15% |
| hMC4r | $EC_{50}$ | NC | 21% |
| hMC5r | $EC_{50}$ | NC | 6% |

-continued

| No. | Structure | Amino Acid Sequence and Functional Data |
|---|---|---|
| 81 | 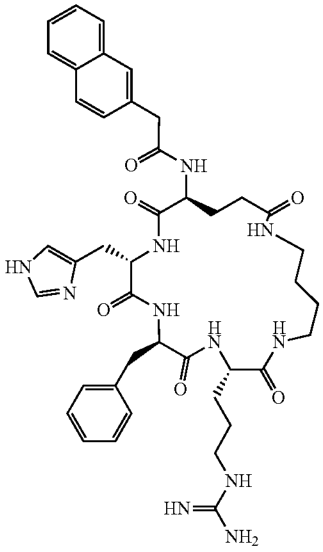 [SMILES: N=C(N)NCCC[C@@H]1NC(=O)[C@@H](Cc2ccccc2)NC(=O)[C@H](Cc2c[nH]cn2)NC(=O)[C@@H](NC(=O)Cc2ccc3ccccc3c2)CCC(=O)NCCCCNC1=O] | 2-Naphthylacetyl-Glu-His-D-Phe-Arg<br>NH—$(CH_2)_4$—NH |

| Receptor | Assay | Value (nM) | % |
|---|---|---|---|
| hMC1r | $EC_{50}$ | 5 | 88% |
| mMC1r | $EC_{50}$ | 395 | |
| 63% mMC1r* | $EC_{50}$ | 7150 | 48% |
| hMC3r | $EC_{50}$ | NC | 18% |
| hMC4r | $EC_{50}$ | 2025 | 40% |
| hMC5r | $EC_{50}$ | NC | 2% |

| No. | Structure | Amino Acid Sequence and Functional Data |
|---|---|---|
| 82 | 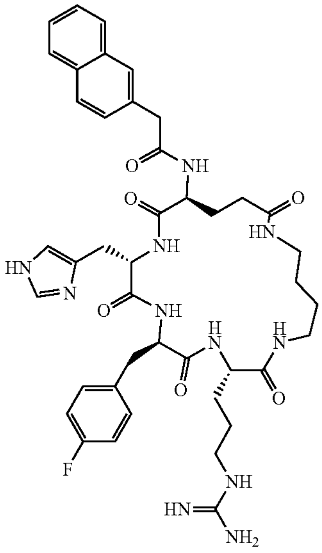 [SMILES: N=C(N)NCCC[C@@H]1NC(=O)[C@@H](Cc2ccc(F)cc2)NC(=O)[C@H](Cc2c[nH]cn2)NC(=O)[C@@H](NC(=O)Cc2ccc3ccccc3c2)CCC(=O)NCCCCNC1=O] | 2-Naphthylacetyl-Glu-His-D-Phe(4-F)-Arg<br>NH—$(CH_2)_4$—NH |

| Receptor | Assay | Value (nM) | % |
|---|---|---|---|
| hMC1r | $EC_{50}$ | 2 | 98% |
| mMC1r | $EC_{50}$ | 32 | 79% |
| mMC1r* | $EC_{50}$ | 660 | 71% |
| hMC3r | $EC_{50}$ | 210 | 66% |
| hMC4r | $EC_{50}$ | 108 | 83% |
| hMC5r | $EC_{50}$ | NC | 27% |

-continued

| No. | Structure | Amino Acid Sequence and Functional Data |
|---|---|---|
| 83 | 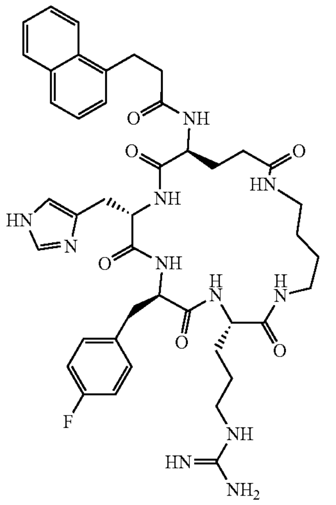 [SMILES: N=C(N)NCCC[C@@H]1NC(=O)[C@@H](Cc2ccc(F)cc2)NC(=O)[C@H](Cc2c[nH]cn2)NC(=O)[C@@H](NC(=O)CCc2cccc3ccccc23)CCC(=O)NCCCCNC1=O] | 3-(1-Naphthyl)propanoyl-Glu-His-D-Phe(4-F)-Arg<br>NH—$(CH_2)_4$—NH |

| Receptor | Assay | Value (nM) | % |
|---|---|---|---|
| hMC1r | $EC_{50}$ | 7 | 92% |
| hMC1r | $EC_{50}$ | 28 | 81% |
| hMC1r* | $EC_{50}$ | 130 | 61% |
| hMC3r | $EC_{50}$ | 470 | 65% |
| hMC4r | $EC_{50}$ | 178 | 97% |
| hMC5r | $EC_{50}$ | NC | 40% |

9.1.1 Peptides of the following structures are synthesized by the general methods described above, and $EC_{50}$ values for peptides are determined as disclosed above.

(SEQ ID NO: 75)

Ac-Nle-Glu-His-Xaa[1]-Arg-Trp
NH—$(CH_2)_4$—NH

Where Xaa[1] is:

D-Phe(4-Cl),
D-Phe(4-Me),
D-Phe(4-OMe),
D-Phe(4-Ph),
D-Phe(4-$NO_2$),
D-Phe(4CN),
D-Phe(3-Cl),
D-Phe(3-Me),
D-Phe(3-OMe),
D-Phe(3-Phe),
D-Phe(3-$NO_2$),
D-Phe(3-CN),
D-Phe(2,4-diF),
D-Phe(2,4-diMe),
D-Phe(3,5-diF),
D-Phe(3,4-diF),
D-Phe(3,4-diOMe),
D-Phe(2,4-diCl),
D-Phe(2-Cl,4F),
D-Nal 1,
D-Phe(2,3-diF),
D-Phe(2,3-diCl),
D-Phe(2,3-diMe), and
D-Phe(2,3-diOMe).

Following synthesis, the peptides are tested as described herein, and utilized in methods of preventing, ameliorating, or treating melanocortin receptor-mediated diseases, indications, conditions and syndromes.

9.2 Synthesis of Peptide No. 60

The peptide of Example 60 was synthesized for preclinical and clinical research utilizing standard solid-phase peptide chemistry to obtain a crude cyclic peptide intermediate. The resulting peptide intermediate was purified through a series of washing and preparative chromatography steps. Finally, the purified peptide was freeze-dried prior to final packaging and storage. The following process overview flow diagram shows the synthetic methodology for manufacture of the acetate salt of the peptide of Example 60:

Steps 1-6 Fmoc-Trp(Boc)-NH—$(CH_2)_4$—NH-2Cl-Trt-Resin

Complete Cycles, Adding Next Sequential Amino Acid in Each Cycle, Utilizing Fmoc-Arg(Pbf)-OH, Fmoc-Glu (OtBu)-OH, Fmoc-His(Trt)-OH, Fmoc-Nle-OH 1. Swell: DMF
2. De-Fmoc: Piperidine/DBU/HOBt/DMF
3. Wash Cycle: DMF, MBTE, DMF
4. Coupling Cycle: DCM/Fmoc-AA-OH/HOBt, DIPEA, DMF, HBTU
5. Wash Cycle: DMF, MBTE, DMF Step 7 Fmoc-Nle-Glu(OtBu)-His(Trt)-D-Phe(4-F)-Arg (Pbf)-Trp(Boc)-NH—$(CH_2)_4$—NH-2Cl-Trt-Resin (SEQ ID NO:76)

Acetylation of Resin-Bound Complete Peptide Sequence

1. De-Fmoc: Piperidine/DBU/HOBt/DMF
2. Wash Cycle: DMF, MBTE, DMF
3. N-terminal Acetylation: $Ac_2$—O/pyridine/DMF
4. Wash Cycle: DMF/MBTE
5. Dry: In vacuo, room temperature Step 8 Ac-Nle-Glu(OtBu)-His(Trt)-D-Phe(4-F)-Arg(Pbf)-Trp(Boc)-NH—$(CH_2)_4$—NH-2Cl-Trt-Resin (SEQ ID NO:77)

Global Cleavage and Deprotection

1. Cleavage: 95% TFA, 2.5% TIS, 2.5% $H_2O$
2. Precipitation: MTBE (0-5° C.)
3. Filtration and washes: MTBE
4. Dry: Vacuum at room temperature 5. Final washes & filtration: n-hexane
6. Dry: vacuum at room temperature Step 9 Ac-Nle-Glu-His-D-Phe(4-F)-Arg-Trp-NH—$(CH_2)_4$—NH·xTFA (x=1-3) (SEQ ID NO:78)

Peptide Cyclization

Dissolve: Linear peptide in THF/DMF and PyBOP
Cyclization: PyBOP, NMM and THF/DMF
Concentration: Rotary concentration
Trituration: EtOAc/MBTE
Dry: Vacuum at room temperature Step 10Ac-Nle-cyclo(Glu-His-D-Phe(4-F)-Arg-Trp-NH—$(CH_2)_4$—NH)·xTFA (x=1-2) (SEQ ID NO:79)

Ion Exchange and Product Elution

Dissolve and filter: Cyclic peptide in TFA/water/ACN, filter
Column loading: Load on C18 silica gel column
Elution: Gradient of TFA/water/ACN
Salt Exchange: 0.5 M ammonium acetate
Elution: AcOH, $H_2O$, ACN
Lyophilzation: Lyo flasks
FINAL Ac-Nle-cyclo(Glu-His-D-Phe(4-F)-Arg-Trp-NH—$(CH_2)_4$—NH)·xAcOH (x=1-2) (SEQ ID NO:80)

The peptide sequence was obtained using a condensation strategy where protected amino acids were linked to one after the other onto the solid support peptide resin. Coupling of the amino acids was done using a solid-phase peptide synthesis, where the next amino acid to be coupled to the peptide chain N-terminus is protected on its N-terminus and side chain using an Fmoc protecting group. The general SPPS procedure is one of repeated cycles of alternate N-terminal deprotection and coupling reactions, with resin washes between each step.

The coupling was monitored via use of an in-process Kaiser Test as well as a Chloranil/Toluene Test, which yields a negative result thereby indicating that the coupling reaction is complete. Once the reaction is complete, the liquid is drained from the reactor and the resin is dried.

One the complete peptide sequence was attached to resin and the N-terminal group acetylated, cleavage of the peptide resin was performed in a glass reactor under temperature-controlled conditions using a cocktail of TFA, 3,6-dioxa-1,8-octanedith (DODT), TIS, and water. After cleavage, the reaction mixture was filtered and washed with TFA. The peptide in the filtrate was precipitated using MTBE under temperature-controlled conditions and then filtered. Once the precipitated peptide was collected and triturated with n-hexane, the crude linear peptide was dried under vacuum.

The resulting linear peptide was cyclized, followed by peptide precipitation and drying under vacuum. Cyclization was carried out by treating the linear peptide with the coupling agent Benzotriazol-1-yloxy-tripyrrolidino-phosphonium hexafluorophosphate (PyBOP). This reaction was carried out in the presence of non-nucleophilic tertiary amine base such as N-methylmorpholine (NMM) in a coupling medium, preferably a mixture of Tetrahydrofuran (THF) and Dimethylformamide (DMF) at ambient temperature. The reaction was monitored by analytical RP HPLC testing. If the reaction was incomplete, additional aliquots of PyBOP and NMM were added to reaction mixture and the reaction continued for complete cyclization. Once the cyclization was complete, the reaction mixture was concentrated on a rotary evaporator. The concentrate was triturated with a mixture of ethyl acetate and MTBE, stirred and allowed to stand. The supernatant was decanted while the sediment is collected. The solidified product was then isolated by filtration or centrifugation. The obtained solid cyclic peptide was dried under vacuum.

Purification of the crude cyclic peptide was performed using a preparative reverse phase high performance chromatography (RP-HPLC) to obtain the final peptide product. The purification was conducted by the co-elution of peptide with TFA, water, and acetonitrile (ACN) buffer systems. The co-eluted fractions were analyzed for purity and impurity profile using in-process control HPLC method. Salt exchange transforms the purified peptide to acetate salt, utilizing acetic acid, acetonitrile, ammonium acetate, and water buffer solution. The purified peptide was filtered and the lyophilized utilizing a manifold lyophilizer to remove water and remaining residual organic solvents.

The resulting synthesized peptide had the chemical formula $C_{49}H_{67}FN_{14}O_8$ as the acetate salt ($CH_3COOH$ ($1 \leq x \leq 2$) where x is a single peptide molecule). The exact mass of the resulting peptide, without the acetate salt, is 998.43 Da, and the molecular weight is 999.16 Da.

9.3 Formulation of Peptide No. 60 for Ophthalmologic Use

Peptide No. 60 is formulation as an ophthalmologic solution drug product in blow-fill-seal dose containers for topical administration for diseases such as dry eye disease. Manufacturing is aseptic, with sterile filtration utilizing redundant 0.2 μm sterilizing grade polyethersulfone filters. The solution has a pH ~6.5 for topical ophthalmic administration. The drug product is supplied in single-use blow-fill-seal ampoules, which allow for product administration directly to the eye. Each ampoule contains a nominal volume of 0.25 mL. The secondary packaging is a foil pouch that contains three ampules in each pouch. The table below summarizes the formulation of the ophthalmologic solution drug product:

| Component | Concentration | Function |
|---|---|---|
| Peptide No. 60 | 1 μg/mL | Active Substance |
| Trisodium citrate, dihydrate | 2.79 mg/mL | Buffer |
| Citric acid, anhydrous | 0.10 mg/mL | Buffer |
| Sodium chloride | 9 mg/mL | Tonicity Agent |
| Polysorbate 80 (Tween) | 1 mg/mL | Surfactant |
| Sodium hydroxide | q.s. pH 6.5 | Adjust pH |
| Hydrochloric acid | q.s. pH 6.5 | Adjust pH |

9.4 Non-Clinical Study of Peptide No. 60 for Dry Eye Disease

To determine efficacy of peptide No. 60 for moderate, chronic dry-eye disease, male C57BL/6JRj mice were exposed to a controlled desiccating environment with transdermal administration of scopolamine (SiccaSystem™) to establish disease prior to any treatment. Corneal fluorescein staining was performed on study Days 10 and 12 (prior to treatment) and Day 24 (after 12 days of topical treatment with test compounds). Animals were randomized into 6 different experimental groups (n=12 for each treatment group, n=7 for untreated eyes) based on the fluorescein score on Day 12. Treatment arms included untreated and vehicle-treated animals and animals receiving Peptide No. 60 (3 different concentrations, $10^{-2}$, $10^{-3}$, and $10^{-4}$ mg/mL) or the reference compound cyclosporin ophthalmic emulsion, sold under the trade name Restasis®.

Figure 1B:
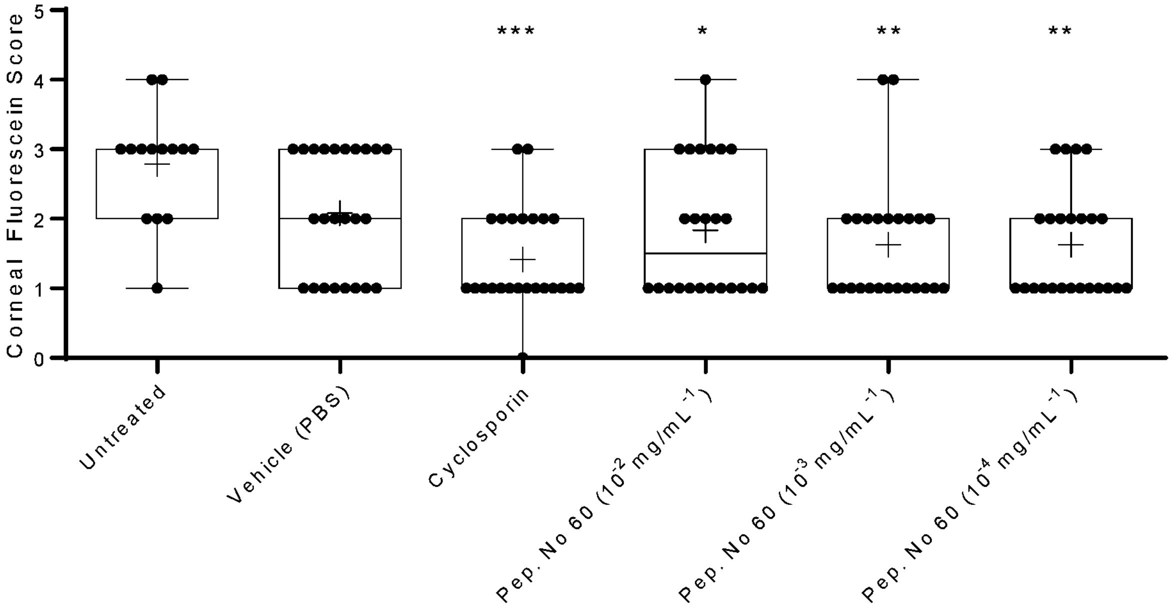
FIG. 1B is a box/whisker plot, indicating the median (line), 25th/75th percentile (box), mean (+) and the (whiskers) of the corneal fluorescein score on day 24, following treatment commencing on day 13 of the groups in FIG. 1A. Individual data points are depicted as filled circles. * $P<0.05$,  $P<0.01$, and * $P<0.001$ versus untreated eyes.

Non-parametric Kruskal-Wallis ANOVA showed no statistical significance between experimental groups on day 12 (P=0.84; FIG. 1A). On Day 24, corneal fluorescein scores were statistically significantly different between treatment groups (Kruskal-Wallis ANOVA, $P<0.001$; FIG. 1B). Restasis® ($P<0.001$) and Peptide No. 60 ($P<0.05$ for $10^{-2}$ mg/ml, $P<0.01$ for $10^{-3}$, and $10^{-4}$ mg/ml) showed statistically significant lower corneal fluorescein staining compared with untreated eyes (Dunn's multiple comparisons test; FIG. 1B).

Figure 2:
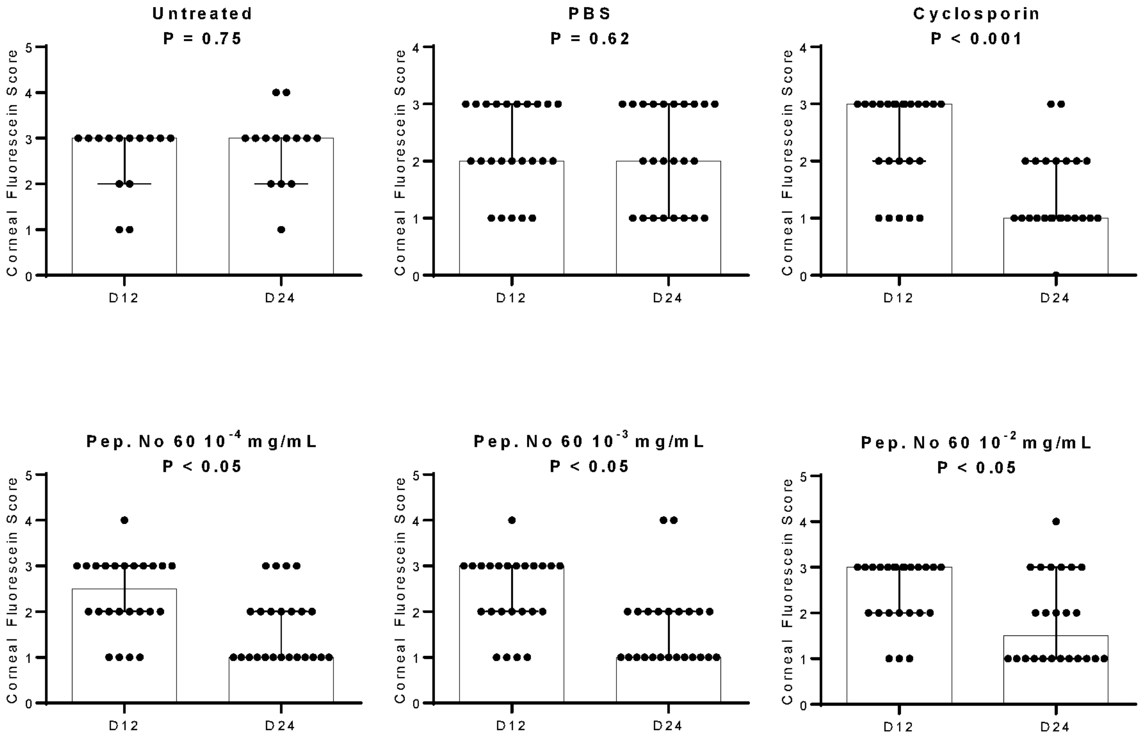
FIG. 2 are box/whisker plots of the data as in FIG. 1A and FIG. 1B, showing comparisons by treatment between day 12 (prior to treatment) and day 24 (after 12 days of topical treatment with test compounds) for untreated eyes, PBS (vehicle control phosphate buffered saline) and each test compound. Peptide No. 60 administered at doses between $10^{-2}$ and $10^{-4}$ mg/mL resulted in a statistically significantly improvement of corneal fluorescein scores from day 12 to day 24.

In addition, corneal fluorescein staining on Day 12 was compared with Day 24 for the same eye by treatment. Based on this analysis, fluorescein staining in untreated eyes remained similar between Day 12 and Day 24 (P=0.75). All experimental treatments (except Vehicle) resulted in a statistically significant improvement of corneal fluorescein staining (FIG. 2).

Peptide No. 60 administered at doses between $10^{-2}$ and $10^{-4}$ mg/mL resulted in a statistically significantly improvement of corneal fluorescein scores from Day 12 to Day 24.

9.5 Human Clinical Studies with Peptide No. 60

Peptide No. 60 was utilized in the ophthalmologic solution drug product of Example 9.3 in a multi-center, double-masked, randomized, placebo-controlled, parallel-arm, Phase 2 study, which enrolled approximately 160 subjects (80 subjects per treatment arm). The objective of this study was to compare the safety and efficacy of Peptide No. 60 to its vehicle from Day 1 (baseline) to Day 85 (Week 12) in adult subjects with mild, moderate or severe dry eye disease in a Controlled Adverse Environment (CAE) setting. Both signs and symptoms were assessed at periodic visits.

During the screening period, two 90-minute exposures to the CAE were conducted to ascertain eligibility to enter the study. Subjects who qualify were randomized to receive study drug or placebo in a double-masked fashion for 12 weeks. Subjects self-administered drops three times per day (TID) and completed daily diary assessments as instructed.

At Visits 3 (Day 15, Week 2), 4 (Day 29, Week 4), 5 (Day 57, Week 8), and 6 (Day 85, Week 12), subjects were exposed to a CAE, with pre-CAE, during CAE (symptoms only) and post-CAE assessments of ocular signs and symptoms.

Statistical significance for the primary endpoints, improvement in inferior corneal staining (sign) and ocular discomfort (symptom), was not reached in the overall enrolled population that included mild, moderate, and severe patients, as measured at the 12-week primary evaluation visit. Statistically significant improvement in multiple signs and symptoms was achieved in the moderate to severe patient population, after 2 weeks of dosing and at the 12-week visit. There were no safety signals identified and the Peptide No. 60 ophthalmologic solution drug product had excellent ocular tolerability.

In the sub-population of moderate to severe patients (N=61), the Peptide No. 60 ophthalmologic solution drug product achieved statistical significance (P value $<0.05$ vs. vehicle) at week 2 and week 12 for multiple signs, including inferior (the primary sign endpoint), superior, and total corneal staining, temporal, nasal and total conjunctival staining, and tear film break-up time, and multiple ocular symptoms, including ocular discomfort. Additionally, multiple signs and symptoms measures trended towards significance (P value $<0.1$ vs. vehicle).

Trial results demonstrated excellent safety and tolerability profile. There were no serious adverse events associated with study treatment observed. Three patients on placebo and one patient on Peptide No. 60 (not deemed to be drug related) discontinued from the study. There were no ocular, drug-related adverse events in the Peptide No. 60 subjects.

9.6 Peptide No. 60 Comparison to α-MSH

The potency ($EC_{50}$ values in nM) of Peptide No. 60 was compared to that of α-MSH. The profile showed a greater relative potency of Peptide No. 60 at MC1r and MC5r compared to α-MSH, with potency of Peptide No. 60 at MC3r and MC4r roughly comparable to that of α-MSH. Based upon animal model studies, the potency of Peptide No. 60 provides a superior receptor profile for dry eye and other ocular diseases, while providing for minimal side effects due to MC3r and MC4r. Additionally, the virtually identical $EC_{50}$ values at MC r and MC5r for Peptide No. 60 ensures simultaneous engagement with both MC1r and MC5r. By contrast, because of the $EC_{50}$ values of α-MSH and other prior art melanocortin receptor peptides and compounds are likely to engage MC1r and not MC5r at many concentration ranges. Utilizing a higher concentration of α-MSH and other prior art melanocortin receptor peptides and compounds to engage both MC1r and MC5r is likely to result in undesirable engagement with MC3r and MC4r. By contrast, because of the $EC_{50}$ values Peptide No. 60 will engage MC1r and MC5r at selected concentrations without engaging MC3r and MC4r, resulting in superior pharmacological response with minimal off-target effect.

| Receptor | α-MSH $EC_{50}$ (nM) | Peptide No. 60 $EC_{50}$ (nM) | Fold Peptide No. 60 More Potent Than α-MSH |
|---|---|---|---|
| MC1r (HBL) | 9.0 | 0.13 | 69X |
| MC1r (B16/F10) | 0.23 | 0.02 | 11X |
| MC3r | 3.0 | 0.77 | 3.9X |
| MC4r | 3.0 | 2.0 | 1.5X |
| MC5r | 103 | 0.15 | 686X |
| MC5r | 360 | 0.39 | 930X (CEREP) |

9.7 Peptide No. 60 Comparison to Bremelanotide

The potency ($EC_{50}$ values in nM) of Peptide No. 60 was compared to that of bremelanotide, a synthetic peptide of the sequence Ac-Nle-cyclo(Asp-His-D-Phe-Arg-Trp-Lys)-$NH_2$ (SEQ ID NO:81) as disclosed in U.S. Pat. No. 6,579,968, which was recently approved for treatment of hypoactive sexual desire disorder in premenopausal women. The profile showed approximately equal potency of Peptide No. 60 at MC1r compared to bremelanotide, but bremelanotide was devoid of MC5r activity. The role of MC5r in dry eye is important both for resolution of inflammation and also in tear architecture, given that the three glands which control secretions—meibomian (lipid), lacrimal (aqueous) and conjunctival/goblet cells (mucous)—express MC5r.

| Receptor | Bremelanotide $EC_{50}$ (nM) | Peptide No. 60 $EC_{50}$ (nM) | Fold Peptide No. 60 More Potent Than Bremelanotide |
|---|---|---|---|
| MC1r (HBL) | 0.10 | 0.13 | 0.78X |
| MC1r( B16/F10) | 0.10 | 0.02 | 5X |
| MC3r | 3.0 | 0.77 | 4X |
| MC4r | 1.0 | 2.0 | 0.5X |
| MC5r | 3360 | 0.15 | 22,500X |
| MC5r | >10,000 | 0.39 | >25,000X (CEREP) |

9.8 Peptide No. 60 Stability and Pharmacokinetics

Peptide No. 60 was evaluated in several stability and pharmacokinetic models. In a mouse model, Peptide No. 60 was found in both the conjunctiva and lacrimal gland at both 4 and 24 hours after dosing to the eye.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

SEQUENCE LISTING

```
Sequence total quantity: 82
SEQ ID NO: 1            moltype = AA  length = 6
FEATURE                 Location/Qualifiers
source                  1..6
                        mol_type = protein
                        organism = synthetic construct
SITE                    1
                        note = Norleucine
SITE                    4
                        note = D-4-fluoro phenylalanine
SITE                    2..6
                        note = Residues linked via 1,4-diaminobutane
SEQUENCE: 1
XEHFRW                                                              6

SEQ ID NO: 2            moltype = AA  length = 13
FEATURE                 Location/Qualifiers
source                  1..13
                        mol_type = protein
                        organism = synthetic construct
SITE                    13
                        note = Amidated residue
SEQUENCE: 2
SYSMEHFRWG KPV                                                      13

SEQ ID NO: 3            moltype = AA  length = 13
FEATURE                 Location/Qualifiers
source                  1..13
                        mol_type = protein
                        organism = synthetic construct
SITE                    4
                        note = Norleucine
SITE                    7
                        note = D-amino acid
SITE                    13
                        note = Amidated residue
SEQUENCE: 3
SYSXEHFRWG KPV                                                      13

SEQ ID NO: 4            moltype = AA  length = 6
FEATURE                 Location/Qualifiers
source                  1..6
                        mol_type = protein
                        organism = synthetic construct
SITE                    1
                        note = Norleucine
SITE                    2
                        note = 1-tert butyl ester modified residue
SITE                    3
                        note = Trityl modified residue
SITE                    4
                        note = D-4-fluoro phenylalanine
SITE                    5
                        note = Pentamethyldihydrobenzofuran-5-sulfonyl modified
                         residue
SITE                    6
                        note = t-butyloxycarbonyl modified residue
SEQUENCE: 4
XEHFRW                                                              6

SEQ ID NO: 5            moltype = AA  length = 6
FEATURE                 Location/Qualifiers
source                  1..6
                        mol_type = protein
                        organism = synthetic construct
SITE                    1
                        note = Norleucine
```

-continued

```
SITE                    4
                        note = D-4-fluoro phenylalanine
SEQUENCE: 5
XEHFRW                                                                     6

SEQ ID NO: 6            moltype = AA  length = 6
FEATURE                 Location/Qualifiers
source                  1..6
                        mol_type = protein
                        organism = synthetic construct
SITE                    3
                        note = O-benzyl-serine
SITE                    4
                        note = D-amino acid
SITE                    2..6
                        note = Residues linked via 1,5-diaminopentane
SEQUENCE: 6
RDSFRW                                                                     6

SEQ ID NO: 7            moltype = AA  length = 6
FEATURE                 Location/Qualifiers
source                  1..6
                        mol_type = protein
                        organism = synthetic construct
SITE                    1
                        note = Norleucine
SITE                    4
                        note = D-3-(1-naphthyl)alanine
SITE                    2..6
                        note = Residues linked via 1,5-diaminopentane
SEQUENCE: 7
XDHXRW                                                                     6

SEQ ID NO: 8            moltype = AA  length = 6
FEATURE                 Location/Qualifiers
source                  1..6
                        mol_type = protein
                        organism = synthetic construct
SITE                    1
                        note = Norleucine
SITE                    4
                        note = D-4-chloro phenylalanine
SITE                    2..6
                        note = Residues linked via 1,5-diaminopentane
SEQUENCE: 8
XDHFRW                                                                     6

SEQ ID NO: 9            moltype = AA  length = 6
FEATURE                 Location/Qualifiers
source                  1..6
                        mol_type = protein
                        organism = synthetic construct
SITE                    1
                        note = Norleucine
SITE                    4
                        note = D-3,4-chloro phenylalanine
SITE                    2..6
                        note = Residues linked via 1,5-diaminopentane
SEQUENCE: 9
XDHFRW                                                                     6

SEQ ID NO: 10           moltype = AA  length = 6
FEATURE                 Location/Qualifiers
source                  1..6
                        mol_type = protein
                        organism = synthetic construct
SITE                    1
                        note = Norleucine
SITE                    3
                        note = Methionine sulfone
SITE                    4
                        note = D-3-(1-naphthyl)alanine
SITE                    2..6
                        note = Residues linked via 1,5-diaminopentane
SEQUENCE: 10
XDMXRW                                                                     6

SEQ ID NO: 11           moltype = AA  length = 5
FEATURE                 Location/Qualifiers
```

-continued

```
source                 1..5
                       mol_type = protein
                       organism = synthetic construct
SITE                   3
                       note = D-3-(1-naphthyl)alanine
SITE                   1..5
                       note = Residues linked via 1,5-diaminopentane
SEQUENCE: 11
DHXRW                                                              5

SEQ ID NO: 12          moltype = AA  length = 5
FEATURE                Location/Qualifiers
source                 1..5
                       mol_type = protein
                       organism = synthetic construct
SITE                   3
                       note = D-3-(1-naphthyl)alanine
SITE                   1..5
                       note = Residues linked via 1,5-diaminopentane
SEQUENCE: 12
DHXRW                                                              5

SEQ ID NO: 13          moltype = AA  length = 6
FEATURE                Location/Qualifiers
source                 1..6
                       mol_type = protein
                       organism = synthetic construct
SITE                   1
                       note = Norleucine
SITE                   3
                       note = O-benzyl-hydroxyproline
SITE                   4
                       note = D-amino acid
SITE                   2..6
                       note = Residues linked via 1,5-diaminopentane
SEQUENCE: 13
XDXFRW                                                             6

SEQ ID NO: 14          moltype = AA  length = 6
FEATURE                Location/Qualifiers
source                 1..6
                       mol_type = protein
                       organism = synthetic construct
SITE                   4
                       note = D-amino acid
SITE                   2..6
                       note = Residues linked via 1,4-diaminobutane
SEQUENCE: 14
REHFRW                                                             6

SEQ ID NO: 15          moltype = AA  length = 6
FEATURE                Location/Qualifiers
source                 1..6
                       mol_type = protein
                       organism = synthetic construct
SITE                   4
                       note = D-amino acid
SITE                   2..6
                       note = Residues linked via 1,4-diaminobutane
SEQUENCE: 15
RENFRW                                                             6

SEQ ID NO: 16          moltype = AA  length = 6
FEATURE                Location/Qualifiers
source                 1..6
                       mol_type = protein
                       organism = synthetic construct
SITE                   4
                       note = D-amino acid
SITE                   2..6
                       note = Residues linked via 1,5-diaminopentane
SEQUENCE: 16
RDHFRW                                                             6

SEQ ID NO: 17          moltype = AA  length = 6
FEATURE                Location/Qualifiers
source                 1..6
                       mol_type = protein
                       organism = synthetic construct
```

-continued

```
SITE                    4
                        note = D-amino acid
SITE                    2..6
                        note = Residues linked via 1,5-diaminopentane
SEQUENCE: 17
RDNFRW                                                                    6

SEQ ID NO: 18           moltype = AA  length = 6
FEATURE                 Location/Qualifiers
source                  1..6
                        mol_type = protein
                        organism = synthetic construct
SITE                    4
                        note = D-amino acid
SITE                    2..6
                        note = Residues linked via 2-aminoethylether
SEQUENCE: 18
RDHFRW                                                                    6

SEQ ID NO: 19           moltype = AA  length = 6
FEATURE                 Location/Qualifiers
source                  1..6
                        mol_type = protein
                        organism = synthetic construct
SITE                    4
                        note = D-amino acid
SITE                    2..6
                        note = Residues linked via 2-aminoethylether
SEQUENCE: 19
RDNFRW                                                                    6

SEQ ID NO: 20           moltype = AA  length = 6
FEATURE                 Location/Qualifiers
source                  1..6
                        mol_type = protein
                        organism = synthetic construct
SITE                    4
                        note = D-3-(2-naphthyl)alanine
SITE                    2..6
                        note = Residues linked via 1,4-diaminobutane
SEQUENCE: 20
REHXRW                                                                    6

SEQ ID NO: 21           moltype = AA  length = 6
FEATURE                 Location/Qualifiers
source                  1..6
                        mol_type = protein
                        organism = synthetic construct
SITE                    4
                        note = D-3-(2-naphthyl)alanine
SITE                    6
                        note = D-amino acid
SITE                    2..6
                        note = Residues linked via 1,4-diaminobutane
SEQUENCE: 21
REHXRW                                                                    6

SEQ ID NO: 22           moltype = AA  length = 6
FEATURE                 Location/Qualifiers
source                  1..6
                        mol_type = protein
                        organism = synthetic construct
SITE                    1
                        note = Norleucine
SITE                    4
                        note = D-3-(2-naphthyl)alanine
SITE                    6
                        note = D-amino acid
SITE                    2..6
                        note = Residues linked via 1,4-diaminobutane
SEQUENCE: 22
XEHXRW                                                                    6

SEQ ID NO: 23           moltype = AA  length = 6
FEATURE                 Location/Qualifiers
source                  1..6
                        mol_type = protein
                        organism = synthetic construct
SITE                    1
```

-continued

```
                        note = D-amino acid
SITE                    4
                        note = D-3-(2-naphthyl)alanine
SITE                    6
                        note = D-amino acid
SITE                    2..6
                        note = Residues linked via 1,4-diaminobutane
SEQUENCE: 23
REHXRW                                                                  6

SEQ ID NO: 24           moltype = AA  length = 6
FEATURE                 Location/Qualifiers
source                  1..6
                        mol_type = protein
                        organism = synthetic construct
SITE                    1
                        note = D-Norleucine
SITE                    4
                        note = D-3-(2-naphthyl)alanine
SITE                    6
                        note = D-amino acid
SITE                    2..6
                        note = Residues linked via 1,4-diaminobutane
SEQUENCE: 24
XEHXRW                                                                  6

SEQ ID NO: 25           moltype = AA  length = 6
FEATURE                 Location/Qualifiers
source                  1..6
                        mol_type = protein
                        organism = synthetic construct
SITE                    4
                        note = D-3-(2-naphthyl)alanine
SITE                    6
                        note = D-amino acid
SITE                    2..6
                        note = Residues linked via 1,2-diaminoethane
SEQUENCE: 25
REHXRW                                                                  6

SEQ ID NO: 26           moltype = AA  length = 6
FEATURE                 Location/Qualifiers
source                  1..6
                        mol_type = protein
                        organism = synthetic construct
SITE                    1
                        note = D-amino acid
SITE                    4
                        note = D-3-(2-naphthyl)alanine
SITE                    6
                        note = D-amino acid
SITE                    2..6
                        note = Residues linked via 1,2-diaminoethane
SEQUENCE: 26
REHXRW                                                                  6

SEQ ID NO: 27           moltype = AA  length = 6
FEATURE                 Location/Qualifiers
source                  1..6
                        mol_type = protein
                        organism = synthetic construct
SITE                    1
                        note = Norleucine
SITE                    4
                        note = D-3-(2-naphthyl)alanine
SITE                    6
                        note = D-amino acid
SITE                    2..6
                        note = Residues linked via 1,2-diaminoethane
SEQUENCE: 27
XEHXRW                                                                  6

SEQ ID NO: 28           moltype = AA  length = 6
FEATURE                 Location/Qualifiers
source                  1..6
                        mol_type = protein
                        organism = synthetic construct
SITE                    1
                        note = D-Norleucine
```

-continued

```
SITE                    4
                        note = D-3-(2-naphthyl)alanine
SITE                    6
                        note = D-amino acid
SITE                    2..6
                        note = Residues linked via 1,2-diaminoethane
SEQUENCE: 28
XEHXRW                                                                      6

SEQ ID NO: 29           moltype = AA  length = 6
FEATURE                 Location/Qualifiers
source                  1..6
                        mol_type = protein
                        organism = synthetic construct
SITE                    1
                        note = D-Norleucine
SITE                    4
                        note = D-3-(2-naphthyl)alanine
SITE                    2..6
                        note = Residues linked via 1,2-diaminoethane
SEQUENCE: 29
XEHXRW                                                                      6

SEQ ID NO: 30           moltype = AA  length = 6
FEATURE                 Location/Qualifiers
source                  1..6
                        mol_type = protein
                        organism = synthetic construct
SITE                    1
                        note = D-amino acid
SITE                    4
                        note = D-3-(2-naphthyl)alanine
SITE                    2..6
                        note = Residues linked via 1,2-diaminoethane
SEQUENCE: 30
REHXRW                                                                      6

SEQ ID NO: 31           moltype = AA  length = 6
FEATURE                 Location/Qualifiers
source                  1..6
                        mol_type = protein
                        organism = synthetic construct
SITE                    4
                        note = D-3-(2-naphthyl)alanine
SITE                    2..6
                        note = Residues linked via 1,2-diaminoethane
SEQUENCE: 31
REHXRW                                                                      6

SEQ ID NO: 32           moltype = AA  length = 6
FEATURE                 Location/Qualifiers
source                  1..6
                        mol_type = protein
                        organism = synthetic construct
SITE                    4
                        note = D-3-(2-naphthyl)alanine
SITE                    2..6
                        note = Residues linked via 1,3-diaminopropane
SEQUENCE: 32
REHXRW                                                                      6

SEQ ID NO: 33           moltype = AA  length = 6
FEATURE                 Location/Qualifiers
source                  1..6
                        mol_type = protein
                        organism = synthetic construct
SITE                    1
                        note = D-amino acid
SITE                    4
                        note = D-3-(2-naphthyl)alanine
SITE                    2..6
                        note = Residues linked via 1,3-diaminopropane
SEQUENCE: 33
REHXRW                                                                      6

SEQ ID NO: 34           moltype = AA  length = 6
FEATURE                 Location/Qualifiers
source                  1..6
                        mol_type = protein
```

-continued

```
                        organism = synthetic construct
SITE                    1
                        note = Norleucine
SITE                    4
                        note = D-3-(2-naphthyl)alanine
SITE                    6
                        note = D-amino acid
SITE                    2..6
                        note = Residues linked via 1,3-diaminopropane
SEQUENCE: 34
XEHXRW                                                                    6

SEQ ID NO: 35           moltype = AA  length = 6
FEATURE                 Location/Qualifiers
source                  1..6
                        mol_type = protein
                        organism = synthetic construct
SITE                    1
                        note = D-amino acid
SITE                    4
                        note = D-3-(2-naphthyl)alanine
SITE                    2..6
                        note = Residues linked via 1,4-diaminobutane
SEQUENCE: 35
REHXRW                                                                    6

SEQ ID NO: 36           moltype = AA  length = 6
FEATURE                 Location/Qualifiers
source                  1..6
                        mol_type = protein
                        organism = synthetic construct
SITE                    1
                        note = Norleucine
SITE                    4
                        note = D-3-(2-naphthyl)alanine
SITE                    2..6
                        note = Residues linked via 1,4-diaminobutane
SEQUENCE: 36
XEHXRW                                                                    6

SEQ ID NO: 37           moltype = AA  length = 6
FEATURE                 Location/Qualifiers
source                  1..6
                        mol_type = protein
                        organism = synthetic construct
SITE                    1
                        note = D-Norleucine
SITE                    4
                        note = D-3-(2-naphthyl)alanine
SITE                    2..6
                        note = Residues linked via 1,4-diaminobutane
SEQUENCE: 37
XEHXRW                                                                    6

SEQ ID NO: 38           moltype = AA  length = 6
FEATURE                 Location/Qualifiers
source                  1..6
                        mol_type = protein
                        organism = synthetic construct
SITE                    1
                        note = D-Norleucine
SITE                    3
                        note = Methionine sulfone
SITE                    4
                        note = D-3-(1-naphthyl)alanine
SITE                    2..6
                        note = Residues linked via 1,4-diaminobutane
SEQUENCE: 38
XEMXRW                                                                    6

SEQ ID NO: 39           moltype = AA  length = 6
FEATURE                 Location/Qualifiers
source                  1..6
                        mol_type = protein
                        organism = synthetic construct
SITE                    1
                        note = Norleucine
SITE                    4
                        note = D-3-(1-naphthyl)alanine
```

```
SITE                    2..6
                        note = Residues linked via 1,4-diaminobutane
SEQUENCE: 39
XENXRW                                                                     6

SEQ ID NO: 40           moltype = AA  length = 6
FEATURE                 Location/Qualifiers
source                  1..6
                        mol_type = protein
                        organism = synthetic construct
SITE                    1
                        note = Norleucine
SITE                    4
                        note = D-3-(2-naphthyl)alanine
SITE                    2..6
                        note = Residues linked via 1,4-diaminobutane
SEQUENCE: 40
XEHXRW                                                                     6

SEQ ID NO: 41           moltype = AA  length = 6
FEATURE                 Location/Qualifiers
source                  1..6
                        mol_type = protein
                        organism = synthetic construct
SITE                    1
                        note = Norleucine
SITE                    4
                        note = D-3-chloro phenylalanine
SITE                    2..6
                        note = Residues linked via 1,4-diaminobutane
SEQUENCE: 41
XEHFRW                                                                     6

SEQ ID NO: 42           moltype = AA  length = 6
FEATURE                 Location/Qualifiers
source                  1..6
                        mol_type = protein
                        organism = synthetic construct
SITE                    1
                        note = Norleucine
SITE                    4
                        note = D-2-fluoro phenylalanine
SITE                    2..6
                        note = Residues linked via 1,4-diaminobutane
SEQUENCE: 42
XEHFRW                                                                     6

SEQ ID NO: 43           moltype = AA  length = 6
FEATURE                 Location/Qualifiers
source                  1..6
                        mol_type = protein
                        organism = synthetic construct
SITE                    1
                        note = D-Norleucine
SITE                    3
                        note = Methionine sulfone
SITE                    4
                        note = D-3-(1-naphthyl)alanine
SITE                    2..6
                        note = Residues linked via 1,5-diaminopentane
SEQUENCE: 43
XEMXRW                                                                     6

SEQ ID NO: 44           moltype = AA  length = 6
FEATURE                 Location/Qualifiers
source                  1..6
                        mol_type = protein
                        organism = synthetic construct
SITE                    1
                        note = D-Norleucine
SITE                    3
                        note = Methionine sulfone
SITE                    4
                        note = D-3-(1-naphthyl)alanine
SITE                    2..6
                        note = Residues linked via 1,5-diaminopentane
SEQUENCE: 44
XDMXRW                                                                     6
```

-continued

```
SEQ ID NO: 45           moltype = AA  length = 6
FEATURE                 Location/Qualifiers
source                  1..6
                        mol_type = protein
                        organism = synthetic construct
SITE                    1
                        note = Norleucine
SITE                    3
                        note = Methionine sulfone
SITE                    4
                        note = D-3-(1-naphthyl)alanine
SITE                    2..6
                        note = Residues linked via 1,4-diaminobutane
SEQUENCE: 45
XDMXRW                                                                    6

SEQ ID NO: 46           moltype = AA  length = 6
FEATURE                 Location/Qualifiers
source                  1..6
                        mol_type = protein
                        organism = synthetic construct
SITE                    1
                        note = Norleucine
SITE                    4
                        note = D-2-chloro phenylalanine
SITE                    2..6
                        note = Residues linked via 1,4-diaminobutane
SEQUENCE: 46
XEHFRW                                                                    6

SEQ ID NO: 47           moltype = AA  length = 6
FEATURE                 Location/Qualifiers
source                  1..6
                        mol_type = protein
                        organism = synthetic construct
SITE                    1
                        note = Norleucine
SITE                    4
                        note = D-2-bromo phenylalanine
SITE                    2..6
                        note = Residues linked via 1,4-diaminobutane
SEQUENCE: 47
XEHFRW                                                                    6

SEQ ID NO: 48           moltype = AA  length = 6
FEATURE                 Location/Qualifiers
source                  1..6
                        mol_type = protein
                        organism = synthetic construct
SITE                    1
                        note = Norleucine
SITE                    4
                        note = D-2-methyl phenylalanine
SITE                    2..6
                        note = Residues linked via 1,4-diaminobutane
SEQUENCE: 48
XEHFRW                                                                    6

SEQ ID NO: 49           moltype = AA  length = 6
FEATURE                 Location/Qualifiers
source                  1..6
                        mol_type = protein
                        organism = synthetic construct
SITE                    1
                        note = Norleucine
SITE                    4
                        note = D-2-cyano phenylalanine
SITE                    2..6
                        note = Residues linked via 1,4-diaminobutane
SEQUENCE: 49
XEHFRW                                                                    6

SEQ ID NO: 50           moltype = AA  length = 6
FEATURE                 Location/Qualifiers
source                  1..6
                        mol_type = protein
                        organism = synthetic construct
SITE                    1
                        note = Norleucine
```

-continued

```
SITE                  4
                      note = D-2-trifluoromethyl phenylalanine
SITE                  2..6
                      note = Residues linked via 1,4-diaminobutane
SEQUENCE: 50
XEHFRW                                                                 6

SEQ ID NO: 51         moltype = AA  length = 6
FEATURE               Location/Qualifiers
source                1..6
                      mol_type = protein
                      organism = synthetic construct
SITE                  1
                      note = Norleucine
SITE                  4
                      note = D-4-fluoro phenylalanine
SITE                  2..6
                      note = Residues linked via 1,4-diaminobutane
SEQUENCE: 51
XEHFRW                                                                 6

SEQ ID NO: 52         moltype = AA  length = 6
FEATURE               Location/Qualifiers
source                1..6
                      mol_type = protein
                      organism = synthetic construct
SITE                  1
                      note = Norleucine
SITE                  4
                      note = D-2-nitro phenylalanine
SITE                  2..6
                      note = Residues linked via 1,4-diaminobutane
SEQUENCE: 52
XEHFRW                                                                 6

SEQ ID NO: 53         moltype = AA  length = 4
FEATURE               Location/Qualifiers
source                1..4
                      mol_type = protein
                      organism = synthetic construct
SITE                  3
                      note = D-amino acid
SITE                  1..4
                      note = Residues linked via 1,2-diaminoethane
SEQUENCE: 53
EHFR                                                                   4

SEQ ID NO: 54         moltype = AA  length = 4
FEATURE               Location/Qualifiers
source                1..4
                      mol_type = protein
                      organism = synthetic construct
SITE                  3
                      note = D-amino acid
SITE                  1..4
                      note = Residues linked via 1,4-diaminobutane
SEQUENCE: 54
EHFR                                                                   4

SEQ ID NO: 55         moltype = AA  length = 4
FEATURE               Location/Qualifiers
source                1..4
                      mol_type = protein
                      organism = synthetic construct
SITE                  3
                      note = D-amino acid
SITE                  1..4
                      note = Residues linked via 1,4-diaminobutane
SEQUENCE: 55
EHFR                                                                   4

SEQ ID NO: 56         moltype = AA  length = 4
FEATURE               Location/Qualifiers
source                1..4
                      mol_type = protein
                      organism = synthetic construct
SITE                  3
                      note = D-amino acid
SITE                  1..4
```

```
                        note = Residues linked via 1,4-diaminobutane
SEQUENCE: 56
EHFR                                                                  4

SEQ ID NO: 57           moltype = AA  length = 5
FEATURE                 Location/Qualifiers
source                  1..5
                        mol_type = protein
                        organism = synthetic construct
SITE                    3
                        note = D-amino acid
SITE                    1..5
                        note = Residues linked via 1,4-diaminobutane
SEQUENCE: 57
EHFRW                                                                 5

SEQ ID NO: 58           moltype = AA  length = 4
FEATURE                 Location/Qualifiers
source                  1..4
                        mol_type = protein
                        organism = synthetic construct
SITE                    3
                        note = D-amino acid
SITE                    1..4
                        note = Residues linked via 1,4-diaminobutane
SEQUENCE: 58
EHFR                                                                  4

SEQ ID NO: 59           moltype = AA  length = 4
FEATURE                 Location/Qualifiers
source                  1..4
                        mol_type = protein
                        organism = synthetic construct
SITE                    3
                        note = D-amino acid
SITE                    1..4
                        note = Residues linked via 1,2-diaminoethane
SEQUENCE: 59
EHFR                                                                  4

SEQ ID NO: 60           moltype = AA  length = 4
FEATURE                 Location/Qualifiers
source                  1..4
                        mol_type = protein
                        organism = synthetic construct
SITE                    3
                        note = D-amino acid
SITE                    1..4
                        note = Residues linked via 1,2-diaminoethane
SEQUENCE: 60
EHFR                                                                  4

SEQ ID NO: 61           moltype = AA  length = 4
FEATURE                 Location/Qualifiers
source                  1..4
                        mol_type = protein
                        organism = synthetic construct
SITE                    3
                        note = D-amino acid
SITE                    1..4
                        note = Residues linked via 1,2-diaminoethane
SEQUENCE: 61
EHFR                                                                  4

SEQ ID NO: 62           moltype = AA  length = 5
FEATURE                 Location/Qualifiers
source                  1..5
                        mol_type = protein
                        organism = synthetic construct
SITE                    3
                        note = D-4-fluoro phenylalanine
SITE                    1..5
                        note = Residues linked via 1,4-diaminobutane
SEQUENCE: 62
EHFRW                                                                 5

SEQ ID NO: 63           moltype = AA  length = 5
FEATURE                 Location/Qualifiers
source                  1..5
```

-continued

```
                          mol_type = protein
                          organism = synthetic construct
SITE                      3
                          note = D-4-fluoro phenylalanine
SITE                      1..5
                          note = Residues linked via 1,4-diaminobutane
SEQUENCE: 63
EHFRW                                                                        5

SEQ ID NO: 64             moltype = AA  length = 5
FEATURE                   Location/Qualifiers
source                    1..5
                          mol_type = protein
                          organism = synthetic construct
SITE                      3
                          note = D-4-fluoro phenylalanine
SITE                      1..5
                          note = Residues linked via 1,4-diaminobutane
SEQUENCE: 64
EHFRW                                                                        5

SEQ ID NO: 65             moltype = AA  length = 5
FEATURE                   Location/Qualifiers
source                    1..5
                          mol_type = protein
                          organism = synthetic construct
SITE                      3
                          note = D-4-fluoro phenylalanine
SITE                      1..5
                          note = Residues linked via 1,4-diaminobutane
SEQUENCE: 65
EHFRW                                                                        5

SEQ ID NO: 66             moltype = AA  length = 5
FEATURE                   Location/Qualifiers
source                    1..5
                          mol_type = protein
                          organism = synthetic construct
SITE                      3
                          note = D-4-fluoro phenylalanine
SITE                      1..5
                          note = Residues linked via 1,4-diaminobutane
SEQUENCE: 66
EHFRW                                                                        5

SEQ ID NO: 67             moltype = AA  length = 5
FEATURE                   Location/Qualifiers
source                    1..5
                          mol_type = protein
                          organism = synthetic construct
SITE                      4
                          note = D-amino acid
SITE                      2..5
                          note = Residues linked via 1,4-diaminobutane
SEQUENCE: 67
WEHFR                                                                        5

SEQ ID NO: 68             moltype = AA  length = 5
FEATURE                   Location/Qualifiers
source                    1..5
                          mol_type = protein
                          organism = synthetic construct
SITE                      3
                          note = D-4-fluoro phenylalanine
SITE                      1..5
                          note = Residues linked via 1,4-diaminobutane
SEQUENCE: 68
EHFRW                                                                        5

SEQ ID NO: 69             moltype = AA  length = 5
FEATURE                   Location/Qualifiers
source                    1..5
                          mol_type = protein
                          organism = synthetic construct
SITE                      3
                          note = D-4-fluoro phenylalanine
SITE                      1..5
                          note = Residues linked via 1,4-diaminobutane
SEQUENCE: 69
```

-continued

```
EHFRW                                                               5

SEQ ID NO: 70          moltype = AA  length = 5
FEATURE                Location/Qualifiers
source                 1..5
                       mol_type = protein
                       organism = synthetic construct
SITE                   4
                       note = D-amino acid
SITE                   2..5
                       note = Residues linked via 1,4-diaminobutane
SEQUENCE: 70
WEHFR                                                               5

SEQ ID NO: 71          moltype = AA  length = 4
FEATURE                Location/Qualifiers
source                 1..4
                       mol_type = protein
                       organism = synthetic construct
SITE                   3
                       note = D-amino acid
SITE                   1..4
                       note = Residues linked via 1,4-diaminobutane
SEQUENCE: 71
EHFR                                                                4

SEQ ID NO: 72          moltype = AA  length = 4
FEATURE                Location/Qualifiers
source                 1..4
                       mol_type = protein
                       organism = synthetic construct
SITE                   3
                       note = D-amino acid
SITE                   1..4
                       note = Residues linked via 1,4-diaminobutane
SEQUENCE: 72
EHFR                                                                4

SEQ ID NO: 73          moltype = AA  length = 4
FEATURE                Location/Qualifiers
source                 1..4
                       mol_type = protein
                       organism = synthetic construct
SITE                   3
                       note = D-4-fluoro phenylalanine
SITE                   1..4
                       note = Residues linked via 1,4-diaminobutane
SEQUENCE: 73
EHFR                                                                4

SEQ ID NO: 74          moltype = AA  length = 4
FEATURE                Location/Qualifiers
source                 1..4
                       mol_type = protein
                       organism = synthetic construct
SITE                   3
                       note = D-4-fluoro phenylalanine
SITE                   1..4
                       note = Residues linked via 1,4-diaminobutane
SEQUENCE: 74
EHFR                                                                4

SEQ ID NO: 75          moltype = AA  length = 6
FEATURE                Location/Qualifiers
source                 1..6
                       mol_type = protein
                       organism = synthetic construct
SITE                   1
                       note = Norleucine
VARIANT                4
                       note = D-4-chloro phenylalanine, D-4-methyl phenylalanine,
                        D-4-methoxy phenylalanine, D-4-phenyl phenylalanine,
                        D-4-nitro phenylalanine, D-4-cyano phenylalanine,
                        D-3-chloro phenylalanine, D-3-methyl phenylalanine,
                        D-3-methoxy phenylalanine, D-3-phenyl phenylalanine,
                        D-3-nitro phenylalanine, D-3-cyano phenylalanine,
                        D-2,4-difluoro phenylalanine, D-2,4-dimethyl
                        phenylalanine, D-3,5-difluoro phenylalanine,
                        D-3,4-difluoro phenylalanine, D-3,4-dimethoxy
```

-continued

```
                         phenylalanine, D-2,4-dichloro phenylalanine,
                         D-2-chloro,4-fluoro phenylalanine,
                         D-3-(1-naphthyl)alanine, D-2,3-difluoro phenylalanine,
                         D-2,3-dichloro phenylalanine, D-2,3-dimethyl
                         phenylalanine, or D-2,3-dimethoxy phenylalanine
SITE                    2..6
                        note = Residues linked via 1,4-diaminobutane
SEQUENCE: 75
XEHXRW                                                                        6

SEQ ID NO: 76           moltype = AA  length = 6
FEATURE                 Location/Qualifiers
source                  1..6
                        mol_type = protein
                        organism = synthetic construct
SITE                    1
                        note = Norleucine
SITE                    2
                        note = 1-tert butyl ester modified residue
SITE                    3
                        note = Trityl modified residue
SITE                    4
                        note = D-4-fluoro phenylalanine
SITE                    5
                        note = Pentamethyldihydrobenzofuran-5-sulfonyl modified
                         residue
SITE                    6
                        note = t-butyloxycarbonyl modified residue
SEQUENCE: 76
XEHFRW                                                                        6

SEQ ID NO: 77           moltype = AA  length = 6
FEATURE                 Location/Qualifiers
source                  1..6
                        mol_type = protein
                        organism = synthetic construct
SITE                    1
                        note = Norleucine
SITE                    2
                        note = 1-tert butyl ester modified residue
SITE                    3
                        note = Trityl modified residue
SITE                    4
                        note = D-4-fluoro phenylalanine
SITE                    5
                        note = Pentamethyldihydrobenzofuran-5-sulfonyl modified
                         residue
SITE                    6
                        note = t-butyloxycarbonyl modified residue
SEQUENCE: 77
XEHFRW                                                                        6

SEQ ID NO: 78           moltype = AA  length = 6
FEATURE                 Location/Qualifiers
source                  1..6
                        mol_type = protein
                        organism = synthetic construct
SITE                    1
                        note = Norleucine
SITE                    4
                        note = D-4-fluoro phenylalanine
SEQUENCE: 78
XEHFRW                                                                        6

SEQ ID NO: 79           moltype = AA  length = 6
FEATURE                 Location/Qualifiers
source                  1..6
                        mol_type = protein
                        organism = synthetic construct
SITE                    1
                        note = Norleucine
SITE                    4
                        note = D-4-fluoro phenylalanine
SITE                    2..6
                        note = Residues linked via 1,4-diaminobutane
SEQUENCE: 79
XEHFRW                                                                        6

SEQ ID NO: 80           moltype = AA  length = 6
```

-continued

```
FEATURE              Location/Qualifiers
source               1..6
                     mol_type = protein
                     organism = synthetic construct
SITE                 1
                     note = Norleucine
SITE                 4
                     note = D-4-fluoro phenylalanine
SITE                 2..6
                     note = Residues linked via 1,4-diaminobutane
SEQUENCE: 80
XEHFRW                                                          6

SEQ ID NO: 81        moltype = AA  length = 7
FEATURE              Location/Qualifiers
source               1..7
                     mol_type = protein
                     organism = synthetic construct
SITE                 1
                     note = Norleucine
SITE                 4
                     note = D-amino acid
SITE                 7
                     note = Amidated residue
SITE                 2..7
                     note = Residues linked via the side chain
SEQUENCE: 81
XDHFRWK                                                         7

SEQ ID NO: 82        moltype = AA  length = 4
FEATURE              Location/Qualifiers
source               1..4
                     mol_type = protein
                     organism = synthetic construct
SEQUENCE: 82
HFRW                                                            4
```

We claim:

1. A cyclic peptide having the structure (SEQ ID NO: 51)

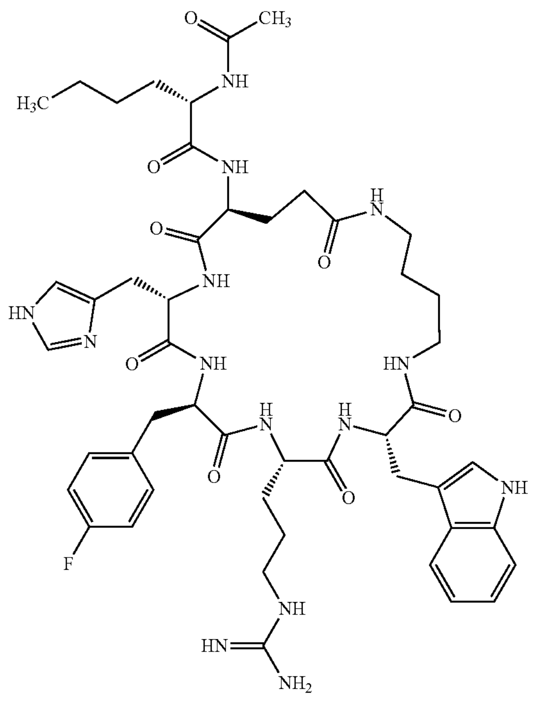 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O]

or a pharmaceutically acceptable salt thereof.

2. The pharmaceutically acceptable salt of the cyclic peptide according to claim 1, which is an acetate salt.

3. A pharmaceutical composition comprising the cyclic peptide according to claim 1, or a pharmaceutically acceptable salt thereof, and a pharmaceutically acceptable carrier.

4. The pharmaceutical composition of claim 3, wherein the pharmaceutically acceptable carrier is an aqueous solution comprising about 2.79 mg/mL of trisodium citrate dihydrate, about 9 mg/mL of sodium chloride and about 1 mg/mL of polysorbate 80.

5. The pharmaceutical composition of claim 4, wherein the cyclic peptide is in a trifluoroacetic acid salt form at a concentration of about 1.0 μg/mL.

6. The pharmaceutical composition of claim 5, further comprising about 0.10 mg/mL anhydrous citric acid.

7. The pharmaceutical composition of claim 4, wherein the aqueous solution is at about pH 6.5, and the composition further comprises sodium hydroxide or hydrochloric acid as needed to adjust pH.

8. A method for treating a melanocortin receptor-mediated disease, indication, condition or syndrome in a human or non-human mammal, comprising administering a therapeutically effective amount of the pharmaceutical composition of claim 3.

9. The method of claim 8, wherein the melanocortin receptor-mediated disease, indication, condition or syndrome in a human is ocular inflammation.

10. The method of claim 9, wherein the pharmaceutical composition is an aqueous pharmaceutical composition suitable for administration to the surface of an eye.

11. The method of claim 9, wherein the inflammation is caused by an ocular condition, wherein the ocular condition is dry eye disease, corneal ulcer, corneal erosion, corneal abrasion, corneal degeneration, corneal perforation, corneal scarring, epithelial defect, keratoconjunctivitis, idiopathic uveitis, corneal transplantation, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, pterygium, a wound sustained to ocular surface, post-photorefractive keratotomy eye pain and inflammation, thermal or chemical burn to the cornea, scleral wound, keratoconus or conjunctival wound.

12. The method of claim 11, wherein the inflammation is caused by dry eye disease or keratoconjunctivitis sicca.

13. A method for treating a condition responsive to changes in melanocortin receptor function in a human or non-human mammal, comprising administering a therapeutically effective amount of the pharmaceutical composition of claim 3.

14. A method of treating dry eye disease or keratoconjunctivitis sicca comprising administering no more than about 50 μL of the pharmaceutical composition of claim 5 per eye no more often than about three times per day.

15. The method of claim 14, wherein no more than about 150 ng of cyclic peptide or pharmaceutically acceptable salt thereof is administered per eye per day.

16. A trifluoroacetic acid salt of a cyclic peptide having the structure (SEQ ID NO: 51)

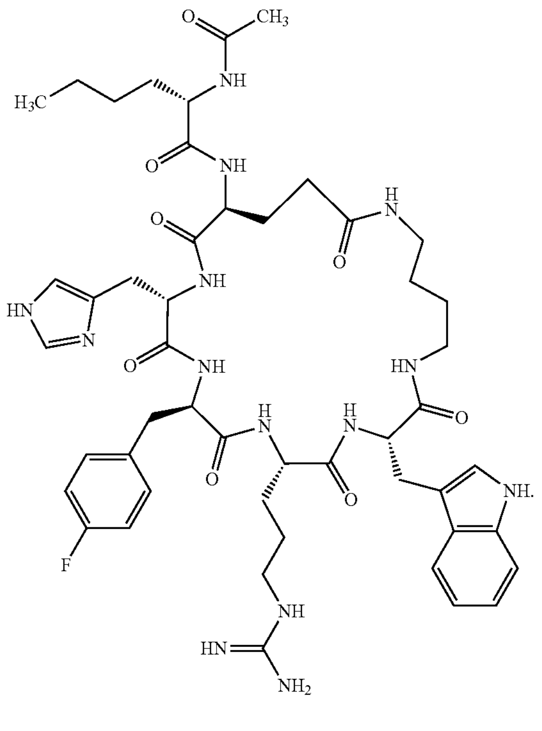 [SMILES: CCCC[C@H](NC(C)=O)C(=O)N[C@H]1CCC(=O)NCCCCNC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O]

17. A pharmaceutical composition comprising the trifluoroacetic acid salt according to claim 16, and a pharmaceutically acceptable carrier.

18. The pharmaceutical composition of claim 17, wherein the pharmaceutically acceptable carrier is an aqueous solution comprising about 2.79 mg/mL of trisodium citrate dihydrate, about 9 mg/mL of sodium chloride and about 1 mg/mL of polysorbate 80.

19. The pharmaceutical composition of claim 18, wherein the aqueous solution is at about pH 6.5, and the composition further comprises sodium hydroxide or hydrochloric acid as needed to adjust pH.

20. A method for treating a melanocortin receptor-mediated disease, indication, condition or syndrome in a human or non-human mammal, comprising administering a therapeutically effective amount of the pharmaceutical composition of claim 17, wherein the melanocortin receptor-mediated disease, indication, condition or syndrome in a human is ocular inflammation.

21. The method of claim 20, wherein the pharmaceutical composition is an aqueous pharmaceutical composition suitable for administration to the surface of an eye.

22. The method of claim 20, wherein the inflammation is caused by an ocular condition, wherein the ocular condition is dry eye disease, corneal ulcer, corneal erosion, corneal abrasion, corneal degeneration, corneal perforation, corneal scarring, epithelial defect, keratoconjunctivitis, idiopathic uveitis, corneal transplantation, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, pterygium, a wound sustained to ocular surface, post-photorefractive keratotomy eye pain and inflammation, thermal or chemical burn to the cornea, scleral wound, keratoconus or conjunctival wound.

23. The method of claim 22, wherein the inflammation is caused by dry eye disease or keratoconjunctivitis sicca.

24. A method of treating dry eye disease or keratoconjunctivitis sicca comprising administering no more than about 50 μL of the pharmaceutical composition of claim 19 per eye no more often than about three times per day.

25. The method of claim 24, wherein no more than about 150 ng of trifluoroacetic acid salt is administered per eye per day.

* * * * *